United States Patent
Beckham et al.

(10) Patent No.: US 12,371,718 B2
(45) Date of Patent: Jul. 29, 2025

(54) ENGINEERED MICROORGANISMS FOR THE DECONSTRUCTION OF POLYMERS

(71) Applicants: Alliance for Sustainable Energy, LLC, Golden, CO (US); UT-Battelle, LLC, Oak Ridge, TN (US)

(72) Inventors: Gregg Tyler Beckham, Golden, CO (US); Thelhawadigedara Lahiru Niroshan Jayakody, Wheat Ridge, CO (US); Adam Michael Guss, Oak Ridge, TN (US); Thomas David Mand, Oak Ridge, TN (US); Christopher W. Johnson, Denver, CO (US); Isabel Pardo Mendoza, Dos Hermanas (ES); Allison Jean Zimont Werner, Denver, CO (US)

(73) Assignees: Alliance for Sustainable Energy, LLC, Golden, CO (US); UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 17/198,230

(22) Filed: Mar. 10, 2021

(65) Prior Publication Data

US 2021/0285019 A1    Sep. 16, 2021

Related U.S. Application Data

(63) Continuation-in-part of application No. 17/055,626, filed as application No. PCT/US2019/032480 on May 15, 2019.

(60) Provisional application No. 62/671,477, filed on May 15, 2018.

(51) Int. Cl.
| | | |
|---|---|---|
| C12N 1/20 | (2006.01) | |
| C12N 9/18 | (2006.01) | |
| C12P 7/62 | (2022.01) | |

(52) U.S. Cl.
CPC .................. *C12P 7/62* (2013.01); *C12N 9/18* (2013.01); *C12Y 301/01* (2013.01)

(58) Field of Classification Search
CPC .......... C12N 9/18; C12N 1/20; C12N 15/625; C12N 15/70; C12P 7/18; C12P 7/44; C12Y 301/01
USPC ........................................................ 435/197
See application file for complete search history.

(56) References Cited

FOREIGN PATENT DOCUMENTS

| CN | 106754600 A | 5/2017 |
| CN | 107794252 A | 3/2018 |

OTHER PUBLICATIONS

Kwiatkowski et al., (Biochemistry 38:11643-11650, 1999.*
Kisselev L., (Structure, 2002, vol. 10: 8-9.*
Wristlock et al., (Quarterly Reviews of Biophysics 2003, vol. 36 (3): 307-340.*
Davos et al., (Proteins: Structure, Function and Genetics, 2000, vol. 41: 98-107.*
Biologicscorp, "Codon Optimization", Mar. 12, 2017, retrieved on Aug. 30, 2019 from https://web.archive.org/web/20170312215014/https:f/www .biologicscorp.com/codonoptimization-technical-platform/, pp. 1-5.
Elmore et al., "Development of a high efficiency integration system and promoter library for rapid modification of Pseudomonas putida KT244", Metabolic Engineering Communications, Dec. 2017, vol. 5, pp. 1-8.
Franden et al., "Engineering Pseudomonas putida KT2440 for efficient ethylene glycol utilization", Metabolic engineering, Jul. 2018, vol. 48, pp. 197-207.
Hara et al., "Transcriptomic analysis reveals a bifurcated terephthalate degradation pathway in *Rhodococcus* sp. strain RHA1", Journal of Bacteriology, Mar. 2007, vol. 189, No. 5, pp. 1641-1647.
Hosaka et al., "Novel Tripartie Aromatic Acid Transporter Essential for Terephthalate Uptake in *Comamonas* sp. Strain E6", Applied and Environmental Microbiology, Oct. 2013, vol. 79, No. 19, pp. 6148-6155.
Jayakody et al., "Thermochemical wastewater valorization via enhanced microbial toxicity tolerance", Energy & Environmental Science, 2018, vol. 11, pp. 16-25-16-38.
Rorrer et al., "Combining Reclaimed PET with Bio-based Monomers Enables Plastics Upcycling", Joule, Apr. 17, 2019, vol. 3, No. 4, pp. 1006-1027.
Sasoh et al., "Characterization of the Terephthalate Degradation Genes of *Comamonas* sp. Strain E6", Applied Environmental Microbiology, Mar. 2006, vol. 72, No. 3, pp. 1825-1832.
Yoshida et al., "Discovery of a Bacterium that Degrades and Assimilates Poly(ethyleneA terephthalate) could Serve as a Degradation and/or Fermentation Platform for Biological Recycling of PET Waste Products", Press Release Kyoto Institute of Technology, Mar. 30, 2016, retrieved on Aug. 30, 2019 from https://www.keio.ac.jp/en/press releases/2016/cb96u90000005501-att/160330_2.pdf, pp. 1-4.

(Continued)

*Primary Examiner* — Robert B Mondesi
*Assistant Examiner* — Mohammad Y Meah
(74) *Attorney, Agent, or Firm* — Sam J. Barkley; Michael A. McIntyre

(57) ABSTRACT

Disclosed herein are methods and compositions for catalytic glycolysis to deconstruct PET to bis(2-hydroxyethyl) terephthalate (BHET). For BHET conversion to terephthalate and ethylene glycol, we engineer *Pseudomonas putida* KT2440 with PETase and MHETase enzymes from *Ideonella sakaiensis*. We further engineer *P. putida* to convert terephthalate to a performance-advantaged bioproduct, β-ketoadipic acid, and for improved utilization of ethylene glycol, a byproduct of BHET catabolism. In a bioreactor, we produce 15.1±0.6 g/L of β-ketoadipic acid (βKA) from BHET at 76±3% molar yield. Lastly, we demonstrate conversion of catalytically depolymerized PET to βKA. Overall, this work highlights the potential of tandem catalytic deconstruction and biological conversion as a means to upcycle waste PET.

8 Claims, 46 Drawing Sheets

Specification includes a Sequence Listing.

(56) References Cited

OTHER PUBLICATIONS

Yoshida et al., "A bacterium that degrades and assimilates poly-(ethylene terephthalate)", Science, Mar. 11, 2016, vol. 351, No. 6278, pp. 1196-1199.
Dvorak et al., "Bioremediation 3.0: Engineering pollutant-removing bacteria in the times of systemic biology", Biotechnology Advances, Aug. 2017, vol. 35, No. 5, pp. 845-866.
Patrauchan et al., "Catabolism of Benzoate and Phthalate in *Rhodococcus* sp. Strain RHA1: Redundancies and Converge", Journal of Bacteriology, Jun. 2005, vol. 187, No. 12, pp. 4050-4063.
Werner et al., "Tandem chemical deconstruction and biological upcycling poly(ethylene terephthalate) to [beta]-ketoadipic acid by Pseudomonas putida KT2440", Metabolic Engineering, Jul. 2021, vol. 67, pp. 250-261.
Extended European Search Report and Preliminary Opinion for European Application No. 19804066.9, dated Feb. 4, 2022, pp. 1-11.

\* cited by examiner

(A) PETase (904 bp)

TCATCAAGTCAAAACACTATATAGGAACGAAACCATGAACTTCCCTCGCGCGTCGCGCCTGATGCAGGCGGCGGTCCTCGGTG
GTCTGATGGCAGTCAGCGCCGCGGCCACCGCTCAGACCAACCCATACGCCCGCGGCCCAAACCCTACCGCGGCCAGCCTGGAA
GCCTCTGCCGGCCCATTCACCGTGCGCAGCTTCACCGTCAGTCGCCCGTCGGGCTATGGTGCCGGCACCGTCTACTACCCAACC
AACGCTGGCGGCACCGTCGGCGCCATCGCAATCGTGCCGGGCTATACCGCCCGCCAGTCCTCGATCAAGTGGTGGGGCCCACG
TCTGGCCTCCCACGGCTTCGTTGTTATCACCATCGACACCAACTCGACCCTGGACCAGCCGTCCTCCCGCTCGAGCCAGCAGAT
GGCTGCTCTGCGCCAGGTAGCTTCGCTGAACGGCACCAGCTCTAGCCCAATCTACGGCAAAGTGGACACCGCTCGCATGGGCG
TGATGGGTTGGTCCATGGGCGGTGGTGGTTCCCTGATCTCCGCTGCTAATAATCCTTCCCTGAAGGCCGCCGCCCCGCAGGCCC
CATGGGACTCCTCGACCAACTTCTCGAGCGTGACCGTGCCGACCCTGATCTTCGCTTGCGAAAACGACAGCATCGCTCCGGTG
AACTCCTCCGCGCTGCCTATCTACGACTCCATGAGCCGCAACGCCAAGCAATTCCTGGAAATCAACGGCGGTTCCCACTCCTGC
GCTAACTCGGGCAACTCGAACCAAGCCCTGATCGGCAAGAAGGGCGTAGCATGGATGAAGCGTTTCATGGATAACGACACCC
GTTACTCGACCTTCGCCTGCGAAAACCCGAACTCTACTCGCGTCAGCGACTTCCGCACTGCGAACTGCAGC

(B) MEHTase (1809 bp)

TAACAAGGATTACATATAAGGGTATATCAAATGCAGACCACCGTCACCACTATGCTGCTGGCATCGGTCGCCCTGGCCGCCTG
CGCAGGCGGCGGCAGCACCCCGCTGCCGCTGCCGCAGCAACAGCCGCCACAGCAGGAGCCGCCGCCTCCTCCAGTCCCGCTG
GCTTCCCGTGCTGCGTGTGAGGCCCTGAAGGACGGCAACGGGGACATGGTTTGGCCGAACGCCGCCACCGTAGTTGAAGTGGC
CGCATGGCGCGACGCTGCCCCGGCTACCGCGTCCGCCGCCGCTCTGCCGGAACACTGCGAAGTTAGCGGCGCCATCGCCAAGC
GCACTGGTATTGACGGTTATCCGTACGAAATCAAGTTCCGCCTGCGCATGCCGGCGGAGTGGAATGGCCGTTTCTTCATGGAG
GGTGGTTCCGGCACCAACGGCTCCCTGAGCGCGGCCACCGGCAGCATCGGTGGCGGCCAGATCGCCTCGGCCCTGTCCCGCAA
CTTCGCCACCATCGCGACCGACGGTGGCCACGACAACGCTGTCAACGACAATCCAGACGCCCTGGGTACGGTAGCGTTCGGCC
TGGACCCACAGGCTCGCCTGGACATGGGTTACAATTCGTACGACCAGGTGACCCAAGCTGGCAAAGCCGCCGTTGCCCGTTTC
TACGGCCGTGCCGCCGACAAGTCGTACTTCATCGGCTGCTCGGAAGGTGGTCGGGAGGGCATGATGCTCAGCCAACGCTTCCC
ATCCCACTACGACGGTATCGTCGCCGGTGCCCCTGGCTACCAGCTGCCTAAAGCCGGTATCTCGGGCGCTTGGACCACTCAGTC
GCTGGCCCCGGCGGCGGTGGGCCTGGACGCTCAGGGCGTCCCGCTGATCAACAAGAGCTTCTCCGATGCCGACCTGCACCTGC
TGTCGCAGGCCATCCTCGGTACTTGCGATGCGCTGGACGGCCTGGCTGACGGCATCGTTGACAACTACCGCGCGTGCCAGGCC
GCTTTCGACCCGGCTACCGCGGCTAACCCTGCCAACGGTCAAGCTCTGCAATGTGTGGGTGCCAAAACCGCCGATTGCCTGAG
CCCGGTACAGGTTACCGCCATCAAACGTGCAATGGCCGGCCCGGTCAACAGCGCCGGCACCCCGCTGTACAACCGTTGGGCCT
GGGACGCTGGTATGAGCGGCCTGTCCGGTACCACCTACAATCAGGGCTGGCGTTCCTGGTGGCTGGGTAGCTTCAACTCCTCG
GCGAACAACGCGCAGCGTGTTTCGGGTTTCTCCGCCCGCTCCTGGCTGGTCGACTTCGCCACCCCACCAGAGCCTATGCCGATG
ACCCAGGTGGCTGCACGCATGATGAAATTCGACTTCGACATCGACCCGCTGAAGATCTGGGCCACCAGCGGCCAGTTCACCCA
GTCGAGCATGGACTGGCACGGGGCCACCTCCACCGACCTGGCCGCCTTCCGCGATCGTGGCGGCAAGATGATCCTGTACCACG
GTATGAGCGACGCAGCCTTCTCGGCCCTGGACACCGCTGACTACTACGAACGCCTGGGCGCCGCTATGCCGGGCGCCGCGGGC
TTCGCTCGTCTGTTCCTCGTCCCAGGCATGAACCACTGTTCGGGCGGTCCAGGTACCGACCGTTTCGACATGCTGACCCCTCTG
GTGGCGTGGGTTGAGCGCGGCGAAGCCCCGGACCAGATCTCGGCGTGGAGCGGCACCCCAGGCTACTTCGGCGTCGCTGCCCG
TACCCGCCCGCTGTGCCCGTACCCGCAAATCGCACGCTACAAGGGTTCCGGCGATATCAACACCGAAGCAAACTTCGCCTGCG
CCGCGCCTCCG

FIGs. 6A-6B

| Plasmid sequence 5'-3' |
|---|
| TTGAGATCCTTTTTTTCTGCGCGTAATCTGCTGCTTGCAAACAAAAAAACCACCGCTACCAGCGGTGGTTTGTTTGCCGGATCA |
| AGAGCTACCAACTCTTTTTCCGAAGGTAACTGGCTTCAGCAGAGCGCAGATACCAAATACTGTTCTTCTAGTGTAGCCGTAGTT |
| AGGCCACCACTTCAAGAACTCTGTAGCACCGCCTACATACCTCGCTCTGCTAATCCTGTTACCAGTGGCTGCTGCCAGTGGCGA |
| TAAGTCGTGTCTTACCGGGTTGGACTCAAGACGATAGTTACCGGATAAGGCGCAGCGGTCGGGCTGAACGGGGGGTTCGTGCA |
| CACAGCCCAGCTTGGAGCGAACGACCTACACCGAACTGAGATACCTACAGCGTGAGCTATGAGAAAGCGCCACGCTTCCCGA |
| AGGGAGAAAGGCGGACAGGTATCCGGTAAGCGGCAGGGTCGGAACAGGAGAGCGCACGAGGGAGCTTCCAGGGGGAAACGC |
| CTGGTATCTTTATAGTCCTGTCGGGTTTCGCCACCTCTGACTTGAGCGTCGATTTTTGTGATGCTCGTCAGGGGGCGGAGCCT |
| ATGGAAAAACGCCTCACACAGGAAACAGCTATGACATGATTACGAATTCGAGCTCGTACCCGTGCGATTACTGTGGGAGCG |
| GGCATGCCCGCGAATGGGAGCAACACAAGGCTCAATGGTTGACGGTGTGCGCCAGCATCACCGACAACTGGCACAGCGGCCG |
| CCCGCTCTCTGCATGCCACTGGTTGAACGCCTGCTGCACCAGAGCCAGGTCGCGGCTGGCTGGTTGGCTGCTTGTCGATCACCTT |
| CTGCGCAATCAACGCCGCTGCCATGTCATCGGTCGGGATGAACGTGTCCTTGCCGACCATGCGCAAGAACCGTGGCGCCGACA |
| ACCCGCCCAACTGGTTGCCGTGCTTGGCCAGGTACTCCACAAGCCGACAATGTCGGTCACTGGCCAATCGCGGATGAATGCA |
| CCAAAACTGCCATGCGCCTTGCGATATCCAGCACCATTTGCGCATTGCGTGGCACGCTCTTGAGCTTGCCCAGGTGGCGGAT |
| AATGCGCTCATCCTGCATCAACCGCTCCAGATGCTCGGCGCCCATCAGCACCACTTTCTCCGGGTCGAAGCCAAAGAACACCT |
| GCTCGAACGCCGGCCACTTGGCATCCACCAGGCTGTGCTTGAGCCCCGCGCGGAACACGCGCAGGGCCAATGTCGACAGGTA |
| GCGGTCGTCACTGATGTCGCGCAGTTGCGCCCGCGTGCGCGGCTGCGGCAGGAAAGCCTCCAGCGCCTGGGCCGAACCAAAG |
| CGGTTCAGGCAATACTCAGTGTGAAATTGTTATCCGCTCACAATTCCACACATTATACGAGCCGATGATTAATTGTCAACAGCT |
| CTTCATCAAGTCAAAACACTATATAGGAACGAAACCATGAACTTCCCTCGCGCGTCGCGCCTGATGCAGGCGGCGGTCCTCGG |
| TGGTCTGATGGCAGTCAGCGCCGCGGCCACCGCTCAGACCAACCCATACGCCCGCGGCCCAAACCCTACCGCGGCCAGCCTGG |
| AAGCCTCTGCCGGCCCATTCACCGTGCGCAGCTTCACCGTCAGTCGCCCGTCGGGCTATGGTGCCGGCACCGTCTACTACCCAA |
| CCAACGCTGGCGGCACCGTCGGCGCCATCGCAATCGTGCCGGGCTATACCGCCGCCAGTCCTCGATCAAGTGGTGGGCCCA |
| CGTCTGGCCTCCCACGGCTTCGTTGTTATCACCATCGACACCAACTCGACCCTGGACCAGCCGTCCTCCCGCTCGAGCCAGCAG |
| ATGGCTGCTCTGCGCCAGGTAGCTTCGCTGAACGGCACCAGCTCTAGCCCAATCTACGGCAAAGTGGACACCGCTCGCATGGG |
| CGTGATGGGTTGGTCCATGGGCGGTGGTGGTTCCCTGATCTCCGCTGCTAATAATCCTTCCCTGAAGGCCGCCGCCCCGCAGGC |
| CCCATGGGACTCCTCGACCAACTTCTCGAGCGTGACCGTGCCGACCCTGATCTTCGCTTGCGAAAACGACAGCATCGCTCCGGT |
| GAACTCCTCCGCGCTGCCTATCTACGACTCCATGAGCCGCAACGCCAAGCAATTCCTGGAAATCAACGGCGGTTCCCACTCCT |
| GCGCTAACTCGGGCAACTCGAACCAAGCCCTGATCGGCAAGAAGGGCGTAGCATGGATGAAGCGTTTCATGGATAACGACAC |
| CCGTTACTCGACCTTCGCCTGCGAAAACCCGAACTCTACTCCGTCAGCGACTTCCGCACTGCGAACTGCAGCCTATAACAAG |
| GATTACATATAAGGGTATATCAAATGCAGACCACCGTCACCACTATGCTGCTGGCATCGGTCGCCCTGGCCGCCTGCGCAGGC |
| GGCGGCAGCACCCCGCTGCCGCTGCCCGCAGCAACAGCCGCCACAGCAGGAGCCGCCGCCTCCTCCAGTCCCGCTGGCTTCCCG |
| TGCTGCGTGTGAGGCCCTGAAGGACGGCAACGGGGACATGGTTTGGCCGAACGCCGCCACCGTAGTTGAAGTGGCCGCATGG |
| CGCGACGCTGCCCCGCTACCGCGTCCGCCGCCGCTCTGCCGGAACACTGCGAAGTTAGCGGCGCCATCGCCAAGCGCACTGG |
| TATTGACGGTTATCCGTACGAAATCAAGTTCCGCCTGCCGCATGCCGGCGGAGTGGAATGGCCGTTCTTCATGGAGGGTGGTTC |
| CGGCACCAACGGCTCCCTGAGCGCGGCCACCGGCAGCATCCGGTGCGGCCAGATCGCCTCGGCCCTGTCCCGCAACTTCGCCA |
| CCATCGCCGACCGACGGTGGCCACGACAACGCTGTCAACGACAATCCAGACGCCCTGGGTACCGGTAGCGTTCGGCCTGGACCCA |
| CAGGCTCGCCTGGACATGGGTTACAATTCGTACGACCAGGTGACCCAAGCTGGCAAAGCCGCCGTTGCCCGTTTCTACGGCCG |
| TGCCGCCGACAAGTCGTACTTCATCGGCTGCTCGGAAGGTGGTCGGGAGGGCATGATGCTCAGCCAACGCTTCCCATCCCACT |
| ACGACGGTATCGTCGCCGGTGCCCCTGGCTACCAGCTGCCTAAAGCCGGTATCTCGGGCGCTTGGACCACTCAGTCGCTGGCC |
| CCGGCGGCGGTGGGCCTGGACGCTCAGGGCGTCCCGCTGATCAACAAGAGCTTCTCCGATGCCGACCTGCACCTGCTGTCGCA |
| GGCCATCCTCGGTACTTGCGATGCGCTGGACGCCCTGGCTGACGGCATCGTTGACAACTACCGCGCGTGCCAGGCCGCTTTCG |
| ACCCGGCTACCGCGGCTAACCCTGCCAACGGTCAAGCTCTGCAATGTGTGGGTCCCAAAACCGCCGATTGCCTGAGCCCGGTA |
| CAGGTTACCGCCATCAAACGTGCAATGGCCGGCCCGGTCAACAGCGCCGGCACCCGCTGTACAACGTTGGGCCTGGACGC |
| TGGTATGAGCGGCCTGTCCGGTACCACCTACAATCAGGGCTGGCGTCCTGGTGGCTGGGTAGCTTCAACTCCTCGGCGAACA |
| ACGCGCAGCGTGTTTCCGGGTTTCTCCGCCCGCTCCTGGCTGGTCGACTTCGCCACCCCACCAGAGCCTATGCCGATGACCCAGG |
| TGCTGCACGCATGATGAAATTCGACTTCGACATCGACCCGCTGAAGATCTGGGCCACCAGCGGCCAGTTCACCCAGTCGAGC |

FIG. 8

```
ATGGACTGGCACGGGGCCACCTCCACCGACCTGGCCGCCTTCCGCGATCGTGGCGGCAAGATGATCCTGTACCACGGTATGAG
CGACGCAGCCTTCTCGGCCCTGGACACCGCTGACTACTACGAACGCCTGGGCGCCGCTATGCCGGGCGCCGCGGGCTTCGCTC
GTCTGTTCCTCGTCCCAGGCATGAACCACTGTTCGGGCGGTCCAGGTACCGACCGTTTCGACATGCTGACCCTCTGGTGGCGT
GGGTTGAGCGCGGCGAAGCCCCGGACCAGATCTCGGCGTGGAGCGGCACCCCAGGCTACTTCGGCGTCGCTGCCCGTACCCGC
CCGCTGTGCCCGTACCCGCAAATCGCACGCTACAAGGGTTCCGGCGATATCAACACCGAAGCAAACTTCGCCTCGCCGCGCC
TCCGAGTCAAAAGCCTCCGGTCGGAGGCTTTTGACTTCAAAACCACCCTGCTGTCGATGATGCTGCCGCTGATGCACCACGGC
ATGCTGGTGATGGCCTGCCTACAGCTAGTCGGCACTGCTCGAGACCGTGGTGGCGCACGCCTTATGGCTCCAGCCTACCA
CGCAGGCGCCGATGGCAAGCGCGAACTCGACCCACACGAAATCGCCCTGTGCCCGCGCCCTGGGCCAACGCCTGGCGACCACG
GCCAAGGCCCTGGAGGCGGCGCGTGGCTAGAAAGCCAAGGCATTGCCGCCGGTCCAATGGCTGGTACCACGCCTGCGCCTG
ACGCGGGCATTGAGCCTGGCATGCTTCTTCGGCCTGATCGCCCTGCTGGTGGTGAACAACCTGTGGTTCGCCAACCTGCATGGG
GCCAGGGTCGAGGTGATCCTGGCGATCGAGCTGGTGCCGTTGCTGTTGCTGTTGCCAGGCATGCTGAAAGGCAGCGCCCGGGC
GCATGCCTGGACCTGCTTCGTGGTGAATATCTATTTCATCAAGGGCGTGCTGGCGGCGTTCGACCCGGCGCGGGCGGTATTCG
GCTGGCTTGAAGTGCTGGTGAGCCTGGGGCTGTTCATTGCCGGGCTACTGTACGTGCGCTGGAAGTTCCAGCATGAGCGGCGC
ATGGCGGCGAAGGCAGTTAGATTTCCTGCAGGCATGCAAGCTTGGCACTGGCCGTCGTTTTACAACGTCGTGACCGGAATTG
CCAGCTGGGGCGCCCTCTGGTAAGGTTGGGAAGCCCTGCAAACAGGATGAGGATCGTTTCGCATGATTGAACAAGATGGATTG
CACGCAGGTTCTCCGGCCGCTTGGGTGGAGAGGCTATTCGGCTATGACTGGGCACAACAGACAATCGGCTGCTCTGATGCCGC
CGTGTTCCGGCTGTCAGCGCAGGGGCGCCCGGTTCTTTTTGTCAAGACCGACCTGTCCGGTGCCCTGAATGAACTCCAAGACG
AGGCAGCGCGGCTATCGTGGCTGGCCACGACGGGCGTTCCTTGCGCAGCTGTGCTCGACGTTGTCACTGAAGCGGGAAGGGAC
TGGCTGCTATTGGGCGAAGTGCCGGGGCAGGATCTCCTGTCATCTCACCTTGCTCCTGCCGAGAAAGTATCCATCATGGCTGAT
GCAATGCGGCGGCTGCATACGCTTGATCCGGCTACCTGCCCATTCGACCACCAAGCGAAACATCGCATCGAGCGAGCACGTAC
TCGGATGGAAGCCGGTCTTGTCGATCAGGATGATCTGGACGAAGAGCATCAGGGGCTCGCGCCAGCCGAACTGTTCGCCAGGC
TCAAGGCGCGGATGCCCGACGGCGAGGATCTCGTCGTGACCCATGGCGATGCCTGCTTGCCGAATATCATGGTGGAAAATGGC
CGCTTTTCTGGATTCATCGACTGTGGCCGGCTGGGTGTGGCGGACCGCTATCAGGACATAGCGTTGGCTACCCGTGATATTGCT
GAAGAGCTTGGCGGCGAATGGGCTGACCGCTTCCTCGTGCTTTACGGTATCGCCGCTCCCGATTCGCAGCGCATCGCCTTCTAT
CGCCTTCTTGACGAGTTCTTCTGAGCGACGATGAACATCAAAAAGTTTGCAAAACAAGCAACAGTATTAACCTTTACTACCGC
ACTGCTGGCAGGAGGCGCAACTCAAGCGTTTGCGAAAGAAACGAACCAAAAGCCATATAAGGAAACATACGGCATTTCCCAT
ATTACACGCCATGATATGCTGCAAATCCCTGAACAGCAAAAAAATGAAAAATATCAAGTTTCTGAATTTGATTCGTCCACAAT
TAAAAATATCTCTTCTGCAAAAGGCCTGGACGTTTGGGACAGCTGGCCATTACAAAACGCTGACGGCACTGTCGCAAACTATC
ACGGCTACCACATCGTCTTTGCATTAGCCGGAGATCCTAAAAATGCGGATGACACATCGATTTACATGTTCTATCAAAAAGTC
GGCGAAACTTCTATTGACAGCTGGAAAAACGCTGGCCGCGTCTTTAAAGACAGCGACAAATTCGATGCAAATGATTCTATCCT
AAAAGACCAAACACAAGAATGGTCAGGTTCAGCCACATTTACATCTGACGGAAAAATCCGTTTATTCTACACTGATTTCTCCG
GTAAACATTACGGCAAACAAACACTGACAACTGCACAAGTTAACGTATCAGCATCAGACAGCTCTTTGAACATCAACGGTGTA
GAGGATTATAAATCAATCTTTGACGGTGACGGAAAAACGTATCAAAATGTACAGCAGTTCATCGATGAAGGCAACTACAGCTC
AGGCGACAACCATACGCTGAGAGATCCTCACTACGTAGAAGATAAAGGCCACAAATACTTAGTATTTGAAGCAAACACTGGA
ACTGAAGATGGCTACCAAGGCGAAGAATCTTTATTTAACAAAGCATACTATGGCAAAAGCACATCATTCTTCCGTCAAGAAAG
TCAAAAACTTCTGCAAAGCGATAAAAAACGCACGGCTGAGTTAGCAAACGGCGCTCTCGGTATGATTGAGCTAAACGATGATT
ACACACTGAAAAAAGTGATGAAACCGCTGATTGCATCTAACACAGTAACAGATGAAATTGAACGCGCGAACGTCTTTAAAAT
GAACGGCAAATGGTACCTGTTCACTGACTCCCGCGGATCAAAAATGACGATTGACGGCATTACGTCTAACGATATTTACATGC
TTGGTTATGTTTCTAATTCTTTAACTGGCCCATACAAGCCGCTGAACAAAACTGGCCTTGTGTTAAAAATGGATCTTGATCCTA
ACGATGTAACCTTTACTTACTCACACTTCGCTGTACCTCAAGCGAAAGGAAACAATGTCGTGATTACAAGCTATATGACAAAC
AGAGGATTCTACGCAGACAAACAATCAACGTTTGCGCCGAGCTTCCTGCTGAACATCAAAGGCAAGAAAACATCTGTTGTCAA
AGACAGCATCCTTGAACAAGGACAATTAACAGTTAACAAATAATCAGACCCCGTAGAAAAGATCAAAGGATCTTC
```

FIG. 8 (continued)

| (A) *PETase* |
|---|
| MNFPRASRLMQAAVLGGLMAVSAAATAQTNPYARGPNPTAASLEASAGPFTVRSFTVSRPSGYGAGTVYYPTNAGGTVGAIAIV PGYTARQSSIKWWGPRLASHGFVVITIDTNSTLDQPSSRSSQQMAALRQVASLNGTSSSPIYGKVDTARMGVMGWSMGGGGSLISA ANNPSLKAAAPQAPWDSSTNFSSVTVPTLIFACENDSIAPVNSSALPIYDSMSRNAKQFLEINGGSHSCANSGNSNQALIGKKGVAW MKRFMDNDTRYSTFACENPNSTRVSDFRTANCS* |
| (B) *MEHTase* |
| MQTTVTTMLLASVALAACAGGGSTPLPLPQQQPPQQEPPPPPVPLASRAACEALKDGNGDMVWPNAATVVEVAAWRDAAPATA SAAALPEHCEVSGAIAKRTGIDGYPYEIKFRLRMPAEWNGRFFMEGGSGTNGSLSAATGSIGGGQIASALSRNFATIATDGGHDNAV NDNPDALGTVAFGLDPQARLDMGYNSYDQVTQAGKAAVARFYGRAADKSYFIGCSEGGREGMMLSQRFPSHYDGIVAGAPGYQL PKAGISGAWTTQSLAPAAVGLDAQGVPLINKSFSDADLHLLSQAILGTCDALDGLADGIVDNYRACQAAFDPATAANPANGQALQC VGAKTADCLSPVQVTAIKRAMAGPVNSAGTPLYNRWAWDAGMSGLSGTTYNQGWRSWWLGSFNSSANNAQRVSGFSARSWLV DFATPPEPMPMTQVAARMMKFDFDIDPLKIWATSGQFTQSSMDWHGATSTDLAAFRDRGGKMILYHGMSDAAFSALDTADYYER LGAAMPGAAGFARLFLVPGMNHCSGGPGTDRFDMLTPLVAWVERGEAPDQISAWSGTPGYFGVAARTRPLCPYPQIARYKGSGDI NTEANFACAAPP |

FIGs. 9A-9B

| PETase_GFP 5'-3' |
|---|
| ATCATTCAGGACGAGCCTCAGACTCCAGCGTAACTGGACTGAAAACAAACTAAAGCGCCCTTGTGGCGCTTTAGTTTTGTTCC
GCGGCCACCGGCTGGCTCGCTTCGCTCGGCCCGTGGACAACCCTGCTGGACAAGCTGATGGACAGGCTGCGCCTGCCCACGAG
CTTGACCACAGGGATTGCCCACCGGCTACCCAGCCTTCGACCACATACCCACCGGCTCCAACTGCGCGGCCTGCGGCCTTGCC
CCATCAATTTTTTTAATTTTCTCTGGGGAAAAGCCTCCGGCCTGCGGCCTGCGCGCTTCGCTTGCCGGTTGGACACCAAGTGGA
AGGCGGGTCAAGGCTCGCGCAGCGACCGCGCAGCGGCTTGGCCTTGACGCGCCTGGAACGACCCAAGCCTATGCGAGTGGGG
GCAGTCGAAGGCGAAGCCCGCCCGCCTGCCCCCCGAGCCTCACGGCGGCGAGTGCGGGGGTTCCAAGGGGGCAGCGCCACCT
TGGGCAAGGCCGAAGGCCGCGCAGTCGATCAACAAGCCCCGGAGGGGCCACTTTTTGCCGGAGGGGGAGCCGCGCCGAAGGC
GTGGGGGAACCCCGCAGGGGTGCCCTTCTTTGGGCACCAAAGAACTAGATATAGGGCGAAATGCGAAAGACTTAAAAATCAA
CAACTTAAAAAAGGGGGGTACGCAACAGCTCATTGCGGCACCCCCCGCAATAGCTCATTGCGTAGGTTAAAGAAAATCTGTAA
TTGACTGCCACTTTTACGCAACGCATAATTGTTGTCGCGCTGCCGAAAAGTTGCAGCTGATTGCGCATGGTGCCGCAACCGTGC
GGCACCCTACCGCATGGAGATAAGCATGGCCACGCAGTCCAGAGAAATCGGCATTCAAGCCAAGAACAAGCCCGGTCACTGG
GTGCAAACGGAACGCAAAGCGCATGAGGCGTGGGCCGGGCTTATTGCGAGGAAACCCACGGCGGCAATGCTGCTGCATCACC
TCGTGGCGCAGATGGGCCACCAGAACGCCGTGGTGGTCAGCCAGAAGACACTTTCCAAGCTCATCGGACGTTCTTTGCGGACG
GTCCAATACGCAGTCAAGGACTTGGTGGCCGAGCGCTGGATCTCCGTCGTGAAGCTCAACGGCCCCGGCACCGTGTCGGCCTA
CGTGGTCAATGACCGCGTGGCGTGGGGCCAGCCCCGCGACCAGTTGCGCCTGTCGGTGTTCAGTGCCGCCGTGGTGGTTGATC
ACGACGACCAGGACGAATCGCTGTTGGGGCATGGCGACCTGCCGCCGCCATCCCGACCCTGTATCCGGGCGAGCAGCAACTACC
GACCGGCCCCGGCGAGGAGCCGCCCAGCCAGCCCGGCATTCCGGGCATGGAACCAGACCTGCCAGCCTTGACCGAAACGGAG
GAATGGGAACGGCGCGGGCAGCAGCGCCTGCCGATGCCCGATGAGCCGTGTTTTCTGGACGATGGCGAGCCGTTGGAGCGC
CGACACGGGTCACGCTGCCGCGCCGGTAGTACGTAAGAGGTTCCAACTTTCACCATAATGAAATAAGATCACTACCGGGCGTA
TTTTTTGAGTTATCGAGATTTTCAGGAGCTAAGGAAGCTAAAATGAGCCATATTCAACGGGAAACGTCTTGCTCGAGGCCGCG
ATTAAATTCCAACATGGATGCTGATTTATATGGGTATAAATGGGCTCGCGATAATGTCGGGCAATCAGGTGCGACAATCTATC
GATTGTATGGGAAGCCCGATGCGCCAGAGTTGTTTCTGAAACATGGCAAAGGTAGCGTTGCCAATGATGTTACAGATGAGATG
GTCAGGCTAAACTGGCTGACGGAATTTATGCCTCTTCCGACCATCAAGCATTTTATCCGTACTCCTGATGATGCATGGTTACTC
ACCACTGCGATCCCAGGGAAAACAGCATTCCAGGTATTAGAAGAATATCCTGATTCAGGTGAAAATATTGTTGATGCGCTGGC
AGTGTTCCTGCGCCGGTTGCATTCGATTCCTGTTTGTAATTGTCCTTTTAACGGCGATCGCGTATTTCGTCTCGCTCAGGCGCAA
TCACGAATGAATAACGGTTTGGTTGGTGCGAGTGATTTTGATGACGAGCGTAATGGCTGGCCTGTTGAACAAGTCTGGAAAGA
AATGCATAAGCTTTTGCCATTCTCACCGGATTCAGTCGTCACTCATGGTGATTTCTCACTTGATAACCTTATTTTTGACGAGGGG
AAATTAATAGGTTGTATTGATGTTGGACGAGTCGGAATCGCAGACCGATACCAGGATCTTGCCATCCTATGGAACTGCCTCGG
TGAGTTTTCTCCTTCATTACAGAAACGGCTTTTTCAAAAATATGGTATTGATAATCCTGATATGAATAAATTGCAGTTTCACTTG
ATGCTCGATGAGTTTTTCTGAGGGCGGATCCCCCTCAAGTCAAAAGCCTCCGGTCGGAGGCTTTTGACTTTCTGCTATGGAGGT
CAGGTATGATTTTGCATTAGGCACCCCAGGCTTTACACTTTATGCTTCCGGCTCGTATGTTGTGTGGAATTGTGAGCGGATAAC
AATTTCACACTTTCATCAAGTCAAAACACTATATAGGAACGAAACCATGAACTTCCCTCGCGCGTCGCGCCTGATGCAGGCGG
CGGTCCTCGGTGGTCTGATGGCAGTCAGCGCCGCGGCCACCGCTCAGACCAACCCATACGCCGGCGGCCCAAACCCTACCGCG
GCCAGCCTGGAAGCCTCTGCCGGCCCATTCACCGTGCGCAGCTTCACCGTCAGTCGCCCGTCGGGCTATGGTGCCGGCACCGT
CTACTACCCAACCAACGCTGGCGGCACCGTCGGCGCCATCGCAATCGTGCCGGGCTATACCGCCCGCCAGTCCTCGATCAAGT
GGTGGGGCCCACGTCTGGCCTCCCACGGCTTCGTTGTTATCACCATCGACACCAACTCGACCCTGGACCAGCCGTCCTCCCGCT
CGAGCCAGCAGATGGCTGCTCTGCGCCAGGTAGCTTCGCTGAACGGCACCAGCTCTAGCCCAATCTACGGCAAAGTGGACACC
GCTCGCATGGGCGTGATGGGTTGGTCCATGGGCGGTGGTGGTTCCCTGATCTCCGCTGCTAATAATCCTTCCCTGAAGGCCGCC
GCCCCGCAGGCCCCATGGGACTCCTCGACCAACTTCTCGAGCGTGACCGTGCCGACCCTGATCTTCGCTTGCGAAAACGACAG
CATCGCTCCGGTGAACTCCTCCGCGCTGCCTATCTACGACTCCATGAGCCGCAACGCCAAGCAATTCCTGGAAATCAACGGCG
GTTCCCACTCCTGCGCTAACTCGGGCAACTCGAACCAAGCCCTGATCGGCAAGAAGGGCGTAGCATGGATGAAGCGTTTCATG
GATAACGACACCCGTTACTCGACCTTCGCCTGCGAAAACCCGAACTCTACTCGCGTCAGCGACTTCCGCACTGCGAACTGCAG
CGGTGGTTCTGAGGAATCTTACATGAGCAAGGGCGAGGAGCTCTTTACCGGCGTCGTCCCATTCTCGTTGAGCTGGACGGCG
ACGTGAACGGACATAAGTTCAGTGTCTCGGGCGAGGGCGAAGGAGATGCCACCTATGGGAAGCTAACCCTGAAGTTCATCTG
CACAACCGGGAAGCTGCCGGTCCCTGGCCGACGCTGGTTACCACCCTGACCTACGGCGTGCAATGCTTCTCGCGCTACCCTG
ACCACATGAAGCGCCACGACTTCTTCAAATCCGCTATGCCGGAGGGCTACGTCCAGGAACGCACCATATTCTTCAAGGACGAC
GGTAACTACAAGACGCGCGCCGAAGTCAAGTTCGAGGGGGATACCCTCGTGAACCGAATCGAGTTGAAGGGGATCGACTTCA
AGAAGATGGCAACATCCTCGGCCACAAACTGGAGTACAACTACAATTCGCATAACGTGTACATCATGGCCGACAAGCAGAA
GAATGGCATCAAGGTGAACTTCAAGATTCGCCACAACATCGAGGACGGGTCCGTTCAGCTGGCCGACCACTATCAGCAGAAC
ACACCAATTGGAGACGGCCCCGTCCTGCTCCCCGATAACCATTACCTTTCGACACAGTCGGCGCTGTCGAAGGACCCGAACGA
AAAGCGGGACCACATGGTGCTCCTGGAGTTCGTCACGGCGGCCGGGATCACGCACGGAATGGACGAACTCTACAAGTAG |

FIG. 11

```
ATGCGTAACGAATCTATCCGTCGTCGTGAAGCGTTAATTGGTATCGCTGCAGCAGTTGCAGCAACTGGTT
CACTCGCTCAAAGTAACCAACCACTGAAAATCGTTGTGCCTTTTCTGCAGGTGGTACAGCGGACGTATT
ACCACGTCTTGTCGCTGAAAAAATCCGTGCCGATTATGCTGGTGGTGTTATCATCGAAAACAAACCAGGT
GCAGGTGGTAATATTGGTGCAGATCTAGTTTTCCGTGCTCCACCAGACGGTATGACGGTTTTAGCTTCAC
CACCTGGTCCTATCGCTATTAATCACAATCTTTATCAAAAATTATCTTTCGATCCTACTCGTTGGGTACC
AGTAACCATTCTGGCAACAGTTCCTAACGTACTTGTAATTAACCCAAAACTACCTGTTAAAAGCcttGGC
GAATTTATCGCATACGCAAAAGCAAATCCAAAGAAAGTAACCGTAGCGACTCAAGGTGACGGTTCTACTT
CACACCTTACAGCAGCAATGTTTATGCAATTAACTGGTACAGAACTAACTGTTATCCCATACAAAGGTAC
AGCACCAGCTTTAATCGATCTTATTGGTGGTAATGTAGACGTGTTTTTCGATAATATCAGCTCTTCTGCA
ACTTATCACCAAGCAGGAAAAGTTCGTATTCTTGCAGTTGCTGATGAACAACGTTCACAAATTCTTCCAC
AAGTTCCAACGTTCGCAGAACAACAGTGGCCAGCAATGCAAGCTGTGACATTTTTCTCAGTAGTGGCACC
TCCTGGTACATCAGCAGAAATCGCACAAAAACTTCAAAAACAGATGGCTCTTGCCCTTTCTTCGAACGAT
ATTCGTAAGCACTTCCAGGAACAAGGTGCTGTGCCATGTGGTTGGGATCCAAGTAAAACTGCTCAATTTA
TTCGTCAGGAAACCGAAAAATGGAAGAAAGTACTCAAAGCAGCAAACGTAAAACTTTAA
```

FIG. 12

ATGCAGGAAAGCATTATTCAATGGCATGGTGCGACCAACACACGCGTTCCATTTGGTATCTATACAGATA
CCGCAAATGCTGACCAAGAACAACAGCGTATTTACCGTGGCGAAGTATGGAATTACCTTTGTTTGGAATC
AGAAATCCCAGGAGCGGGTGATTTTCGTACCACATTTGCGGGTGAAACACCTATTGTCGTAGTTCGTGAT
GCTGATCAAGAAATTTATGCTTTCGAAAATCGTTGTGCTCACCGTGGTGCTTTAATTGCATTAGAAAAGA
GCGGTCGTACTGATTCTTTTCAATGTGTTTATCATGCATGGTCATATAACCGTCAGGGTGACCTTACGGG
TGTGGCTTTCGAAAAGGCGTAAAAGGTCAGGGTGGTATGCCAGCTAGTTTCTGTAAAGAAGAACATGGT
CCACGTAAACTTCGCGTAGCAGTTTTCTGCGGCTTGGTTTTCGGTTCTTTTTCTGAAGACGTTCCAAGTA
TTGAAGATTATTTGGGTCCGGAAATTTGTGAACGTATCGAACGTGTTCTCCATAAGCCTGTAGAAGTTAT
CGGTCGTTTTACTCAGAAATTACCTAATAACTGGAAACTTTATTTTGAAAATGTAAAAGATAGCTACCAT
GCATCTCTTTTACACATGTTTTTCACAACTTTCGAACTGAACCGTTTATCTCAGAAAGGCGGTGTTATTG
TGGATGAGTCTGGCGGCCATCATGTATCCTATAGTATGATTGATCGTGGGGCCAAGGATGATTCATATAA
AGATCAAGCTATTCGTTCTGACAATGAACGTTATCGTTTGAAAGATCCTAGCTTACTAGAAGGTTTTGAA
GAATTCGAAGATGGTGTAACGCTTCAAATTCTTAGCGTATTCCCAGGGTTTGTTTTGCAACAAATCCAAA
ACAGTATTGCAGTGCGTCAGTTATTGCCAAAAAGTATTTCTAGTTCTGAATTGAACTGGACTTATTTAGG
TTATGCCGATGATAGCGCAGAACAACGTAAAGTTCGTCTTAAACAAGCTAATCTGATTGGACCTGCTGGA
TTCATTTCAATGGAAGATGGTGCAGTCGGCGGTTTCGTGCAGCGTGGTATTGCAGGCGCTGCTAACCTTG
ATGCAGTAATCGAAATGGGCGGTGATCATGAAGGCAGCTCTGAAGGTCGCGCTACTGAAACTtcaGTACG
TGGCTTTTGGAAAGCATATCGTAAACATATGGGACAAGAAATGCAGGCATGA

FIG. 13

ATGATCAATGAAATACAGATCGCAGCATTTAATGCAGCATATGCAAAAACTATTGACTCTGATGCTATGG
AACAATGGCCTACCTTTTTTACTAAAGATTGCCATTATTGTGTAACGAATGTAGATAATCATGATGAGGG
TTTAGCTGCTGGTATAGTTTGGGCAGATTCACAGGACATGTTGACTGATCGTATCTCAGCTTTGCGTGAA
GCGAACATTTACGAACGTCACCGCTATCGTCACATCTTAGGTCTGCCATCAATTCAATCAGGTGATGCAA
CGCAGGCATCAGCTAGCACACCTTTCATGGTTCTTCGTATCATGCATACTGGCGAAACGGAGGTTTTCGC
ATCGGGTGAATATCTCGATAAATTCACTACTATTGATGGTAAATTGCGCCTTCAGGAACGTATTGCTGTT
TGTGACTCTACAGTAACCGATACCTTAATGGCATTGCCATTATGA

FIG. 14

ATGAACGCAATTGTTCACCGCCGTCTTGCACTTGCAATTGGTGATCCACATGGTATTGGTCCTGAAATCG
CATTGAAAGCTCTTCAACAGCTTTCGGTAACTGAACGTAGCTTAATTAAAGTATACGGTCCGTGGTCTGC
ACTTGAACAAGCAGCACGCGTTTGCGAAATGGAACCACTCTTACAAGATATCGTACACGAAGAAGCAGGT
ACCTTGACCCAACCAGTACAGTGGGGTGAAATTACACCACAAGCTGGTCTTAGTACAGTACAATCAGCTA
CTGCTGCGATCCGTGCATGTGAAAATGGTGAGGTAGATGCAGTTATTGCGTGTCCACACCATGAAACTGC
AATCCACCGTGCTGGTATCGCCTTCTCTGGTTATCCAAGCcttTTAGCGAATGTGTTGGGTATGAACGAA
GATCAAGTTTTTCTTATGTTGGTTGGTGCTGGTCTTCGTATCGTTCATGTGACTCTACACGAATCTGTAC
GTTCTGCACTTGAACGTCTTTCTCCACAACTTGTTGTAAATGCAGCACAAGCAGCAGTTCAAACCTGTAC
ATTGCTTGGTGTTCCTAAACCGAAAGTGGCAGTGTTCGGCATTAACCCACATGCATCAGAAGGTCAACTT
TTCGGCTTGGAAGATAGCCAAATTACCGTTCCAGCAGTTGAAACCCTTCGTAAACGTGGTCTAGCTGTTG
ATGGTCCAATGGGTGCGGATATGGTACTGGCACAACGTAAACATGATTTATATGTTGCGATGCTTCATGA
TCAGGGTCATATACCAATTAAACTTCTTGCACCAAATGGTGCGAGTGCTCTCTCAATCGGTGGTCGTGTT
GTATTGTCATCAGTTGGACACGGCAGCGCAATGGACATCGCTGGCCGTGGCGTAGCTGATGCCACTGC
TCTTTTACGTACCATTGCTCTTCTTGGCGCTCAGCCAGTTTGA

FIG. 15

```
ATGAACCATCAAATCCACATCCATGACTCAGATATTGCATTTCCATGTGCACCTGGTCAATCAGTTTTGG
ATGCGGCCTTACAAGCAGGTATCGAATTGCCTTATAGCTGCCGTAAAGGTTCATGTGGGAATTGTGCAAG
TACTCTTTTAGATGGTAATATTGCATCTTTCAACGGTATGGCTGTTCGTAATGAATTATGTGCGTCTGAA
CAAGTGTTATTGTGTGGTTGCACGGCGGCATCTGATATACGTATTCATCCTTCTTCTTTCCGTCGTCTTG
ACCCAGAAGCTCGTAAACGTTTCACTGCTAAGGTATATTCAAATACTCTTGCTGCTCCAGATGTATCTCT
TCTCCGTCTCCGTTTACCTGTTGGTAAACGTGCTAAATTTGAAGCTGGTCAATATTTACTAATCCACTTA
GATGACGGTGAGAGCCGTAGCTACAGCATGGCAAATCCACCACATGAATCTGATGGTATCACCTTACATG
TTCGTCATGTTCCAGGTGGGCGTTTTAGTACTATTGTACAACAATTGAAATCAGGAGATACTTTGGACAT
TGAATTACCTTTTGGTTCTATTGCGCTTAAACCTGATGACGCTCGTCCTCTGATCTGTGTAGCTGGTGGT
ACCGGCTTTGCTCCAATCAAATCCGTTTTAGACGATCTCGCGAAACGTAAAGTACAGCGCGATATCACAC
TTATCTGGGGCGCACGCAATCCATCTGGCTTATATCTTCCATCAGCTATCGATAAGTGGCGTAAGGTATG
GCCACAATTCCGTTACATCGCCGCTATCACTGATCTTGGGGATATGCCAGCTGATGCACACGCTGGTCGT
GTGGACGACGCATTACGTACTCATTTTGGTAATCTGCATGATCATGTTGTTCATTGTGTGGTTCGCCTG
CtCTAGTTCAAAGTGTCCGTACAGCCGCCTCGGACATGGGTCTACTAGCGCAAGATTTCCATGCAGATGT
ATTTGCAACTGGTCCTACAGGTCACCACTAG
```

FIG. 16

```
ATGAAAATTAAAAGTCAAAAAGATTTTTTTTCTGGTTTGATGTTCCTTGCAGTTGGTTTAGCATTTGCAA
TTGGTGCTTCAAATTATACTATTGGTACTGGTGCTCGTATGGGTCCAGGTTATTTCCCTCTTATACTTGG
TGTACTGATGGCGATTCTAGGTGCAGCTATCTGTGTTGGTGGTCTTACTAAAGGTCCAGAGGGTGGTGAT
AAAATTGGTAAATGGGCATGGCGTCAAGTTTTTTTTATCTTGGCAGCAAATTTTGCATTCGGCATTTTGT
TAGTGGGTGTACCAGCAGTTGGTATTCCACAATTTGGTCTTATTATCGCAATTTATGCGTTAGTCTTCAT
CGCGTCTTTGGGTGGCCACTCTTTCAACTTCAAAGAAACCGCGATCCTTGCAACGGTGCTTGCAGTTGGT
TCTTACTTCGCTTTTGTTTGGGCATTAAACTTACAATTCCCAGTATGGCCATCATTTATCGCGGGTTAA
```

FIG. 17

```
ATGGATCTTATTCAAAACTTAAGTACCGGCTTCGGTGTGGCTTTCACTTTCCAAAATTTGATTTATTGTT
TCGTTGGTTGTCTTTTAGGTACTTTAATTGGCGTACTTCCAGGCATTGGTCCAGTTGCTACAATTGCAAT
GTTATTGCCTGCAACCTATGCTTTACCACCAGTGGCTGCATTGATTATGTTGGCTGGTATCTACTATGGT
GCGCAGTATGGTGGTAGTACTACTGCTATTTTGGTAAATCTTCCGGGTGAATCTTCTTCTGTAGTCACCG
TTATCGATGGTTACCAAATGGCTCGTAAAGGTCGTGCAGGTCCAGCGCTTGCTGCTGCTGGTATTGGTTC
TTTTTTCGCAGGTTGTGTTGGTACAGTGATCTTAGCGGCTTTCGCTCCACCTCTCACGGAAGTTGCATTC
AAGTTTGGACCTGCAGAGTATTTTTCTTTAATGACATTGGGTCTAATTGGTGCAGTTGTCCTTGCTTCAG
GCTCTTTGCTCAAAGCAATTGCAATGATCGTACTCGGTCTTTTGCTTGGCATGGTTGGTACGGACGTAAA
TTCAGGTGTAGCGCGTTACTCATTTGACATTCCAGAGCTAACAGATGGTATTGATTTGTTGTGATCGCA
ATGGGTGTTTTTGGTTACGGTGAAATTATTGCAAATCTTTCAAAGCCTGATGATGAACGTGAGGTTTTTG
CAGCGAAAGTGACTGGTCTTCTTCCAACAAGTGAAGACTTCAAACGTATGTTGCCAGCAATGTTGCGTGG
TACAGCATTAGGTTCAGCTTTAGGAATTTTGCCAGGTGGTGGTGCTATGTTGAGTGCATTTGCAGCTTAT
ACAATTGAAAAAAAAACCAAATTAAAACCTGGTGAAGTACCATTTGGTCAGGGCAATATTCGTGGCGTTT
GCGCTCCGGAATCAGCAAACAACGCTGGTAGTCAAACATCTTTCATTCCACTGTTAACATTGGGCATTCC
TCCAAACGCCGTAATGGCTCTCATGGTAGGCGCAATGACTATTCACAACATTCAACCAGGACCACAAGTG
ATGACATCTAACCCTGAACTATTTTGGGGTCTTATTGCAAGCATGTGGATTGGTAATTTGATGTTAATTA
TTTTGAACCTACCACTTATCGGTGTGTGGATCAAGTTGCTTACAGTACCATATCGTTGGTTGTTTCCATC
TATCGTATTATTTTGTGCAATTGGTGTGTATGGTACTAATAACAACGTTTGGGATGTTTGGATGGTAGGT
ATTTTTGGTTTCATTGGTTATGTATTCCACAAGTTAGGGACTGAACCTGCTCCTTTGTTGTTGGGTTTCA
TTTTAGGTCCAATGATGGAAGAAACCTTCGCCGTGCTCTATTGCTATCGCGTGGCGACTGGTCTGTATT
TGTTACGCGTCCAATTAGTGCATGCTTACTGGCAGCGGCTGTTGTGCTTCTTGTAATCGTTCTTATGCCT
GCAGTTAAGAATAAACGTGAAGAGGCCTTTGTAGAAGATTGA
```

FIG. 18

*GTTTAAACCAAATTACGCAGCTCATTCGCAGTATTGCGTAATAAAGGTAAAACTTGATCGATAAGATACT*
*GTGGCTGCACCCGATTGGTTTGTGACATACAATTAAGTGCTGCAATGGTAAGCCCCTGTGCGTTTAAAAC*
*GGGTACCGCAATCGCAATCAGACCCAGTTCATGTTCCTCAGTAGACAAACAGTAGTCCGATTGCCGAACA*
*GCATCTAATGTTTCTAAAAAGTATGTTCATCGGTAATGGTATAAGGCGTGAGGCGCTTCAGACCATATT*
*TTTCAATCCATTCAATTTGTACTTCACGATCCAGAACAGAAAGTAATACTTTACCGGTAGAGGTGGCGTG*
*GGCAGGCAAACGATTACCCAAATGCATCCCATAGGGGCTCACGCGAAGATTATCTTGCTGGGGTAAATAA*
*CTACGCGCAACAGGTACAACTTCATGCTCATCGAGCACCACAATTGAAAAGGTGAGGCTGGTTTGAGCAC*
*ACAGTAGATTTAAAAATGACTGTGCCACTTTGGGTAAATGTGCCGAGCTTAAATAAGAACTAGAAAAACG*
*TAAAACACGATGTGTAAGCCAAAAATAGTGCTCATCGGTATCTAAATAACCCAAAAATTTAAGTGTCTTT*
*AAATAACGCCGTGCAGCTGTTCTGCTTATACCAGTACGCTCTGCAACCTGTGTCACGTTCAGTCGTTGTC*
*TGTCAATTCCAAATGCTTCTAAAAGCGCTAAGCCTTTGGCCAAGCCTGCAATGTAATCTTCCGTACGTAT*
*TTCTTCACTTGAATGGGGATGTGCAAGGTATTGGTGATGTTGTTCCATAACATTCAAATCCAAAATGGTT*
*TTGTCCGATCATCGGACAGTTGTAATGCTAATCGGATAATTTTGAGCCTTGATTATAGATGTCTTTTTAA*
*TGAGGCGGTACTTTAAAAATAGAAAATAGCAAGGATGATGTTATGCAAACTATGAAAACCAAAGTTGCAA*
*TTATTGGTTCTGGCCCAGCGGGATTACTACTCGGTCAACTGCTTTACAAAGCTGGAATTGAACACGTTAT*
*TGTGGAACAGCGAAGTGCCGATTACGTTGCATCACGCATTCGTGCAGGAATTTTAGAGCAAGTATCGGTC*
*GATTTACTCGAGCAAGCTGGAGTTGATCAGAACCTCAAAGAAAAGGATTGCCACATTCGGGCATTGAAA*
*TTCTGACCAATGGCCAAAAATTCCGTGTCGATTTATCGGCATTGACTCAAGGTAAACAAGTCACGGTATA*
*TGGGCAGACCGAAGTTACTAAAGATTTAATGCAAGCACGTGAGCAGGCTGGTCTTTGCTCATTTTATGAA*
*TCGAATGATGTTCAAATTCATGATTTTATAATGCGCCAAAAGTGACTTTTGAATCCAACGGAACTCACT*
*ATCAAATCGAATGTGATTTCATTGCAGGATGTGATGGTTATCATGGCGTGTGCCGTGCTAGTGTGCCTCA*
*AGATAAAATTAAAACCTTTGAAAAGGTCTATCCATTTGGTTGGTTAGGTGTACTTGCCGATGTGCCGCCT*
*GTGGCAGACGAGTTAATTTATGTTCAATCAGAGCGTGGTTTTGCACTGTGTAGCATGCGCTCAGAAACGC*
*GAAGCCGATATTACATTCAAGTTCCTTTAACCGATCACGTAGAAAACTGGTCGGATGATCAATTTTGGGA*
*AGAGCTTAAGAATCGCCTCGACCCTGAAAGCTGCGAAAAACTCGTTACAGGCCCTTCAATTGAGAAAAGT*
*ATTGCACCTTTGCGGAGCTTTGTCACAGAACCGATGCGATTTGGAAAATTATTCTTAGCTGGTGATGCCG*
*CACATATTGTTCCACCAACGGGTGCCAAAGGATTGAATCTTGCAGCTTCAGATATTGCATATTTGTCGAG*
*TGCGCTCATTGAATTTTACACGCAAGGATCTGAGCAAGGTATAGATCAATACTCAGAAAAATGCTTGCAA*
*CGTGTATGGAAAGCAGAGCGTTTTTCATGGTGGATGACCCATTTGTTACATCGCTTTGAAACCGAAAGCG*
*AGTTTGATCATAAAATTAAACAAGCAGAATTGAGCTATATCTTAGGTTCTACGGCAGGTCAGACCACACT*
*CGCTGAAAACTATGTGGGTTTACCCTATGAAATCAAATCCCTTGACTATTTAAAACATGCCAGCTAACCA*
GACATCAAATAAAACGAAAGGCTCAGTCGAAAGACTGGGCCTTTCGTTTTATCTGTTGTTTGTCGGTGAA
CGCTCTCATTAATTAATCCAGAGGCATGAGCTGTTGACAATTAATCATCGGCTCGTATAATGTGTGGAAT
TGTGAGCGGATAACAATTTCACACAGGAGAGTCTATATATGCGTAACGAATCTATCCGTCGTCGTGAAGC
GTTAATTGGTATCGCTGCAGCAGTTGCAGCAACTGGTTCACTCGCTCAAAGTAACCAACCACTGAAAATC
GTTGTGCCTTTTCTGCAGGTGGTACAGCGGACGTATTACCACGTCTTGTCGCTGAAAAATCCGTGCCG
ATTATGCTGGTGGTGTTATCATCGAAAACAAACCAGGTGCAGGTGGTAATATTGGTGCAGATCTAGTTTT
CCGTGCTCCACCAGACGGTATGACGGTTTTAGCTTCACCACCTGGTCCTATCGCTATTAATCACAATCTT
TATCAAAAATTATCTTTCGATCCTACTCGTTGGGTACCAGTAACCATTCTGGCAACAGTTCCTAACGTAC
TTGTAATTAACCCAAAACTACCTGTTAAAAGCCTTGGCGAATTTATCGCATACGCAAAAGCAAATCCAAA
GAAAGTAACCGTAGCGACTCAAGGTGACGGTTCTACTTCACACCTTACAGCAGCAATGTTTATGCAATTA
ACTGGTACAGAACTAACTGTTATCCCATACAAAGGTACAGCACCAGCTTTAATCGATCTTATTGGTGGTA
ATGTAGACGTGTTTTTCGATAATATCAGCTCTTCTGCAACTTATCACCAAGCAGGAAAAGTTCGTATTCT
TGCAGTTGCTGATGAACAACGTTCACAAATTCTTCCACAAGTTCCAACGTTCGCAGAACAACAGTGGCCA
GCAATGCAAGCTGTGACATTTTCTCAGTAGTGGCACCTCCTGGTACATCAGCAGAAATCGCACAAAAAC

FIG. 19

```
TTCAAAAACAGATGGCTCTTGCCCTTTCTTCGAACGATATTCGTAAGCACTTCCAGGAACAAGGTGCTGT
GCCATGTGGTTGGGATCCAAGTAAAACTGCTCAATTTATTCGTCAGGAAACCGAAAAATGGAAGAAAGTA
CTCAAAGCAGCAAACGTAAAACTTTAAGAGAGGAAAGCAATGCAGGAAAGCATTATTCAATGGCATGGTG
CGACCAACACACGCGTTCCATTTGGTATCTATACAGATACCGCAAATGCTGACCAAGAACAACAGCGTAT
TTACCGTGGCGAAGTATGGAATTACCTTTGTTTGGAATCAGAAATCCCAGGAGCGGGTGATTTTCGTACC
ACATTTGCGGGTGAAACACCTATTGTCGTAGTTCGTGATGCTGATCAAGAAATTTATGCTTTCGAAAATC
GTTGTGCTCACCGTGGTGCTTTAATTGCATTAGAAAAGAGCGGTCGTACTGATTCTTTTCAATGTGTTTA
TCATGCATGGTCATATAACCGTCAGGGTGACCTTACGGGTGTGGCTTTCGAAAAAGGCGTAAAAGGTCAG
GGTGGTATGCCAGCTAGTTTCTGTAAAGAAGAACATGGTCCACGTAAACTTCGCGTAGCAGTTTTCTGCG
GCTTGGTTTTCGGTTCTTTTTCTGAAGACGTTCCAAGTATTGAAGATTATTTGGGTCCGGAAATTTGTGA
ACGTATCGAACGTGTTCTCCATAAGCCTGTAGAAGTTATCGGTCGTTTTACTCAGAAATTACCTAATAAC
TGGAAACTTTATTTTGAAAATGTAAAAGATAGCTACCATGCATCTCTTTTACACATGTTTTTCACAACTT
TCGAACTGAACCGTTTATCTCAGAAAGGCGGTGTTATTGTGGATGAGTCTGGCGGCCATCATGTATCCTA
TAGTATGATTGATCGTGGGGCCAAGGATGATTCATATAAAGATCAAGCTATTCGTTCTGACAATGAACGT
TATCGTTTGAAAGATCCTAGCTTACTAGAAGGTTTTGAAGAATTCGAAGATGGTGTAACGCTTCAAATTC
TTAGCGTATTCCCAGGGTTTGTTTTGCAACAAATCCAAAACAGTATTGCAGTGCGTCAGTTATTGCCAAA
AAGTATTTCTAGTTCTGAATTGAACTGGACTTATTTAGGTTATGCCGATGATAGCGCAGAACAACGTAAA
GTTCGTCTTAAACAAGCTAATCTGATTGGACCTGCTGGATTCATTTCAATGGAAGATGGTGCAGTCGGCG
GTTTCGTGCAGCGTGGTATTGCAGGCGCTGCTAACCTTGATGCAGTAATCGAAATGGGCGGTGATCATGA
AGGCAGCTCTGAAGGTCGCGCTACTGAAACTTCAGTACGTGGCTTTTGGAAAGCATATCGTAAACATATG
GGACAAGAAATGCAGGCATGAGGAGTCCCTAAACAATGATCAATGAAATACAGATCGCAGCATTTAATGC
AGCATATGCAAAAACTATTGACTCTGATGCTATGGAACAATGGCCTACCTTTTTTACTAAAGATTGCCAT
TATTGTGTAACGAATGTAGATAATCATGATGAGGGTTTAGCTGCTGGTATAGTTTGGGCAGATTCACAGG
ACATGTTGACTGATCGTATCTCAGCTTTGCGTGAAGCGAACATTTACGAACGTCACCGCTATCGTCACAT
CTTAGGTCTGCCATCAATTCAATCAGGTGATGCAACGCAGGCATCAGCTAGCACACCTTTCATGGTTCTT
CGTATCATGCATACTGGCGAAACGGAGGTTTTCGCATCGGGTGAATATCTCGATAAATTCACTACTATTG
ATGGTAAATTGCGCCTTCAGGAACGTATTGCTGTTTGTGACTCTACAGTAACCGATACCTTAATGGCATT
GCCATTATGAAAGGAGGTAACAATGAACGCAATTGTTCACCGCCGTCTTGCACTTGCAATTGGTGATCCA
CATGGTATTGGTCCTGAAATCGCATTGAAAGCTCTTCAACAGCTTTCGGTAACTGAACGTAGCTTAATTA
AAGTATACGGTCCGTGGTCTGCACTTGAACAAGCAGCACGCGTTTGCGAAATGGAACCACTCTTACAAGA
TATCGTACACGAAGAAGCAGGTACCTTGACCCAACCAGTACAGTGGGGTGAAATTACACCACAAGCTGGT
CTTAGTACAGTACAATCAGCTACTGCTGCGATCCGTGCATGTGAAAATGGTGAGGTAGATGCAGTTATTG
CGTGTCCACACCATGAAACTGCAATCCACCGTGCTGGTATCGCCTTCTCTGGTTATCCAAGCCTTTTAGC
GAATGTGTTGGGTATGAACGAAGATCAAGTTTTTCTTATGTTGGTTGGTGCTGGTCTTCGTATCGTTCAT
GTGACTCTACACGAATCTGTACGTTCTGCACTTGAACGTCTTTCTCCACAACTTGTTGTAAATGCAGCAC
AAGCAGCAGTTCAAACCTGTACATTGCTTGGTGTTCCTAAACCGAAAGTGGCAGTGTTCGGCATTAACCC
ACATGCATCAGAAGGTCAACTTTTCGGCTTGGAAGATAGCCAAATTACCGTTCCAGCAGTTGAAACCCTT
CGTAAACGTGGTCTAGCTGTTGATGGTCCAATGGGTGCGGATATGGTACTGGCACAACGTAAACATGATT
TATATGTTGCGATGCTTCATGATCAGGGTCATATACCAATTAAACTTCTTGCACCAAATGGTGCGAGTGC
TCTCTCAATCGGTGGTCGTGTTGTATTGTCATCAGTTGGACACGGCAGCGCAATGGACATCGCTGGCCGT
GGCGTAGCTGATGCCACTGCTCTTTTACGTACCATTGCTCTTCTTGGCGCTCAGCCAGTTTGAGGTCCCT
CCCAAATGAACCATCAAATCCACATCCATGACTCAGATATTGCATTTCCATGTGCACCTGGTCAATCAGT
TTTGGATGCGGCCTTACAAGCAGGTATCGAATTGCCTTATAGCTGCCGTAAAGGTTCATGTGGGAATTGT
```

FIG. 19 (continued)

```
GCAAGTACTCTTTTAGATGGTAATATTGCATCTTTCAACGGTATGGCTGTTCGTAATGAATTATGTGCGT
CTGAACAAGTGTTATTGTGTGGTTGCACGGCGGCATCTGATATACGTATTCATCCTTCTTCTTTCCGTCG
TCTTGACCCAGAAGCTCGTAAACGTTTCACTGCTAAGGTATATTCAAATACTCTTGCTGCTCCAGATGTA
TCTCTTCTCCGTCTCCGTTTACCTGTTGGTAAACGTGCTAAATTTGAAGCTGGTCAATATTTACTAATCC
ACTTAGATGACGGTGAGAGCCGTAGCTACAGCATGGCAAATCCACCACATGAATCTGATGGTATCACCTT
ACATGTTCGTCATGTTCCAGGTGGGCGTTTTAGTACTATTGTACAACAATTGAAATCAGGAGATACTTTG
GACATTGAATTACCTTTTGGTTCTATTGCGCTTAAACCTGATGACGCTCGTCCTCTGATCTGTGTAGCTG
GTGGTACCGGCTTTGCTCCAATCAAATCCGTTTTAGACGATCTCGCGAAACGTAAAGTACAGCGCGATAT
CACACTTATCTGGGGCGCACGCAATCCATCTGGCTTATATCTTCCATCAGCTATCGATAAGTGGCGTAAG
GTATGGCCACAATTCCGTTACATCGCCGCTATCACTGATCTTGGGGATATGCCAGCTGATGCACACGCTG
GTCGTGTGGACGACGCATTACGTACTCATTTTGGTAATCTGCATGATCATGTTGTTCATTGTTGTGGTTC
GCCTGCTCTAGTTCAAAGTGTCCGTACAGCCGCCTCGGACATGGGTCTACTAGCGCAAGATTTCCATGCA
GATGTATTTGCAACTGGTCCTACAGGTCACCACTAGGGT
```
*TAAAACAAAAGAGAGCGATTAGTCGCTCTC*
*TTTTTTATCTCGGCTGTGTTTATTTACAAGTGAAATTCTCGGCTTTTTCACTGTCACCTGTACCGTTATA*
*ACGTGCGATTTTTGGATATGGACATAGTGGTCGAGTTCGATTGGCCGACCAGCTCGATGGTAACTCGCTA*
*TTGATTTCGCCACTTGCATTACCGACACCGCGTGCAGAAGCGAGAATTTGATCTGGTGCTTGACCATATT*
*CTACCCAGTTCACCAAAGCAGTAAGTGCATCAAACTGGTCGGTCGCAAGCCCACCCCGCGAATGATTCAT*
*TCCCGGAACGCGATAAAAACGAGCAAAACTTTGTGCGTCACCCAAACTGCTGCTCTTGTATTTTGCCATC*
*AGTTTATCGTACCAGTTTTGTGTGTCATCTACCGAAAATACGCCATCTGCTGTGCCTTGCACCACAATCA*
*TTTTACCGCCATGCAAGCGTAATTTATCCAGATTGAGCTCATCTGGCGGATCATAAATGACATCGCGCT*
*TTCTGAATAGGTCGAATTGGTTGCAGAAAGTTTTGGGTAATCTGTATCAAAATTATAGTTAAAGGCAAAT*
*TTTCGTGAATTTTGCACAATTGTTGGATCTGGTGGTACCTGAAATATAATGCCTACCGCTACCGGGTCGC*
*GTGCCGTACCCACAGAAGAAACAAATTTCCAGCTTGCCCAATTGCTGCCAAGTAATCCCGGATCGTAAGG*
*CTGGGTCGCATACAATGCTTCGCCAGATGAATTGACAGGGCCGCGGTAAATATTAGCCACGACATCGATC*
*TGGTCTTTACTCAAACAGCTTCCATCACGTGAACCCGAGCAGACAGGCACATCTTTATGAATATCAAAGG*
*CGGTTCGACAGGCTTCAACGTCTTGTACCATACCATCTGCTACACCATCGAGTGCATCACAGCGTGTTAA*
*AATCGCATTGGCAAGTACGTTACGTTCTGCATAGGTGAGTGCAGTGCTTAAATCATTTTCATCGGTGGCA*
*ACACGACGTAATTGCTGCGCCGTGTATAGCTGTGCCGCTGCTGCACGTGGTAGATGAAATCCGGGTGTGC*
*TTGCCAAGATGCCATCGTACTGATCGCCTAGGCGTGTTGCAGCCATCATGGCATGTCGACCGCCGTTAGA*
*CGTACCTCCTGCATAAGATCGATCTGGCAATTTACCGTAAGCTGTTTAATCAGATCTTTGGCCATAGGC*
*GTTAACTTTGTAATAGCACCATAACCATAGTTGATGCGAGCTTGCGGATCTAAACCAAAAGAGGATTTT*
*GTGCAGATGAATGTCCGGCATCGGATGAAATTACCGCGAATCCGTCTTTTAAAGCATTGCTTAACATCCC*
*GCCGCTGCCCACTTGTCCGGTCGCTGTGGCGATGTTGCCGTCGGTACCGCCATTTCCTTGATATAGAAAA*
*CGTCCGTTCCAGCTCACCGGAAGTCGCATTTCAAAGCCAATCTGATAGGTTTGACCATCGATTGGGCTAA*
*TACGTTGCTCCATATAACCTTTGACCAAACAATGCGCCGGAATATTTTCCCCACGACGGTCAGAGCGCC*
*TGCATTTTGTAAAGTTGCACTTTCAACTACGGTGGTATCAAATTTGAAACCGCTTAAATCTGTACAACTG*
*CCTTTGAGCTGAGCACCTACTGCTGGGCTTAATTGTGGAATACTTTGGCTCGACTGTGCCGTATCATGAT*
*CGTTATTGTCATTACATGCAGCTACACTGATGCAGACGCCGAGCAATGCAGCATGTTTAAAAAAATGTTG*
*AGGTTTTTTCATTGCAATATCCTTATGCCT*

FIG. 19 (continued)

*GTTTAAACCAAATTACGCAGCTCATTCGCAGTATTGCGTAATAAAGGTAAAACTTGATCGATAAGATACT*
*GTGGCTGCACCCGATTGGTTTGTGACATACAATTAAGTGCTGCAATGGTAAGCCCCTGTGCGTTTAAAAC*
*GGGTACCGCAATCGCAATCAGACCCAGTTCATGTTCCTCAGTAGACAAACAGTAGTCCGATTGCCGAACA*
*GCATCTAATGTTTCTAAAAAGTATGTTCATCGGTAATGGTATAAGGCGTGAGGCGCTTCAGACCATATT*
*TTTCAATCCATTCAATTTGTACTTCACGATCCAGAACAGAAAGTAATACTTTACCGGTAGAGGTGGCGTG*
*GGCAGGCAAACGATTACCCAAATGCATCCCATAGGGGCTCACGCGAAGATTATCTTGCTGGGGTAAATAA*
*CTACGCGCAACAGGTACAACTTCATGCTCATCGAGCACCACAATTGAAAAGGTGAGGCTGGTTTGAGCAC*
*ACAGTAGATTTAAAAATGACTGTGCCACTTTGGGTAAATGTGCCGAGCTTAAATAAGAACTAGAAAAACG*
*TAAAACACGATGTGTAAGCCAAAAATAGTGCTCATCGGTATCTAAATAACCCAAAAATTTAAGTGTCTTT*
*AAATAACGCCGTGCAGCTGTTCTGCTTATACCAGTACGCTCTGCAACCTGTGTCACGTTCAGTCGTTGTC*
*TGTCAATTCCAAATGCTTCTAAAAGCGCTAAGCCTTTGGCCAAGCCTGCAATGTAATCTTCCGTACGTAT*
*TTCTTCACTTGAATGGGGATGTGCAAGGTATTGGTGATGTTGTTCCATAACATTCAAATCCAAAATGGTT*
*TTGTCCGATCATCGGACAGTTGTAATGCTAATCGGATAATTTTGAGCCTTGATTATAGATGTCTTTTTAA*
*TGAGGCGGTACTTTAAAAATAGAAAATAGCAAGGATGATGTTATGCAAACTATGAAAACCAAAGTTGCAA*
*TTATTGGTTCTGGCCCAGCGGGATTACTACTCGGTCAACTGCTTTACAAAGCTGGAATTGAACACGTTAT*
*TGTGGAACAGCGAAGTGCCGATTACGTTGCATCACGCATTCGTGCAGGAATTTTAGAGCAAGTATCGGTC*
*GATTTACTCGAGCAAGCTGGAGTTGATCAGAACCTCAAAGAAAAGGATTGCCACATTCGGGCATTGAAA*
*TTCTGACCAATGGCCAAAAATTCCGTGTCGATTTATCGGCATTGACTCAAGGTAAACAAGTCACGGTATA*
*TGGGCAGACCGAAGTTACTAAAGATTTAATGCAAGCACGTGAGCAGGCTGGTCTTTGCTCATTTTATGAA*
*TCGAATGATGTTCAAATTCATGATTTTATAATGCGCCAAAAGTGACTTTTGAATCCAACGGAACTCACT*
*ATCAAATCGAATGTGATTTCATTGCAGGATGTGATGGTTATCATGGCGTGTGCCGTGCTAGTGTGCCTCA*
*AGATAAAATTAAAACCTTTGAAAAGGTCTATCCATTTGGTTGGTTAGGTGTACTTGCCGATGTGCCGCCT*
*GTGGCAGACGAGTTAATTTATGTTCAATCAGAGCGTGGTTTTGCACTGTGTAGCATGCGCTCAGAAACGC*
*GAAGCCGATATTACATTCAAGTTCCTTTAACCGATCACGTAGAAAACTGGTCGGATGATCAATTTTGGGA*
*AGAGCTTAAGAATCGCCTCGACCCTGAAAGCTGCGAAAAACTCGTTACAGGCCCTTCAATTGAGAAAAGT*
*ATTGCACCTTTGCGGAGCTTTGTCACAGAACCGATGCGATTTGGAAAATTATTCTTAGCTGGTGATGCCG*
*CACATATTGTTCCACCAACGGGTGCCAAAGGATTGAATCTTGCAGCTTCAGATATTGCATATTTGTCGAG*
*TGCGCTCATTGAATTTTACACGCAAGGATCTGAGCAAGGTATAGATCAATACTCAGAAAAATGCTTGCAA*
*CGTGTATGGAAAGCAGAGCGTTTTTCATGGTGGATGACCCATTTGTTACATCGCTTTGAAACCGAAAGCG*
*AGTTTGATCATAAAATTAAACAAGCAGAATTGAGCTATATCTTAGGTTCTACGGCAGGTCAGACCACACT*
*CGCTGAAAACTATGTGGGTTTACCCTATGAAATCAAATCCCTTGACTATTTAAAACATGCCAGCTAACCA*
GACATCAAATAAAACGAAAGGCTCAGTCGAAAGACTGGGCCTTTCGTTTTATCTGTTGTTTGTCGGTGAA
CGCTCTCATTAATTAATCCAGAGGCATGAGCTGTTGACAATTAATCATCGGCTCGTATAATGTGTGGAAT
TGTGAGCGGATAACAATTTCACACAGGAGAGTCTATAT<u>ATGCGTAACGAATCTATCCGTCGTCGTGAAGC</u>
<u>GTTAATTGGTATCGCTGCAGCAGTTGCAGCAACTGGTTCACTCGCTCAAAGTAACCAACCACTGAAAATC</u>
<u>GTTGTGCCTTTTCTGCAGGTGGTACAGCGGACGTATTACCACGTCTTGTCGCTGAAAAATCCGTGCCG</u>
<u>ATTATGCTGGTGGTGTTATCATCGAAAACAAACCAGGTGCAGGTGGTAATATTGGTGCAGATCTAGTTTT</u>
<u>CCGTGCTCCACCAGACGGTATGACGGTTTTAGCTTCACCACCTGGTCCTATCGCTATTAATCACAATCTT</u>
<u>TATCAAAAATTATCTTTCGATCCTACTCGTTGGGTACCAGTAACCATTCTGGCAACAGTTCCTAACGTAC</u>
<u>TTGTAATTAACCCAAAACTACCTGTTAAAAGCCTTGGCGAATTTATCGCATACGCAAAAGCAAATCCAAA</u>
<u>GAAAGTAACCGTAGCGACTCAAGGTGACGGTTCTACTTCACACCTTACAGCAGCAATGTTTATGCAATTA</u>
<u>ACTGGTACAGAACTAACTGTTATCCCATACAAAGGTACAGCACCAGCTTTAATCGATCTTATTGGTGGTA</u>
<u>ATGTAGACGTGTTTTTCGATAATATCAGCTCTTCTGCAACTTATCACCAAGCAGGAAAAGTTCGTATTCT</u>
<u>TGCAGTTGCTGATGAACAACGTTCACAAATTCTTCCACAAGTTCCAACGTTCGCAGAACAACAGTGGCCA</u>
<u>GCAATGCAAGCTGTGACATTTTTCTCAGTAGTGGCACCTCCTGGTACATCAGCAGAAATCGCACAAAAAC</u>

FIG. 20

TTCAAAAACAGATGGCTCTTGCCCTTTCTTCGAACGATATTCGTAAGCACTTCCAGGAACAAGGTGCTGT
GCCATGTGGTTGGGATCCAAGTAAAACTGCTCAATTTATTCGTCAGGAAACCGAAAAATGGAAGAAAGTA
CTCAAAGCAGCAAACGTAAAACTTTAAGAGAGGAAAGCAATGCAGGAAAGCATTATTCAATGGCATGGTG
CGACCAACACACGCGTTCCATTTGGTATCTATACAGATACCGCAAATGCTGACCAAGAACAACAGCGTAT
TTACCGTGGCGAAGTATGGAATTACCTTTGTTTGGAATCAGAAATCCCAGGAGCGGGTGATTTTCGTACC
ACATTTGCGGGTGAAACACCTATTGTCGTAGTTCGTGATGCTGATCAAGAAATTTATGCTTTCGAAAATC
GTTGTGCTCACCGTGGTGCTTTAATTGCATTAGAAAAGAGCGGTCGTACTGATTCTTTTCAATGTGTTTA
TCATGCATGGTCATATAACCGTCAGGGTGACCTTACGGGTGTGGCTTTCGAAAAAGGCGTAAAAGGTCAG
GGTGGTATGCCAGCTAGTTTCTGTAAAGAAGAACATGGTCCACGTAAACTTCGCGTAGCAGTTTTCTGCG
GCTTGGTTTTCGGTTCTTTTTCTGAAGACGTTCCAAGTATTGAAGATTATTTGGGTCCGGAAATTTGTGA
ACGTATCGAACGTGTTCTCCATAAGCCTGTAGAAGTTATCGGTCGTTTTACTCAGAAATTACCTAATAAC
TGGAAACTTTATTTTGAAAATGTAAAAGATAGCTACCATGCATCTCTTTTACACATGTTTTTCACAACTT
TCGAACTGAACCGTTTATCTCAGAAGGCGGTGTTATTGTGGATGAGTCTGGCGGCCATCATGTATCCTA
TAGTATGATTGATCGTGGGCCAAGGATGATTCATATAAAGATCAAGCTATTCGTTCTGACAATGAACGT
TATCGTTTGAAAGATCCTAGCTTACTAGAAGGTTTTGAAGAATTCGAAGATGGTGTAACGCTTCAAATTC
TTAGCGTATTCCCAGGGTTTGTTTTGCAACAAATCCAAAACAGTATTGCAGTGCGTCAGTTATTGCCAAA
AAGTATTTCTAGTTCTGAATTGAACTGGACTTATTTAGGTTATGCCGATGATAGCGCAGAACAACGTAAA
GTTCGTCTTAAACAAGCTAATCTGATTGGACCTGCTGGATTCATTTCAATGGAAGATGGTGCAGTCGGCG
GTTTCGTGCAGCGTGGTATTGCAGGCGCTGCTAACCTTGATGCAGTAATCGAAATGGGCGGTGATCATGA
AGGCAGCTCTGAAGGTCGCGCTACTGAAACTTCAGTACGTGGCTTTTGGAAAGCATATCGTAAACATATG
GGACAAGAAATGCAGGCATGAGGAGTCCCTAAACAATGATCAATGAAATACAGATCGGCAGCATTTAATGC
AGCATATGCAAAAACTATTGACTCTGATGCTATGGAACAATGGCCTACCTTTTTTACTAAAGATTGCCAT
TATTGTGTAACGAATGTAGATAATCATGATGAGGGTTTAGCTGCTGGTATAGTTTGGGCAGATTCACAGG
ACATGTTGACTGATCGTATCTCAGCTTTGCGTGAAGCGAACATTTACGAACGTCACCGCTATCGTCACAT
CTTAGGTCTGCCATCAATTCAATCAGGTGATGCAACGCAGGCATCAGCTAGCACACCTTTCATGGTTCTT
CGTATCATGCATACTGGCGAAACGGAGGTTTTCGCATCGGGTGAATATCTCGATAAATTCACTACTATTG
ATGGTAAATTGCGCCTTCAGGAACGTATTGCTGTTTGTGACTCTACAGTAACCGATACCTTAATGGCATT
GCCATTATGAAAGGAGGTAACAATGAACGCAATTGTTCACCGCCGTCTTGCACTTGCAATTGGTGATCCA
CATGGTATTGGTCCTGAAATCGCATTGAAAGCTCTTCAACAGCTTTCGGTAACTGAACGTAGCTTAATTA
AAGTATACGGTCCGTGGTCTGCACTTGAACAAGCAGCACGCGTTTGCGAAATGGAACCACTCTTACAAGA
TATCGTACACGAAGAAGCAGGTACCTTGACCCAACCAGTACAGTGGGGTGAAATTACACCACAAGCTGGT
CTTAGTACAGTACAATCAGCTACTGCTGCGATCCGTGCATGTGAAAATGGTGAGGTAGATGCAGTTATTG
CGTGTCCACACCATGAAACTGCAATCCACCGTGCTGGTATCGCCTTCTCTGGTTATCCAAGCCTTTTAGC
GAATGTGTTGGGTATGAACGAAGATCAAGTTTTTCTTATGTTGGTTGGTGCTGGTCTTCGTATCGTTCAT
GTGACTCTACACGAATCTGTACGTTCTGCACTTGAACGTCTTTCTCCACAACTTGTTGTAAATGCAGCAC
AAGCAGCAGTTCAAACCTGTACATTGCTTGGTGTTCCTAAACCGAAAGTGGCAGTGTTCGGCATTAACCC
ACATGCATCAGAAGGTCAACTTTTCGGCTTGGAAGATAGCCAAATTACCGTTCCAGCAGTTGAAACCCTT
CGTAAACGTGGTCTAGCTGTTGATGGTCCAATGGGTGCGGATATGGTACTGGCACAACGTAAACATGATT
TATATGTTGCGATGCTTCATGATCAGGGTCATATACCAATTAAACTTCTTGCACCAAATGGTGCGAGTGC
TCTCTCAATCGGTGGTCGTGTTGTATTGTCATCAGTTGGACACGGCAGCGCAATGGACATCGCTGGCCGT
GGCGTAGCTGATGCCACTGCTCTTTTACGTACCATTGCTCTTCTTGGCGCTCAGCCAGTTTGA**GGTCCCT
CCCAA**ATGAACCATCAAATCCACATCCATGACTCAGATATTGCATTTCCATGTGCACCTGGTCAATCAGT
TTTGGATGCGGCCTTACAAGCAGGTATCGAATTGCCTTATAGCTGCCGTAAAGGTTCATGTGGGAATTGT
GCAAGTACTCTTTTAGATGGTAATATTGCATCTTTCAACGGTATGGCTGTTCGTAATGAATTATGTGCGT
CTGAACAAGTGTTATTGTGTGGTTGCACGGCGGCATCTGATATACGTATTCATCCTTCTTCTTTCCGTCG

FIG. 20 (continued)

```
TCTTGACCCAGAAGCTCGTAAACGTTTCACTGCTAAGGTATATTCAAATACTCTTGCTGCTCCAGATGTA
TCTCTTCTCCGTCTCCGTTTACCTGTTGGTAAACGTGCTAAATTTGAAGCTGGTCAATATTTACTAATCC
ACTTAGATGACGGTGAGAGCCGTAGCTACAGCATGGCAAATCCACCACATGAATCTGATGGTATCACCTT
ACATGTTCGTCATGTTCCAGGTGGGCGTTTAGTACTATTGTACAACAATTGAAATCAGGAGATACTTTG
GACATTGAATTACCTTTTGGTTCTATTGCGCTTAAACCTGATGACGCTCGTCCTCTGATCTGTGTAGCTG
GTGGTACCGGCTTTGCTCCAATCAAATCCGTTTTAGACGATCTCGCGAAACGTAAAGTACAGCGCGATAT
CACACTTATCTGGGGCGCACGCAATCCATCTGGCTTATATCTTCCATCAGCTATCGATAAGTGGCGTAAG
GTATGGCCACAATTCCGTTACATCGCCGCTATCACTGATCTTGGGGATATGCCAGCTGATGCACACGCTG
GTCGTGTGGACGACGCATTACGTACTCATTTTGGTAATCTGCATGATCATGTTGTTCATTGTTGTGGTTC
GCCTGCTCTAGTTCAAAGTGTCCGTACAGCCGCCTCGGACATGGGTCTACTAGCGCAAGATTTCCATGCA
GATGTATTTGCAACTGGTCCTACAGGTCACCACTAGCGGAACGGCGATGTGAAAATTAAAAGTCAAAAG
ATTTTTTTTCTGGTTTGATGTTCCTTGCAGTTGGTTTAGCATTTGCAATTGGTGCTTCAAATTATACTAT
TGGTACTGGTGCTCGTATGGGTCCAGGTTATTTCCCTCTTATACTTGGTGTACTGATGGCGATTCTAGGT
GCAGCTATCTGTGTTGGTGGTCTTACTAAAGGTCCAGAGGGTGGTGATAAAATTGGTAAATGGGCATGGC
GTCAAGTTTTTTTTATCTTGGCAGCAAATTTTGCATTCGGCATTTTGTTAGTGGGTGTACCAGCAGTTGG
TATTCCACAATTTGGTCTTATTATCGCAATTTATGCGTTAGTCTTCATCGCGTCTTTGGGTGGCCACTCT
TTCAACTTCAAAGAAACCGCGATCCTTGCAACGGTGCTTGCAGTTGGTTCTTACTTCGCTTTTGTTTGGG
CATTAAACTTACAATTCCCAGTATGGCCATCATTTATCGCGGGTTAACCGGTAAGCGGCATGGATCTTAT
TCAAAACTTAAGTACCGGCTTCGGTGTGGCTTTCACTTTCCAAAATTTGATTTATTGTTTCGTTGGTTGT
CTTTTAGGTACTTTAATTGGCGTACTTCCAGGCATTGGTCCAGTTGCTACAATTGCAATGTTATTGCCTG
CAACCTATGCTTTACCACCAGTGGCTGCATTGATTATGTTGGCTGGTATCTACTATGGTGCGCAGTATGG
TGGTAGTACTACTGCTATTTTGGTAAATCTTCCGGGTGAATCTTCTTCTGTAGTCACCGTTATCGATGGT
TACCAAATGGCTCGTAAAGGTCGTGCAGGTCCAGCGCTTGCTGCTGCTGGTATTGGTTCTTTTTTCGCAG
GTTGTGTTGGTACAGTGATCTTAGCGGCTTTCGCTCCACCTCTCACGGAAGTTGCATTCAAGTTTGGACC
TGCAGAGTATTTTTCTTTAATGACATTGGGTCTAATTGGTGCAGTTGTCCTTGCTTCAGGCTCTTTGCTC
AAAGCAATTGCAATGATCGTACTCGGTCTTTTGCTTGGCATGGTTGGTACGGACGTAAATTCAGGTGTAG
CGCGTTACTCATTTGACATTCCAGAGCTAACAGATGGTATTGATTTGTTGTGATCGCAATGGGTGTTTT
TGGTTACGGTGAATTATTGCAAATCTTTCAAAGCCTGATGATGAACGTGAGGTTTTTGCAGCGAAAGTG
ACTGGTCTTCTTCCAACAAGTGAAGACTTCAAACGTATGTTGCCAGCAATGTTGCGTGGTACAGCATTAG
GTTCAGCTTTAGGAATTTTGCCAGGTGGTGGTGCTATGTTGAGTGCATTTGCAGCTTATACAATTGAAAA
AAAAACCAAATTAAAACCTGGTGAAGTACCATTTGGTCAGGGCAATATTCGTGGCGTTTGCGCTCCGGAA
TCAGCAAACAACGCTGGTAGTCAAACATCTTTCATTCCACTGTTAACATTGGGCATTCCTCCAAACGCCG
TAATGGCTCTCATGGTAGGCGCAATGACTATTCACAACATTCAACCAGGACCACAAGTGATGACATCTAA
CCCTGAACTATTTGGGGTCTTATTGCAAGCATGTGGATTGGTAATTTGATGTTAATTATTTTGAACCTA
CCACTTATCGGTGTGTGGATCAAGTTGCTTACAGTACCATATCGTTGGTTGTTTCCATCTATCGTATTAT
TTTGTGCAATTGGTGTGTATGGTACTAATAACAACGTTTGGGATGTTTGGATGGTAGGTATTTTTGGTTT
CATTGGTTATGTATTCCACAAGTTAGGGACTGAACCTGCTCCTTTGTTGTTGGGTTTCATTTTAGGTCCA
ATGATGGAAGAAAACCTTCGCCGTGCTCTATTGCTATCGCGTGGCGACTGGTCTGTATTTGTTACGCGTC
CAATTAGTGCATGCTTACTGGCAGCGGCTGTTGTGCTTCTTGTAATCGTTCTTATGCCTGCAGTTAAGAA
TAAACGTGAAGAGGCCTTTGTAGAAGATTGAACTAGTTCTAGAGCGGCCGCCACCGCGGTGGAGCTCGGT
ACGATCCGGTGATTGATTGAGCAAGCTTTATGCTTGTAAACCGTTTTGTGAAAAAATTTTTAAAATAAAA
AAGGGGACCTCTAGGGTCCCCAATTAATTAGTAATATAATCTATTAAAGGTCATTCAAAAGGTCATCCAC
CGGATCAATTCCCCTGCTCGCGCAGGCTGGGTGCCAAGCTCTCGGGTAACATCAAGGCCCGATCCTTGGA
GCCCTTGCCCTCCCGCACGATGATCGTGCCGTGATCGAAATCCAGATCCTTGACCCGCAGTTGCAAACCC
```

FIG. 20 (continued)

TCACTGATCCGTCGACCAAAGCGGCCATCGTGCCTCCCCACTCCTGCAGTTCGGGGGCATGGATGCGCGG
ATAGCCGCTGCTGGTTTCCTGGATGCCGACGGATTTGCACTGCCGGTAGAACTCCGCGAGGTCGTCCAGC
CTCAGGCAGCAGCTGAACCAACTCGCGAGGGGATCGAGCCCGGGGTGGGCGAAGAACTCCAGCATGAGAT
CCCCGCGCTGGAGGATCATCCAGCCGGCGTCCCGGAAAACGATTCCGAAGCCCAACCTTTCATAGAAGGC
GGCGGTGGAATCGAAATCTCGTGATGGCAGGTTGGGCGTCGCTTGGTCGGTCATTTCGAACCCCAGAGTC
CCGCTCAGAAGAACTCGTCAAGAAGGCGATAGAAGGCGATGCGCTGCGAATCGGGAGCGGCGATACCGTA
AAGCACGAGGAAGCGGTCAGCCCATTCGCCGCCAAGCTCTTCAGCAATATCACGGGTAGCCAACGCTATG
TCCTGATAGCGGTCCGCCACACCCAGCCGGCCACAGTCGATGAATCCAGAAAGCGGCCATTTTCCACCA
TGATATTCGGCAAGCAGGCATCGCCATGGGTCACGACGAGATCCTCGCCGTCGGGCATGCGCGCCTTGAG
CCTGGCGAACAGTTCGGCTGGCGCGAGCCCCTGATGCTCTTCGTCCAGATCATCCTGATCGACAAGACCG
GCTTCCATCCGAGTACGTGCTCGCTCGATGCGATGTTTCGCTTGGTGGTCGAATGGGCAGGTAGCCGGAT
CAAGCGTATGCAGCCGCCGCATTGCATCAGCCATGATGGATACTTTCTCGGCAGGAGCAAGGTGAGATGA
CAGGAGATCCTGCCCCGGCACTTCGCCCAATAGCAGCCAGTCCCTTCCCGCTTCAGTGACAACGTCGAGC
ACAGCTGCGCAAGGAACGCCCGTCGTGGCCAGCCACGATAGCCGCGCTGCCTCGTCCTGCAGTTCATTCA
GGGCACCGGACAGGTCGGTCTTGACAAAAAGAACCGGGCGCCCTGCGCTGACAGCCGGAACACGGCGGC
ATCAGAGCAGCCGATTGTCTGTTGTGCCCAGTCATAGCCGAATAGCCTCTCCACCCAAGCGGCCGGAGAA
CCTGCGTGCAATCCATCTTGTTCAATCATGCGAAACGATCCTCATCCTGTCTCTTGATCAGATCTTGATC
CCCTGCGCCATCAGATCCTTGGCGGCAAGAAAGCCATCCAGTTTACTTTGCAGGGCTTCCCAACCTTACC
AGAGGGCGCCCCAGCTGGCAATTCCGGTTCGCTTGCTGTCCATAAAACCGCCCAGTCTAGCTATCGCCAT
GTAAGCCCACTGCAAGCTACCTGCTTTCTCTTTGCGCTTGCGTTTTCCCTTGTCCAGATAGCCCAGTAGC
TGACATTCATCCGGGGTCAGCACCGTTTCTGCGGACTGGCTTTCTACGTGTTCCGCTTCCTTTAGCAGCC
CTTGCGCCCTGAGTGCTTGCGGCAGCGTGAAGCTCGCGCAGATCAGTTGGAAGAATTTGTCCACTACGTG
AAAGGCGAGATCACCAAGGTAGTCGGCAAATAATGTCTAACAATTCGTTCAAGCCGACGCCGCTTCGCGG
CGCGGCTTAACTCAAGCGTTAGATGCACTAAGCACATAATTGCTCACAGCCAAACTATCAGGTCAAGTCT
GCTTTTATTATTTTTAAGCGTGCATAATAAGCCCTACACAAATTGGGAGATATATCATGAAAGGCTGGCT
TTTTCTTGTTATCGCAATAGTTGGCGAAGTAATCGCAACATCCGCATTAAAATCTAGCGAGGGCTTTACT
AAGCTGATCCGGTGGATGACCTTTTGAATGACCTTTAATAGATTATATTACTAATTAATTGGGGACCCTA
GAGGTCCCCTTTTTTATTTTAAAAATTTTTTCACAAAACGGTTTACAAGCATAAAGCTTGCTCAATCAAT
CACCGGATCTACCGGGCCCCCCCTCGAGGTCGACGGTATCGATAAGCTTGATATCGAATTCCTGCAGCCC
GGGGGATCCACTAGT*TAAAACAAAAGAGAGCGATTAGTCGCTCTCTTTTTATCTCGGCTGTGTTTATT*
*TACAAGTGAAATTCTCGGCTTTTTCACTGTCACCTGTACCGTTATAACGTGCGATTTTTGGATATGGACA*
*TAGTGGTCGAGTTCGATTGGCCGACCAGCTCGATGGTAACTCGCTATTGATTTCGCCACTTGCATTACCG*
*ACACCGCGTGCAGAAGCGAGAATTTGATCTGGTGCTTGACCATATTCTACCCAGTTCACCAAAGCAGTAA*
*GTGCATCAAACTGGTCGGTCGCAAGCCCACCCCGCGAATGATTCATTCCCGGAACGCGATAAAAACGAGC*
*AAAACTTTGTGCGTCACCCAAACTGCTGCTCTTGTATTTTGCCATCAGTTTATCGTACCAGTTTTGTGTG*
*TCATCTACCGAAAATACGCCATCTGCTGTGCCTTGCACCACAATCATTTTACCGCCATGCAAGCGTAATT*
*TATCCAGATTGAGCTCATCTGGCGGATCATAAATGACATCGCGCTTTCTGAATAGGTCGAATTGGTTGC*
*AGAAAGTTTTGGGTAATCTGTATCAAAATTATAGTTAAAGGCAAATTTTCGTGAATTTTGCACAATTGTT*
*GGATCTGGTGGTACCTGAAATATAATGCCTACCGCTACCGGGTCGCGTGCCGTACCCACAGAAGAAACAA*
*ATTTCCAGCTTGCCCAATTGCTGCCAAGTAATCCCGGATCGTAAGGCTGGGTCGCATACAATGCTTCGCC*
*AGATGAATTGACAGGGCCGCGGTAAATATTAGCCACGACATCGATCTGGTCTTTACTCAAACAGCTTCCA*
*TCACGTGAACCCGAGCAGACAGGCACATCTTTATGAATATCAAAGGCGGTTCGACAGGCTTCAACGTCTT*
*GTACCATACCATCTGCTACACCATCGAGTGCATCACAGCGTGTTAAAATCGCATTGGCAAGTACGTTACG*
*TTCTGCATAGGTGAGTGCAGTGCTTAAATCATTTTCATCGGTGGCAACACGACGTAATTGCTGCGCCGTG*

FIG. 20 (continued)

```
TATAGCTGTGCCGCTGCTGCACGTGGTAGATGAAATCCGGGTGTGCTTGCCAAGATGCCATCGTACTGAT
CGCCTAGGCGTGTTGCAGCCATCATGGCATGTCGACCGCCGTTAGACGTACCTCCTGCATAAGATCGATC
TGGCAATTTACCGTAAGCTGTTTTAATCAGATCTTTGGCCATAGGCGTTAACTTTGTAATAGCACCATAA
CCATAGTTGATGCGAGCTTGCGGATCTAAACCAAAAGAGGATTTTGTGCAGATGAATGTCCGGCATCGG
ATGAAATTACCGCGAATCCGTCTTTTAAAGCATTGCTTAACATCCCGCCGCTGCCCACTTGTCCGGTCGC
TGTGGCGATGTTGCCGTCGGTACCGCCATTTCCTTGATATAGAAAACGTCCGTTCCAGCTCACCGGAAGT
CGCATTTCAAAGCCAATCTGATAGGTTTGACCATCGATTGGGCTAATACGTTGCTCCATATAACCTTTGA
CCAAACAATGCGCCGGAATATTTTTCCCCACGACGGTCAGAGCGCCTGCATTTTGTAAAGTTGCACTTTC
AACTACGGTGGTATCAAATTTGAAACCGCTTAAATCTGTACAACTGCCTTTGAGCTGAGCACCTACTGCT
GGGCTTAATTGTGGAATACTTTGGCTCGACTGTGCCGTATCATGATCGTTATTGTCATTACATGCAGCTA
CACTGATGCAGACGCCGAGCAATGCAGCATGTTTAAAAAAATGTTGAGGTTTTTTCATTGCAATATCCTT
ATGCCT
```

FIG. 20 (continued)

```
                    SEQUENCE LISTING

<160> NUMBER OF SEQ ID NOS: 66

<210> SEQ ID NO 1
<211> LENGTH: 904
<212> TYPE: DNA
<213> ORGANISM: Ideonella sakaiensis

<400> SEQUENCE: 1
tcatcaagtc aaaacactat ataggaacga aaccatgaac ttccctcgcg cgtcgcgcct    60
gatgcaggcg gcggtcctcg gtggtctgat ggcagtcagc gccgcggcca ccgctcagac   120
caacccatac gcccgcggcc caaaccctac cgcggccagc ctggaagcct ctgccggccc   180
attcaccgtg cgcagcttca ccgtcagtcg cccgtcgggc tatggtgccg gcaccgtcta   240
ctacccaacc aacgctggcg gcaccgtcgg cgccatcgca atcgtgccgg gctataccgc   300
ccgccagtcc tcgatcaagt ggtggggccc acgtctggcc tcccacggct tcgttgttat   360
caccatcgac accaactcga ccctggacca gccgtcctcc cgctcgagcc agcagatggc   420
```

```
tgctctgcgc caggtagctt cgctgaacgg caccagctct agcccaatct acggcaaagt    480
ggacaccgct cgcatgggcg tgatgggttg gtccatgggc ggtggtggtt ccctgatctc    540
cgctgctaat aatccttccc tgaaggccgc cgccccgcag gccccatggg actcctcgac    600
caacttctcg agcgtgaccg tgccgaccct gatcttcgct tgcgaaaacg acagcatcgc    660
tccggtgaac tcctccgcgc tgcctatcta cgactccatg agccgcaacg ccaagcaatt    720
cctggaaatc aacggcggtt cccactcctg cgctaactcg ggcaactcga accaagccct    780
gatcggcaag aagggcgtag catggatgaa gcgtttcatg gataacgaca cccgttactc    840
gaccttcgcc tgcgaaaacc cgaactctac tcgcgtcagc gacttccgca ctgcgaactg    900
cagc                                                                904

<210> SEQ ID NO 2
<211> LENGTH: 1839
<212> TYPE: DNA
<213> ORGANISM: Ideonella sakaiensis

<400> SEQUENCE: 2
taacaaggat tacatataag ggtatatcaa atgcagacca ccgtcaccac tatgctgctg     60
gcatcggtcg ccctggccgc ctgcgcaggc ggcggcagca ccccgctgcc gctgccgcag    120
caacagccgc cacagcagga gccgccgcct cctccagtcc cgctggcttc ccgtgctgcg    180
tgtgaggccc tgaaggacgg caacggggac atggtttggc cgaacgccgc caccgtagtt    240
gaagtggccg catggcgcga cgctgccccg gctaccgcgt ccgccgccgc tctgccggaa    300
cactgcgaag ttagcggcgc catcgccaag cgcactggta ttgacggtta ccgtacgaa    360 atcaagttcc gcctgcgcat gccggcggag tggaatggcc gtttcttcat ggagggtggt    420
tccggcacca acggctccct gagcgcggcc accggcagca tcgtggcgg ccagatcgcc    480 tcggccctgt cccgcaactt cgccaccatc gcgaccgacg gtggccacga caacgctgtc    540
aacgacaatc cagacgccct gggtacggta gcgttcggcc tggacccaca ggctcgcctg    600
gacatgggtt acaattcgta cgaccaggtg acccaagctg gcaaagccgc cgttgcccgt    660
ttctacggcc gtgccgccga caagtcgtac ttcatcggct gctcggaagg tggtcgggag    720
ggcatgatgc tcagccaacg cttcccatcc cactacgacg gtatcgtcgc cggtgcccct    780
ggctaccagc tgcctaaagc cggtatctcg ggcgcttgga ccactcagtc gctggccccg    840
gcggcggtgg gcctggacgc tcagggcgtc ccgctgatca caagagcttc tccgatgcc    900 gacctgcacc tgctgtcgca ggccatcctc ggtacttgcg atgcgctgga cggcctggct    960
gacggcatcg ttgacaacta ccgcgcgtgc caggccgctt cgacccggc taccgcggct   1020 aaccctgcca acggtcaagc tctgcaatgt gtgggtgcca aaaccgccga ttgcctgagc   1080
ccggtacagg ttaccgccat caaacgtgca atggccggcc cggtcaacag cgccggcacc   1140
ccgctgtaca accgttgggc ctgggacgct ggtatgagcg gcctgtccgg taccacctac   1200
aatcagggct ggcgttcctg gtggctgggt agcttcaact cctcggcgaa caacgcgcag   1260
cgtgtttcgg gtttctccgc ccgctcctgg ctggtcgact cgccaccccc accagagcct   1320
atgccgatga cccaggtggc tgcacgcatg atgaaattcg acttcgacat cgacccgctg   1380
aagatctggg ccaccagcgg ccagttcacc cagtcgagca tggactggca ggggccacc   1440 tccaccgacc tggccgcctt ccgcgatcgt ggcggcaaga tgatcctgta ccacggtatg   1500
agcgacgcag ccttctcggc cctggacacc gctgactact acgaacgcct gggcgccgct   1560
atgccgggcg ccgcgggctt cgctcgtctg ttcctcgtcc caggcatgaa ccactgttcg   1620
```

| | | |
|---|---|---|
| ggcggtccag gtaccgaccg tttcgacatg ctgacccctc tggtggcgtg ggttgagcgc | 1680 |
| ggcgaagccc cggaccagat ctcggcgtgg agcggcaccc caggctactt cggcgtcgct | 1740 |
| gcccgtaccc gcccgctgtg cccgtacccg caaatcgcac gctacaaggg ttccggcgat | 1800 |
| atcaacaccg aagcaaactt cgcctgcgcc gcgcctccg | 1839 |

```
<210> SEQ ID NO 3
<211> LENGTH: 10955
<212> TYPE: DNA
<213> ORGANISM: Artificial Sequence
<220> FEATURE:
<223> OTHER INFORMATION: plasmid pLJ080

<400> SEQUENCE: 3
```

| | | |
|---|---|---|
| ttgagatcct ttttttctgc gcgtaatctg ctgcttgcaa acaaaaaaac caccgctacc | 60 |
| agcggtggtt tgtttgccgg atcaagagct accaactctt tttccgaagg taactggctt | 120 |
| cagcagagcg cagataccaa atactgttct tctagtgtag ccgtagttag gccaccactt | 180 |
| caagaactct gtagcaccgc ctacatacct cgctctgcta atcctgttac cagtggctgc | 240 |
| tgccagtggc gataagtcgt gtcttaccgg gttggactca agacgatagt taccggataa | 300 |
| ggcgcagcgg tcgggctgaa cggggggttc gtgcacacag cccagcttgg agcgaacgac | 360 |
| ctacaccgaa ctgagatacc tacagcgtga gctatgagaa agcgccacgc ttcccgaagg | 420 |
| gagaaaggcg gacaggtatc cggtaagcgg cagggtcgga acaggagagc gcacgaggga | 480 |
| gcttccaggg ggaaacgcct ggtatcttta tagtcctgtc gggtttcgcc acctctgact | 540 |
| tgagcgtcga ttttttgtgat gctcgtcagg ggggcggagc ctatggaaaa acgcctcaca | 600 |
| caggaaacag ctatgacatg attacgaatt cgagctcggt acccgtgcga ttactgtggg | 660 |
| agcgggcatg cccgcgaatg ggagcaacac aaggctcaat ggttgacggt gtgcgccagc | 720 |
| atcaccgaca actggcacag cggccgcccg ctctctgcat gccactggtt gaacgcctgc | 780 |
| tgcaccagag ccaggtcgcg ctggctggtt ggctgcttgt cgatcacctt ctgcgcaatc | 840 |
| aacgccgctg ccatgtcatc ggtcgggatg aacgtgtcct tgccgaccat gcgcaagaac | 900 |
| cgtggcgccg acaacccgcc caactggttg ccgtgcttgg ccaggtactt ccacaagccg | 960 |
| acaatgtcgg tcactggcca atcggcgatg aatgcaccaa aactgccatg cgccttggcg | 1020 |
| atatccagca ccatttgcgc attgcgtggc acgctcttga gcttgcccag gtggcggata | 1080 |
| atgcgctcat cctgcatcaa ccgctccaga tgctcggcgc ccatcagcac cactttctcc | 1140 |
| gggtcgaagc caaagaacac ctgctcgaac gccggccact ggcatccac caggctgtgc | 1200 |
| ttgagccccg cgcggaacac gcgcagggcc aatgtcgaca ggtagcggtc gtcactgatg | 1260 |
| tcgcgcagtt gcgccggcgt gcgcggctgc ggcaggaaag cctccagcgc ctgggccgaa | 1320 |
| ccaaagcggt tcaggcaata ctcagtgtga aattgttatc cgctcacaat tccacacatt | 1380 |
| atacgagccg atgattaatt gtcaacagct cttcatcaag tcaaaacact atataggaac | 1440 |
| gaaaccatga acttccctcg cgcgtcgcgc ctgatgcagg cggcggtcct cggtggtctg | 1500 |
| atggcagtca gcgccgcggc caccgctcag accaacccat acgcccgcgg cccaaaccct | 1560 |
| accgcggcca gcctggaagc ctctgccggc ccattcaccg tgcgcagctt caccgtcagt | 1620 |
| cgcccgtcgg gctatggtgc cggcaccgtc tactacccaa ccaacgctgg cggcaccgtc | 1680 |
| ggcgccatcg caatcgtgcc gggctatacc gcccgccagt cctcgatcaa gtggtgggc | 1740 |
| ccacgtctgg cctcccacgg cttcgttgtt atcaccatcg acaccaactc gaccctggac | 1800 |

```
cagccgtcct cccgctcgag ccagcagatg gctgctctgc gccaggtagc ttcgctgaac    1860
ggcaccagct ctagcccaat ctacggcaaa gtggacaccg ctcgcatggg cgtgatgggt    1920
tggtccatgg gcggtggtgg ttccctgatc tccgctgcta ataatccttc cctgaaggcc    1980
gccgccccgc aggcccccatg ggactcctcg accaacttct cgagcgtgac cgtgccgacc    2040
ctgatcttcg cttgcgaaaa cgacagcatc gctccggtga actcctccgc gctgcctatc    2100
tacgactcca tgagccgcaa cgccaagcaa ttcctggaaa tcaacggcgg ttcccactcc    2160
tgcgctaact cgggcaactc gaaccaagcc ctgatcggca agaagggcgt agcatggatg    2220
aagcgtttca tggataacga cacccgttac tcgaccttcg cctgcgaaaa cccgaactct    2280
actcgcgtca gcgacttccg cactgcgaac tgcagcctat aacaaggatt acatataagg    2340
gtatatcaaa tgcagaccac cgtcaccact atgctgctgg catcggtcgc cctggccgcc    2400
tgcgcaggcg gcggcagcac cccgctgccg ctgccgcagc aacagccgcc acagcaggag    2460
ccgccgcctc ctccagtccc gctggcttcc cgtgctgcgt gtgaggccct gaaggacggc    2520 aacgggggaca tggtttggcc gaacgccgcc accgtagttg aagtggccgc atggcgcgac    2580
gctgccccgg ctaccgcgtc cgccgccgct ctgccggaac actgcgaagt tagcggcgcc    2640
atcgccaagc gcactggtat tgacggttat ccgtacgaaa tcaagttccg cctgcgcatg    2700
ccggcggagt ggaatggccg tttcttcatg gagggtggtt ccggcaccaa cggctccctg    2760
agcgcggcca ccggcagcat cggtggcggc cagatcgcct cggccctgtc ccgcaacttc    2820
gccaccatcg cgaccgacgg tggccacgac aacgctgtca cgacaatccc agacgccctg    2880
ggtacggtag cgttcggcct ggaccccacag gctcgcctgg acatgggtta caattcgtac    2940
gaccaggtga cccaagctgg caaagccgcc gttgcccgtt tctacggccg tgccgccgac    3000
aagtcgtact tcatcggctg ctcggaaggt ggtcgggagg gcatgatgct cagccaacgc    3060
ttcccatccc actacgacgg tatcgtcgcc ggtgcccctg gctaccagct gcctaaagcc    3120
ggtatctcgg gcgcttggac cactcagtcg ctggcccccgg cggcgtggg cctgacgct    3180 cagggcgtcc cgctgatcaa caagagcttc tccgatgccg acctgcacct gctgtcgcag    3240
gccatcctcg gtacttgcga tgcgctggac ggcctggctg acggcatcgt tgacaactac    3300
cgcgcgtgcc aggccgcttt cgacccggct accgcggcta accctgccaa cggtcaagct    3360
ctgcaatgtg tgggtgccaa aaccgccgat tgcctgagcc cggtacaggt taccgccatc    3420
aaacgtgcaa tggccggccc ggtcaacagc gccggcaccc cgctgtacaa ccgttgggcc    3480
tgggacgctg gtatgagcgg cctgtccggt accacctaca atcagggctg gcgttcctgg    3540
tggctgggta gcttcaactc ctcggcgaac aacgcgcagc gtgtttcggg tttctccgcc    3600
cgctcctggc tggtcgactt cgccacccca ccagagccta tgccgatgac ccaggtggct    3660
gcacgcatga tgaaattcga cttcgacatc gacccgctga gatctgggc caccagcggc    3720 cagttcaccc agtcgagctt gagatccttt ttttctgcgc gtaatctgct gcttgcaaac    3780
aaaaaaacca ccgctaccag cggtggtttg tttgccggat caagagctac caactctttt    3840
tccgaaggta actggcttca gcagagcgca gataccaaat actgttcttc tagtgtagcc    3900
gtagttaggc caccacttca agaactctgt agcaccgcct acatacctcg ctctgctaat    3960
cctgttacca gtggctgctg ccagtggcga taagtcgtgt cttaccgggt tggactcaag    4020
acgatagtta ccggataagg cgcagcggtc gggctgaacg ggggggttcgt gcacacagcc    4080 cagcttggag cgaacgacct acaccgaact gagataccta cagcgtgagc tatgagaaag    4140
cgccacgctt cccgaaggga gaaaggcgga caggtatccg gtaagcggca gggtcggaac    4200
```

```
aggagagcgc acgagggagc ttccagggg aaacgcctgg tatctttata gtcctgtcgg    4260
gtttcgccac ctctgacttg agcgtcgatt tttgtgatgc tcgtcagggg ggcggagcct    4320
atggaaaaac gcctcacaca ggaaacagct atgacatgat tacgaattcg agctcggtac    4380
ccgtgcgatt actgtgggag cgggcatgcc cgcgaatgag agcaacacaa ggctcaatgg    4440
ttgacggtgt gcgccagcat caccgacaac tggcacagcg gccgcccgct ctctgcatgc    4500
cactggttga acgcctgctg caccagagcc aggtcgcgct ggctggttgg ctgcttgtcg    4560
atcaccttct gcgcaatcaa cgccgctgcc atgtcatcgg tcgggatgaa cgtgtccttg    4620
ccgaccatgc gcaagaaccg tggcgccgac aacccgccca actggttgcc gtgcttggcc    4680
aggtacttcc acaagccgac aatgtcggtc actggccaat cggcgatgaa tgcaccaaaa    4740
ctgccatgcg ccttggcgat atccagcacc atttgcgcat tgcgtggcac gctcttgagc    4800
ttgcccaggt ggcggataat gcgctcatcc tgcatcaacc gctccagatg ctcggcgccc    4860
atcagcacca ctttctccgg gtcgaagcca agaacacct gctcgaacgc cggccacttg    4920
gcatccacca ggctgtgctt gagccccgcg cggaacacgc gcagggccaa tgtcgacagg    4980
tagcggtcgt cactgatgtc gcgcagttgc gccggcgtgc gcggctgcgg caggaaagcc    5040
tccagcgcct gggccgaacc aaagcggttc aggcaatact cagtgtgaaa ttgttatccg    5100
ctcacaattc cacacattat acgagccgat gattaattgt caacagctct tcatcaagtc    5160
aaaacactat ataggaacga aaccatgaac ttccctcgcg cgtcgcgcct gatgcaggcg    5220
gcggtcctcg gtggtctgat ggcagtcagc gccgcggcca ccgctcagac caacccatac    5280
gcccgcggcc caaaccctac cgcggccagc ctggaagcct ctgccggccc attcaccgtg    5340
cgcagcttca ccgtcagtcg cccgtcgggc tatggtgccg gcaccgtcta ctacccaacc    5400
aacgctggcg gcaccgtcgg cgccatcgca atcgtgccgg gctataccgc ccgccagtcc    5460
tcgatcaagt ggtggggccc acgtctggcc tcccacggct tcgttgttat caccatcgac    5520
accaactcga ccctggacca gccgtcctcc cgctcgagcc agcagatggc tgctctgcgc    5580
caggtagctt cgctgaacgg caccagctct agcccaatct acggcaaagt ggacaccgct    5640
cgcatgggcg tgatgggttg gtccatgggc ggtggtggtt ccctgatctc cgctgctaat    5700
aatccttccc tgaaggccgc cgccccgcag gccccatggg actcctcgac caacttctcg    5760
agcgtgaccg tgccgaccct gatcttcgct tgcgaaaacg acagcatcgc tccggtgaac    5820
tcctccgcgc tgcctatcta cgactccatg agccgcaacg ccaagcaatt cctggaaatc    5880
aacggcggtt cccactcctg cgctaactcg ggcaactcga accaagccct gatcggcaag    5940
aagggcgtag catggatgaa gcgtttcatg gataacgaca cccgttactc gaccttcgcc    6000
tgcgaaaacc cgaactctac tcgcgtcagc gacttccgca ctgcgaactg cagcctataa    6060
caaggattac atataagggt atatcaaatg cagaccaccg tcaccactat gctgctggca    6120
tcggtcgccc tggccgcctg cgcaggcggc ggcagcaccc cgctgccgct gccgcagcaa    6180
cagccgccac agcaggagcc gccgcctcct ccagtcccgc tggcttcccg tgctgcgtgt    6240
gaggccctga aggacggcaa cggggacatg gtttggccga acgccgccac cgtagttgaa    6300
gtggccgcat ggcgcgacgc tgccccgct accgcgtccg ccgccgctct gccggaacac    6360
tgcgaagtta gcggcgccat cgccaagcgc actggtattg acggttatcc gtacgaaatc    6420
aagttccgcc tgcgcatgcc ggcggagtgg aatggccgtt tcttcatgga gggtggttcc    6480
ggcaccaacg gctccctgag cgcggccacc ggcagcatcg gtgcggcca gatcgcctcg    6540
```

```
gccctgtccc gcaacttcgc caccatcgcg accgacggtg gccacgacaa cgctgtcaac    6600
gacaatccag acgccctggg tacggtagcg ttcggcctgg acccacaggc tcgcctggac    6660
atgggttaca attcgtacga ccaggtgacc caagctggca agccgccgt tgcccgtttc     6720
tacgccgtg ccgccgacaa gtcgtacttc atcggctgct cggaaggtgg tcggagggc      6780
atgatgctca gccaacgctt cccatcccac tacgacggta tcgtcgccgg tgcccctggc    6840
taccagctgc ctaaagccgg tatctcgggc gcttggacca ctcagtcgct ggccccggcg    6900
gcggtgggcc tggacgctca gggcgtcccg ctgatcaaca agagcttctc cgatgccgac    6960
ctgcacctgc tgtcgcaggc catcctcggt acttgcgatg cgctggacgg cctggctgac    7020
ggcatcgttg acaactaccg cgcgtgccag gccgcttcg acccggctac cgcggctaac     7080
cctgccaacg gtcaagctct gcaatgtgtg ggtgccaaaa ccgccgattg cctgagcccg    7140
gtacaggtta ccgccatcaa acgtgcaatg gccggcccgg tcaacagcgc cggcaccccg    7200
ctgtacaacc gttgggcctg ggacgctggt atgagcggcc tgtccggtac cacctacaat    7260
cagggctggc gttcctggtg gctgggtagc ttcaactcct cggcgaacaa cgcgcagcgt    7320
gtttcggggtt tctccgcccg ctcctggctg gtcgacttcg ccaccccacc agagcctatg   7380
ccgatgaccc aggtggctgc acgcatgatg aaattcgact tcgacatcga cccgctgaag    7440
atctgggcca ccagcggcca gttcacccag tcgagcatgg actggcacgg ggccacctcc    7500
accgacctgg ccgccttccg cgatcgtggc ggcaagatga tcctgtacca cggtatgagc    7560
gacgcagcct tctcggccct ggacaccgct gactactacg aacgcctggg cgccgctatg    7620
ccgggcgccg cgggcttcgc tcgtctgttc ctcgtcccag gcatgaacca ctgttcgggc    7680
ggtccaggta ccgaccgttt cgacatgctg accctctgg tggcgtgggt tgagcgcggc     7740
gaagcccgg accagatctc ggcgtggagc ggcaccccag gctacttcgg cgtcgctgcc    7800
cgtacccgcc cgctgtgccc gtacccgcaa atcgcacgct acaagggttc cggcgatatc    7860
aacaccgaag caaacttcgc ctgcgccgcg cctccgagtc aaaagcctcc ggtcggaggc    7920
ttttgacttc aaaaccaccc tgctgtcgat gatgctgccg ctgatgcacc acggcatgct    7980
ggtgatgggc ctgccctaca gcgagtcggc actgctcgag acccgtggtg gcggcacgcc    8040
ttatggcgcc agccaccacg caggcgccga tggcaagcgc gaactcgacc cacacgaaat    8100
cgccctgtgc cgcgccctgg gccaacgcct ggcgaccacg gccaaggccc tggaggcggc   8160
gcgtggctag aaagcccaag gcattgccgc cggtccaatg gctggtacca cgcctgcgcc    8220
tgacgcgggc attgagcctg gcatgcttct tcggcctgat cgccctgctg gtggtgaaca    8280
acctgtggtt cgccaacctg catggggcca gggtcgaggt gatcctggcg atcgagctgg    8340
tgccgttgct gttgctgttg ccaggcatgc tgaaaggcag cgcccgggcg catgcctgga    8400
cctgcttcgt ggtgaatatc tatttcatca agggcgtgct ggcggcgttc gacccggcgc    8460
gggcggtatt cggctggctt gaagtgctgg tgagcctggg gctgttcatt gccgggctac    8520
tgtacgtgcg ctgaagttc cagcatgagc ggcgcatggc gggcgaaggc agttagattt     8580
cctgcaggca tgcaagcttg gcactggccg tcgttttaca acgtcgtgac cggaattgcc    8640
agctggggcg ccctctggta aggttgggaa gccctgcaaa caggatgagg atcgtttcgc    8700
atgattgaac aagatggatt gcacgcaggt tctccggccg cttgggtgga gaggctattc    8760
ggctatgact gggcacaaca gacaatcggc tgctctgatg ccgccgtgtt ccggctgtca    8820
gcgcaggggc gcccggttct ttttgtcaag accgacctgt ccggtgccct gaatgaactc    8880
caagacgagg cagcgcggct atcgtggctg gccacgacgg gcgttccttg cgcagctgtg    8940
```

```
ctcgacgttg tcactgaagc gggaagggac tggctgctat tgggcgaagt gccggggcag    9000
gatctcctgt catctcacct tgctcctgcc gagaaagtat ccatcatggc tgatgcaatg    9060
cggcggctgc atacgcttga tccggctacc tgcccattcg accaccaagc gaaacatcgc    9120
atcgagcgag cacgtactcg gatggaagcc ggtcttgtcg atcaggatga tctggacgaa    9180
gagcatcagg ggctcgcgcc agccgaactg ttcgccaggc tcaaggcgcg gatgcccgac    9240
ggcgaggatc tcgtcgtgac ccatggcgat gcctgcttgc cgaatatcat ggtggaaaat    9300
ggccgctttt ctggattcat cgactgtggc cggctgggtg tggcggaccg ctatcaggac    9360
atagcgttgg ctacccgtga tattgctgaa gagcttggcg cgaatgggc tgaccgcttc     9420
ctcgtgcttt acggtatcgc cgctcccgat cgcagcgca tcgccttcta tcgccttctt     9480
gacgagttct tctgagcgac gatgaacatc aaaaagtttg caaacaagc aacagtatta     9540
acctttacta ccgcactgct ggcaggaggc gcaactcaag cgtttgcgaa agaaacgaac    9600
caaaagccat ataaggaaac atacggcatt tcccatatta cacgccatga tatgctgcaa   9660
atccctgaac agcaaaaaaa tgaaaaatat caagtttctg aatttgattc gtccacaatt   9720
aaaaatatct cttctgcaaa aggcctggac gtttgggaca gctggccatt acaaaacgct   9780
gacggcactg tcgcaaacta tcacggctac cacatcgtct ttgcattagc cggagatcct   9840
aaaaatgcgg atgacacatc gatttacatg ttctatcaaa aagtcggcga aacttctatt   9900
gacagctgga aaaacgctgg ccgcgtcttt aaagacagcg acaaattcga tgcaaatgat   9960
tctatcctaa aagaccaaac acaagaatgg tcaggttcag ccacatttac atctgacgga  10020
aaaatccgtt tattctacac tgatttctcc ggtaaacatt acggcaaaca aacactgaca  10080
actgcacaag ttaacgtatc agcatcgac agctctttga acatcaacgg tgtagaggat   10140
tataaatcaa tctttgacgg tgacggaaaa acgtatcaaa atgtacagca gttcatcgat  10200
gaaggcaact acagctcagg cgacaaccat acgctgagag atcctcacta cgtagaagat  10260
aaaggccaca atacttagt atttgaagca aacactggaa ctgaagatgg ctaccaaggc   10320
gaagaatctt tatttaacaa agcatactat ggcaaaagca catcattctt ccgtcaagaa  10380
agtcaaaaac ttctgcaaag cgataaaaaa cgcacggctg agttagcaaa cggcgctctc  10440
ggtatgattg agctaaacga tgattacaca ctgaaaaaag tgatgaaacc gctgattgca  10500
tctaacacag taacgatga aattgaacgc gcgaacgtct ttaaaatgaa cggcaaatgg    10560
tacctgttca ctgactcccg cggatcaaaa atgacgattg acggcattac gtctaacgat  10620
atttacatgc ttggttatgt ttctaattct ttaactggcc catacaagcc gctgaacaaa  10680
actggccttg tgttaaaaat ggatcttgat cctaacgatg taacctttac ttactcacac  10740
ttcgctgtac ctcaagcgaa aggaaacaat gtcgtgatta caagctatat gacaaacaga  10800
ggattctacg cagacaaaca atcaacgttt gcgccgagct tcctgctgaa catcaaggc   10860
aagaaaacat ctgttgtcaa agacagcatc cttgaacaag acaattaac agttaacaaa   10920
taatcagacc ccgtagaaaa gatcaaagga tcttc                              10955
```

<210> SEQ ID NO 4
<211> LENGTH: 290
<212> TYPE: PRT
<213> ORGANISM: Ideonella sakaiensis

<400> SEQUENCE: 4

Met Asn Phe Pro Arg Ala Ser Arg Leu Met Gln Ala Ala Val Leu Gly
1               5                   10                  15

Gly Leu Met Ala Val Ser Ala Ala Thr Ala Gln Thr Asn Pro Tyr
                20                  25                  30

Ala Arg Gly Pro Asn Pro Thr Ala Ser Leu Glu Ala Ser Ala Gly
            35                  40                  45

Pro Phe Thr Val Arg Ser Phe Thr Val Ser Arg Pro Ser Gly Tyr Gly
    50                  55                  60

Ala Gly Thr Val Tyr Tyr Pro Thr Asn Ala Gly Gly Thr Val Gly Ala
65                  70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Ser Ser Arg Ser Ser Gln Gln Met
        115                 120                 125

Ala Ala Leu Arg Gln Val Ala Ser Leu Asn Gly Thr Ser Ser Ser Pro
130                 135                 140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp Asp Ser Ser Thr Asn Phe Ser
            180                 185                 190

Ser Val Thr Val Pro Thr Leu Ile Phe Ala Cys Glu Asn Asp Ser Ile
        195                 200                 205

Ala Pro Val Asn Ser Ser Ala Leu Pro Ile Tyr Asp Ser Met Ser Arg
210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
            260                 265                 270

Cys Glu Asn Pro Asn Ser Thr Arg Val Ser Asp Phe Arg Thr Ala Asn
        275                 280                 285

Cys Ser
    290

<210> SEQ ID NO 5
<211> LENGTH: 603
<212> TYPE: PRT
<213> ORGANISM: Ideonella sakaiensis

<400> SEQUENCE: 5

Met Gln Thr Thr Val Thr Thr Met Leu Leu Ala Ser Val Ala Leu Ala
1               5                   10                  15

Ala Cys Ala Gly Gly Gly Ser Thr Pro Leu Pro Leu Pro Gln Gln Gln
                20                  25                  30

Pro Pro Gln Gln Glu Pro Pro Pro Val Pro Leu Ala Ser Arg
            35                  40                  45

Ala Ala Cys Glu Ala Leu Lys Asp Gly Asn Gly Asp Met Val Trp Pro
50                  55                  60

Asn Ala Ala Thr Val Val Glu Val Ala Ala Trp Arg Asp Ala Ala Pro
65                  70                  75                  80

```
Ala Thr Ala Ser Ala Ala Leu Pro Glu His Cys Glu Val Ser Gly
            85                  90                  95

Ala Ile Ala Lys Arg Thr Gly Ile Asp Gly Tyr Pro Tyr Glu Ile Lys
            100                 105                 110

Phe Arg Leu Arg Met Pro Ala Glu Trp Asn Gly Arg Phe Phe Met Glu
            115                 120                 125

Gly Gly Ser Gly Thr Asn Gly Ser Leu Ser Ala Ala Thr Gly Ser Ile
            130                 135                 140

Gly Gly Gly Gln Ile Ala Ser Ala Leu Ser Arg Asn Phe Ala Thr Ile
145                 150                 155                 160

Ala Thr Asp Gly Gly His Asp Asn Ala Val Asn Asp Asn Pro Asp Ala
            165                 170                 175

Leu Gly Thr Val Ala Phe Gly Leu Asp Pro Gln Ala Arg Leu Asp Met
            180                 185                 190

Gly Tyr Asn Ser Tyr Asp Gln Val Thr Gln Ala Gly Lys Ala Ala Val
            195                 200                 205

Ala Arg Phe Tyr Gly Arg Ala Ala Asp Lys Ser Tyr Phe Ile Gly Cys
            210                 215                 220

Ser Glu Gly Gly Arg Glu Gly Met Met Leu Ser Gln Arg Phe Pro Ser
225                 230                 235                 240

His Tyr Asp Gly Ile Val Ala Gly Ala Pro Gly Tyr Gln Leu Pro Lys
            245                 250                 255

Ala Gly Ile Ser Gly Ala Trp Thr Thr Gln Ser Leu Ala Pro Ala Ala
            260                 265                 270

Val Gly Leu Asp Ala Gln Gly Val Pro Leu Ile Asn Lys Ser Phe Ser
            275                 280                 285

Asp Ala Asp Leu His Leu Leu Ser Gln Ala Ile Leu Gly Thr Cys Asp
            290                 295                 300

Ala Leu Asp Gly Leu Ala Asp Gly Ile Val Asp Asn Tyr Arg Ala Cys
305                 310                 315                 320

Gln Ala Ala Phe Asp Pro Ala Thr Ala Ala Asn Pro Ala Asn Gly Gln
            325                 330                 335

Ala Leu Gln Cys Val Gly Ala Lys Thr Ala Asp Cys Leu Ser Pro Val
            340                 345                 350

Gln Val Thr Ala Ile Lys Arg Ala Met Ala Gly Pro Val Asn Ser Ala
            355                 360                 365

Gly Thr Pro Leu Tyr Asn Arg Trp Ala Trp Asp Ala Gly Met Ser Gly
            370                 375                 380

Leu Ser Gly Thr Thr Tyr Asn Gln Gly Trp Arg Ser Trp Trp Leu Gly
385                 390                 395                 400

Ser Phe Asn Ser Ser Ala Asn Asn Ala Gln Arg Val Ser Gly Phe Ser
            405                 410                 415

Ala Arg Ser Trp Leu Val Asp Phe Ala Thr Pro Pro Glu Pro Met Pro
            420                 425                 430

Met Thr Gln Val Ala Ala Arg Met Met Lys Phe Asp Phe Asp Ile Asp
            435                 440                 445

Pro Leu Lys Ile Trp Ala Thr Ser Gly Gln Phe Thr Gln Ser Ser Met
            450                 455                 460

Asp Trp His Gly Ala Thr Ser Thr Asp Leu Ala Ala Phe Arg Asp Arg
465                 470                 475                 480

Gly Gly Lys Met Ile Leu Tyr His Gly Met Ser Asp Ala Ala Phe Ser
            485                 490                 495
```

```
Ala Leu Asp Thr Ala Asp Tyr Tyr Glu Arg Leu Gly Ala Ala Met Pro
            500                 505                 510

Gly Ala Ala Gly Phe Ala Arg Leu Phe Leu Val Pro Gly Met Asn His
        515                 520                 525

Cys Ser Gly Gly Pro Gly Thr Asp Arg Phe Asp Met Leu Thr Pro Leu
    530                 535                 540

Val Ala Trp Val Glu Arg Gly Glu Ala Pro Asp Gln Ile Ser Ala Trp
545                 550                 555                 560

Ser Gly Thr Pro Gly Tyr Phe Gly Val Ala Ala Arg Thr Arg Pro Leu
                565                 570                 575

Cys Pro Tyr Pro Gln Ile Ala Arg Tyr Lys Gly Ser Gly Asp Ile Asn
            580                 585                 590

Thr Glu Ala Asn Phe Ala Cys Ala Ala Pro Pro
            595                 600

<210> SEQ ID NO 6
<211> LENGTH: 4229
<212> TYPE: DNA
<213> ORGANISM: Artificial Sequence
<220> FEATURE:
<223> OTHER INFORMATION: plasmid pLJ081

<400> SEQUENCE: 6
atcattcagg acgagcctca gactccagcg taactggact gaaaacaaac taaagcgccc      60
ttgtggcgct ttagttttgt tccgcggcca ccggctggct cgcttcgctc ggcccgtgga     120
caaccctgct ggacaagctg atggacaggc tgcgcctgcc cacgagcttg accacaggga     180
ttgcccaccg gctacccagc cttcgaccac atacccaccg gctccaactg cgcggcctgc     240
ggccttgccc catcaatttt tttaattttc tctggggaaa agcctccggc ctgcggcctg     300
cgcgcttcgc ttgccggttg acaccaagt ggaaggcggg tcaaggctcg cgcagcgacc     360
gcgcagcggc ttggccttga cgcgcctgga acgacccaag cctatgcgag tgggggcagt     420
cgaaggcgaa gcccgcccgc ctgcccccg agcctcacgg cggcgagtgc gggggttcca     480
agggggcagc gccaccttgg gcaaggccga aggccgcgca gtcgatcaac aagccccgga     540
ggggccactt tttgccggag ggggagccgc gccgaaggcg tggggaacc ccgcagggt     600 gcccttcttt gggcaccaaa gaactagata tagggcgaaa tgcgaaagac ttaaaaatca     660
acaacttaaa aaaggggggt acgcaacagc tcattgcggc accccccgca atagctcatt     720
gcgtaggtta agaaaatct gtaattgact gccacttttta cgcaacgcat aattgttgtc     780
gcgctgccga aaagttgcag ctgattgcgc atggtgccgc aaccgtgcgg caccctaccg     840
catggagata agcatggcca cgcagtccag agaaatcggc attcaagcca agaacaagcc     900
cggtcactgg gtgcaaacgg aacgcaaagc gcatgaggcg tgggccgggc ttattgcgag     960
gaaacccacg gcggcaatgc tgctgcatca cctcgtggcg cagatgggcc accagaacgc    1020
cgtggtggtc agccagaaga cactttccaa gctcatcgga cgttctttgc ggacggtcca    1080
atacgcagtc aaggacttgg tggccgagcg ctggatctcc gtcgtgaagc tcaacggccc    1140
cggcaccgtg tcggcctacg tggtcaatga ccgcgtggcg tggggccagc ccgcgacca    1200 gttgcgcctg tcggtgttca gtgccgccgt ggtggttgat cacgcgacc aggacgaatc    1260 gctgttgggg catggcgacc tgcgccgcat cccgaccctg tatccgggcg agcagcaact    1320
accgaccggc cccggcgagg agccgcccag ccagcccggc attccgggca tggaaccaga    1380
cctgccagcc ttgaccgaaa cggaggaatg ggaacggcgc gggcagcagc gcctgccgat    1440
```

| | |
|---|---|
| gcccgatgag ccgtgttttc tggacgatgg cgagccgttg gagccgccga cacgggtcac | 1500 |
| gctgccgcgc cggtagtacg taagaggttc aactttcac cataatgaaa taagatcact | 1560 |
| accgggcgta ttttttgagt tatcgagatt ttcaggagct aaggaagcta aaatgagcca | 1620 |
| tattcaacgg gaaacgtctt gctcgaggcc gcgattaaat tccaacatgg atgctgattt | 1680 |
| atatgggtat aaatgggctc gcgataatgt cgggcaatca ggtgcgacaa tctatcgatt | 1740 |
| gtatgggaag cccgatgcgc cagagttgtt tctgaaacat ggcaaaggta gcgttgccaa | 1800 |
| tgatgttaca gatgagatgg tcaggctaaa ctggctgacg gaatttatgc ctcttccgac | 1860 |
| catcaagcat tttatccgta ctcctgatga tgcatggtta ctcaccactg cgatcccagg | 1920 |
| gaaaacagca ttccaggtat tagaagaata tcctgattca ggtgaaaata ttgttgatgc | 1980 |
| gctggcagtg ttcctgcgcc ggttgcattc gattcctgtt tgtaattgtc cttttaacgg | 2040 |
| cgatcgcgta tttcgtctcg ctcaggcgca atcacgaatg aataacggtt tggttggtgc | 2100 |
| gagtgatttt tgatgacgag cgtaatggct gcctgttgaa caagtctgga agaaatgca | 2160 |
| taagcttttg ccattctcac cggattcagt cgtcactcat ggtgatttct cacttgataa | 2220 |
| ccttattttt gacgagggga aattaatagg ttgtattgat gttggacgag tcggaatcgc | 2280 |
| agaccgatac caggatcttg ccatcctatg gaactgcctc ggtgagtttt ctccttcatt | 2340 |
| acagaaacgg cttttcaaa aatatggtat tgataatcct gatatgaata aattgcagtt | 2400 |
| tcacttgatg ctcgatgagt ttttctgagg gcggatcccc ctcaagtcaa aagcctccgg | 2460 |
| tcggaggctt ttgactttct gctatggagg tcaggtatga ttttgcatta ggcaccccag | 2520 |
| gctttacact ttatgcttcc ggctcgtatg ttgtgtggaa ttgtgagcgg ataacaattt | 2580 |
| cacactttca tcaagtcaaa acactatata ggaacgaaac catgaacttc cctcgcgcgt | 2640 |
| cgcgcctgat gcaggcggcg gtcctcggtg gtctgatggc agtcagcgcc gcggccaccg | 2700 |
| ctcagaccaa cccatacgcc cgcggcccaa accctaccgc ggccagcctg aagcctctg | 2760 |
| ccggcccatt caccgtgcgc agcttcaccg tcagtcgccc gtcgggctat ggtgccggca | 2820 |
| ccgtctacta cccaaccaac gctggcggca ccgtcggcgc catcgcaatc gtgccgggct | 2880 |
| ataccgcccg ccagtcctcg atcaagtggt ggggcccacg tctggcctcc cacggcttcg | 2940 |
| ttgttatcac catcgacacc aactcgaccc tggaccagcc gtcctcccgc tcgagccagc | 3000 |
| agatggctgc tctgcgccag gtagcttcgc tgaacggcac cagctctagc ccaatctacg | 3060 |
| gcaaagtgga caccgctcgc atgggcgtga tgggttggtc catgggcggt ggtggttccc | 3120 |
| tgatctccgc tgctaataat ccttcccctga aggccgccgc cccgcaggcc ccatgggact | 3180 |
| cctcgaccaa cttctcgagc gtgaccgtgc cgaccctgat cttcgcttgc gaaaacgaca | 3240 |
| gcatcgctcc ggtgaactcc tccgcgctgc ctatctacga ctccatgagc cgcaacgcca | 3300 |
| agcaattcct ggaaatcaac ggcggttccc actcctgcgc taactcgggc aactcgaacc | 3360 |
| aagccctgat cggcaagaag ggcgtagcat ggatgaagcg tttcatggat aacgacaccc | 3420 |
| gttactcgac cttcgcctgc gaaaacccga actctactcg cgtcagcgac ttccgcactg | 3480 |
| cgaactgcag cggtggttct gaggaatctt acatgagcaa gggcgaggag ctctttaccg | 3540 |
| gcgtcgtccc cattctcgtt gagctggacg gcgacgtgaa cggacataag ttcagtgtct | 3600 |
| cgggcgaggg cgaaggagat gccacctatg gaagctaac cctgaagttc atctgcacaa | 3660 |
| ccggaagct gccggtcccc tggccgacgc tggttaccac cctgacctac ggcgtgcaat | 3720 |
| gcttctcgcg ctaccctgac cacatgaagc gccacgactt cttcaaatcc gctatgccgg | 3780 |
| agggctacgt ccaggaacgc accatattct tcaaggacga cggtaactac aagacgcgcg | 3840 |

```
ccgaagtcaa gttcgagggg gataccctcg tgaaccgaat cgagttgaag gggatcgact   3900
tcaaagaaga tggcaacatc ctcggccaca aactggagta caactacaat tcgcataacg   3960
tgtacatcat ggccgacaag cagaagaatg gcatcaaggt gaacttcaag attcgccaca   4020
acatcgagga cgggtccgtt cagctggccg accactatca gcagaacaca ccaattggag   4080
acggccccgt cctgctcccc gataaccatt acctttcgac acagtcggcg ctgtcgaagg   4140
acccgaacga aaagcgggac cacatggtgc tcctggagtt cgtcacggcg gccgggatca   4200
cgcacggaat ggacgaactc tacaagtag                                     4229
```

<210> SEQ ID NO 7
<211> LENGTH: 969
<212> TYPE: DNA
<213> ORGANISM: Artificial Sequence
<220> FEATURE:
<223> OTHER INFORMATION: osynthetic tphCII gene

<400> SEQUENCE: 7

```
atgcgtaacg aatctatccg tcgtcgtgaa gcgttaattg gtatcgctgc agcagttgca     60
gcaactggtt cactcgctca agtaaccaa ccactgaaaa tcgttgtgcc tttttctgca    120
ggtggtacag cggacgtatt accacgtctt gtcgctgaaa aaatccgtgc cgattatgct    180
ggtggtgtta tcatcgaaaa caaaccaggt gcaggtggta atattggtgc agatctagtt    240
ttccgtgctc caccagacgg tatgacggtt ttagcttcac cacctggtcc tatcgctatt    300
aatcacaatc tttatcaaaa attatctttc gatcctactc gttgggtacc agtaaccatt    360
ctggcaacag ttcctaacgt acttgtaatt aacccaaaac tacctgttaa agccttggc    420 gaatttatcg catacgcaaa agcaaatcca agaaagtaa ccgtagcgac tcaaggtgac    480
ggttctactt cacaccttac agcagcaatg tttatgcaat taactggtac agaactaact    540
gttatcccat acaaaggtac agcaccagct ttaatcgatc ttattggtgg taatgtagac    600
gtgtttttcg ataatatcag ctcttctgca acttatcacc aagcaggaaa agttcgtatt    660
cttgcagttg ctgatgaaca acgttcacaa attcttccac aagttccaac gttcgcagaa    720
caacagtggc cagcaatgca agctgtgaca ttttttctcag tagtggcacc tcctggtaca    780
tcagcagaaa tcgcacaaaa acttcaaaaa cagatggctc ttgcccttc ttcgaacgat    840 attcgtaagc acttccagga caaggtgct gtgccatgtg gttgggatcc aagtaaaact    900
gctcaattta ttcgtcagga aaccgaaaaa tggaagaaag tactcaaagc agcaaacgta    960
aaactttaa                                                             969
```

<210> SEQ ID NO 8
<211> LENGTH: 1242
<212> TYPE: DNA
<213> ORGANISM: Artificial Sequence
<220> FEATURE:
<223> OTHER INFORMATION: synthetic tphA2II gene

<400> SEQUENCE: 8

```
atgcaggaaa gcattattca atggcatggt gcgaccaaca cacgcgttcc atttggtatc     60
tatacagata ccgcaaatgc tgaccaagaa caacagcgta tttaccgtgg cgaagtatgg    120
aattaccttt gtttggaatc agaaatccca ggagcgggtg attttcgtac cacatttgcg    180
ggtgaaacac ctattgtcgt agttcgtgat gctgatcaag aaatttatgc tttcgaaaat    240
cgttgtgctc accgtggtgc tttaattgca ttagaaaaga gcggtcgtac tgattctttt    300
```

```
caatgtgttt atcatgcatg gtcatataac cgtcagggtg accttacggg tgtggctttc    360
gaaaaaggcg taaaaggtca gggtggtatg ccagctagtt tctgtaaaga agaacatggt    420
ccacgtaaac ttcgcgtagc agttttctgc ggcttggttt tcggttcttt ttctgaagac    480
gttccaagta ttgaagatta tttgggtccg gaaatttgtg aacgtatcga acgtgttctc    540
cataagcctg tagaagttat cggtcgtttt actcagaaat acctaataa ctggaaactt     600
tattttgaaa atgtaaaaga tagctaccat gcatctcttt tacacatgtt tttcacaact    660
ttcgaactga accgtttatc tcagaaaggc ggtgttattg tggatgagtc tggcggccat    720
catgtatcct atagtatgat tgatcgtggg gccaaggatg attcatataa agatcaagct    780
attcgttctg acaatgaacg ttatcgtttg aaagatccta gcttactaga aggttttgaa    840
gaattcgaag atggtgtaac gcttcaaatt cttagcgtat tcccagggtt tgttttgcaa    900
caaatccaaa acagtattgc agtgcgtcag ttattgccaa aaagtatttc tagttctgaa    960
ttgaactgga cttatttagg ttatgccgat gatagcgcag aacaacgtaa agttcgtctt    1020
aaacaagcta atctgattgg acctgctgga ttcatttcaa tggaagatgg tgcagtcggc    1080
ggtttcgtgc agcgtggtat tgcaggcgct gctaaccttg atgcagtaat cgaaatgggc    1140
ggtgatcatg aaggcagctc tgaaggtcgc gctactgaaa cttcagtacg tggcttttgg    1200
aaagcatatc gtaaacatat gggacaagaa atgcaggcat ga                      1242

<210> SEQ ID NO 9
<211> LENGTH: 465
<212> TYPE: DNA
<213> ORGANISM: Artificial Sequence
<220> FEATURE:
<223> OTHER INFORMATION: synthetic tphA3II gene

<400> SEQUENCE: 9
atgatcaatg aaatacagat cgcagcattt aatgcagcat atgcaaaaac tattgactct    60
gatgctatgg aacaatggcc taccttttt actaaagatt gccattattg tgtaacgaat    120
gtagataatc atgatgaggg tttagctgct ggtatagttt gggcagattc acaggacatg    180
ttgactgatc gtatctcagc tttgcgtgaa gcgaacattt acgaacgtca ccgctatcgt    240
cacatcttag gtctgccatc aattcaatca ggtgatgcaa cgcaggcatc agctagcaca    300
cctttcatgg ttcttcgtat catgcatact ggcgaaacgg aggttttcgc atcgggtgaa    360
tatctcgata aattcactac tattgatggt aaattgcgcc ttcaggaacg tattgctgtt    420
tgtgactcta cagtaaccga taccttaatg gcattgccat tatga                   465

<210> SEQ ID NO 10
<211> LENGTH: 951
<212> TYPE: DNA
<213> ORGANISM: Artificial Sequence
<220> FEATURE:
<223> OTHER INFORMATION: synthetic tphBII gene

<400> SEQUENCE: 10
atgaacgcaa ttgttcaccg ccgtcttgca cttgcaattg gtgatccaca tggtattggt    60
cctgaaatcg cattgaaagc tcttcaacag ctttcggtaa ctgaacgtag cttaattaaa    120
gtatacggtc cgtggtctgc acttgaacaa gcagcacgcg tttgcgaaat ggaaccactc    180
ttacaagata tcgtacacga agaagcaggt accttgaccc aaccagtaca gtggggtgaa    240
attacaccac aagctggtct tagtacagta caatcagcta ctgctgcgat ccgtgcatgt    300
gaaaatggtg aggtagatgc agttattgcg tgtccacacc atgaaactgc aatccaccgt    360
```

```
gctggtatcg ccttctctgg ttatccaagc cttttagcga atgtgttggg tatgaacgaa      420
gatcaagttt ttcttatgtt ggttggtgct ggtcttcgta tcgttcatgt gactctacac      480
gaatctgtac gttctgcact tgaacgtctt tctccacaac ttgttgtaaa tgcagcacaa      540
gcagcagttc aaacctgtac attgcttggt gttcctaaac cgaaagtggc agtgttcggc      600
attaacccac atgcatcaga aggtcaactt ttcggcttgg aagatagcca aattaccgtt      660
ccagcagttg aaacccttcg taaacgtggt ctagctgttg atggtccaat gggtgcggat      720
atggtactgg cacaacgtaa acatgattta tatgttgcga tgcttcatga tcagggtcat      780
ataccaatta aacttcttgc accaaatggt gcgagtgctc tctcaatcgg tggtcgtgtt      840
gtattgtcat cagttggaca cggcagcgca atggacatcg ctggccgtgg cgtagctgat      900
gccactgctc ttttacgtac cattgctctt cttggcgctc agccagtttg a               951

<210> SEQ ID NO 11
<211> LENGTH: 1011
<212> TYPE: DNA
<213> ORGANISM: Artificial Sequence
<220> FEATURE:
<223> OTHER INFORMATION: synthetic tphA1II gene

<400> SEQUENCE: 11
atgaaccatc aaatccacat ccatgactca gatattgcat ttccatgtgc acctggtcaa       60
tcagttttgg atgcggcctt acaagcaggt atcgaattgc cttatagctg ccgtaaaggt      120
tcatgtggga attgtgcaag tactctttta gatggtaata ttgcatcttt caacggtatg      180
gctgttcgta atgaattatg tgcgtctgaa caagtgttat tgtgtggttg cacggcggca      240
tctgatatac gtattcatcc ttcttctttc cgtcgtcttg acccagaagc tcgtaaacgt      300
ttcactgcta aggtatattc aaatactctt gctgctccag atgtatctct tctccgtctc      360
cgtttacctg ttggtaaacg tgctaaattt gaagctggtc aatatttact aatccactta      420
gatgacggtg agagccgtag ctacagcatg gcaaatccac acatgaatc tgatggtatc      480 accttacatg ttcgtcatgt tccaggtggg cgttttagta ctattgtaca acaattgaaa      540
tcaggagata ctttggacat tgaattacct tttggttcta ttgcgcttaa acctgatgac      600
gctcgtcctc tgatctgtgt agctggtggt accggctttg ctccaatcaa atccgtttta      660
gacgatctcg cgaaacgtaa agtacagcgc gatatcacac ttatctgggg cgcacgcaat      720
ccatctggct tatatcttcc atcagctatc gataagtggc gtaaggtatg gccacaattc      780
cgttacatcg ccgctatcac tgatcttggg gatatgccag ctgatgcaca cgctggtcgt      840
gtggacgacg cattacgtac tcattttggt aatctgcatg atcatgttgt tcattgttgt      900
ggttcgcctg ctctagttca aagtgtccgt acagccgcct cggacatggg tctactagcg      960
caagatttcc atgcagatgt atttgcaact ggtcctacag gtcaccacta g              1011

<210> SEQ ID NO 12
<211> LENGTH: 489
<212> TYPE: DNA
<213> ORGANISM: Artificial Sequence
<220> FEATURE:
<223> OTHER INFORMATION: synthetic tpiB gene

<400> SEQUENCE: 12
atgaaaatta aaagtcaaaa agattttttt tctggtttga tgttccttgc agttggttta       60
gcatttgcaa ttggtgcttc aaattatact attggtactg gtgctcgtat gggtccaggt      120
```

```
tatttccctc ttatacttgg tgtactgatg gcgattctag gtgcagctat ctgtgttggt      180
ggtcttacta aaggtccaga gggtggtgat aaaattggta atgggcatg gcgtcaagtt       240 ttttttatct tggcagcaaa ttttgcattc ggcattttgt tagtgggtgt accagcagtt      300
ggtattccac aatttggtct tattatcgca atttatgcgt tagtcttcat cgcgtctttg      360
ggtggccact ctttcaactt caaagaaacc gcgatccttg caacggtgct tgcagttggt      420
tcttacttcg cttttgtttg ggcattaaac ttacaattcc cagtatggcc atcatttatc     480
gcgggttaa                                                              489
```

```
<210> SEQ ID NO 13
<211> LENGTH: 1512
<212> TYPE: DNA
<213> ORGANISM: Artificial Sequence
<220> FEATURE:
<223> OTHER INFORMATION: synthetic tpiA gene

<400> SEQUENCE: 13
atggatctta ttcaaaactt aagtaccggc ttcggtgtgg ctttcacttt ccaaaatttg       60
atttattgtt tcgttggttg tcttttaggt actttaattg gcgtacttcc aggcattggt      120
ccagttgcta caattgcaat gttattgcct gcaacctatg ctttaccacc agtggctgca      180
ttgattatgt tggctggtat ctactatggt gcgcagtatg gtggtagtac tactgctatt      240
ttggtaaatc ttccgggtga atcttcttct gtagtcaccg ttatcgatgg ttaccaaatg     300
gctcgtaaag gtcgtgcagg tccagcgctt gctgctgctg gtattggttc ttttttcgca     360
ggttgtgttg gtacagtgat cttagcggct ttcgctccac ctctcacgga agttgcattc     420
aagtttggac ctgcagagta tttttctta atgacattgg gtctaattgg tgcagttgtc      480
cttgcttcag gctcttttgct caaagcaatt gcaatgatcg tactcggtct tttgcttggc    540
atggttggta cggacgtaaa ttcaggtgta gcgcgttact catttgacat tccagagcta     600
acagatggta ttgattttgt tgtgatcgca atgggtgttt ttggttacgg tgaaattatt      660
gcaaatcttt caaagcctga tgatgaacgt gaggttttg cagcgaaagt gactggtctt      720
cttccaacaa gtgaagactt caaacgtatg ttgccagcaa tgttgcgtgg tacagcatta    780
ggttcagctt aggaattttt gccaggtggt ggtgctatgt tgagtgcatt tgcagcttat     840
acaattgaaa aaaaaaccaa attaaaaacct ggtgaagtac catttggtca gggcaatatt    900
cgtggcgttt gcgctccgga atcagcaaac aacgctggta gtcaaacatc tttcattcca    960
ctgttaacat tgggcattcc ttccaaacgcc gtaatggctc tcatggtagg cgcaatgact   1020
attcacaaca ttcaaccagg accacaagtg atgacatcta accctgaact attttggggt   1080
cttattgcaa gcatgtggat tggtaatttg atgttaatta ttttgaacct accacttatc   1140
ggtgtgtgga tcaagttgct tacagtacca tatcgttggt tgtttccatc tatcgtatta   1200
ttttgtgcaa ttggtgtgta tggtactaat aacaacgttt gggatgtttg atggtaggt    1260 atttttggtt tcattggtta tgtattccac aagttaggga ctgaacctgc tcctttgttg    1320
ttgggtttca ttttaggtcc aatgatggaa gaaaaccttc gccgtgctct attgctatcg   1380
cgtggcgact ggtctgtatt tgttacgcgt ccaattagtg catgcttact ggcagcggct   1440
gttgtgcttc ttgtaatcgt tcttatgcct gcagttaaga ataaacgtga agaggccttt   1500
gtagaagatt ga                                                       1512
```

```
<210> SEQ ID NO 14
<211> LENGTH: 8850
```

<212> TYPE: DNA
<213> ORGANISM: Artificial Sequence
<220> FEATURE:
<223> OTHER INFORMATION: local chromosomal sequence in strain IP103

<400> SEQUENCE: 14

| | | | | | |
|---|---|---|---|---|---|
| gtttaaacca | aattacgcag | ctcattcgca | gtattgcgta | ataaaggtaa | aacttgatcg | 60 |
| ataagatact | gtggctgcac | ccgattggtt | tgtgacatac | aattaagtgc | tgcaatggta | 120 |
| agccccgtgt | cgtttaaaac | gggtaccgca | atcgcaatca | gacccagttc | atgttcctca | 180 |
| gtagacaaac | agtagtccga | ttgccgaaca | gcatctaatg | tttctaaaaa | agtatgttca | 240 |
| tcggtaatgg | tataaggcgt | gaggcgcttc | agaccatatt | tttcaatcca | ttcaatttgt | 300 |
| acttcacgat | ccagaacaga | agtaatact | ttaccggtag | aggtggcgtg | ggcaggcaaa | 360 |
| cgattaccca | aatgcatccc | ataggggctc | acgcgaagat | tatcttgctg | gggtaaataa | 420 |
| ctacgcgcaa | caggtacaac | ttcatgctca | tcgagcacca | caattgaaaa | ggtgaggctg | 480 |
| gtttgagcac | acagtagatt | taaaaatgac | tgtgccactt | tgggtaaatg | tgccgagctt | 540 |
| aaataagaac | tagaaaaacg | taaaacacga | tgtgtaagcc | aaaaatagtg | ctcatcggta | 600 |
| tctaaataac | ccaaaaattt | aagtgtcttt | aaataacgcc | gtgcagctgt | tctgcttata | 660 |
| ccagtacgct | ctgcaacctg | tgtcacgttc | agtcgttgtc | tgtcaattcc | aaatgcttct | 720 |
| aaaagcgcta | agcctttggc | caagcctgca | atgtaatctt | ccgtacgtat | ttcttcactt | 780 |
| gaatggggat | gtgcaaggta | ttggtgatgt | tgttccataa | cattcaaatc | caaaatggtt | 840 |
| ttgtccgatc | atcggacagt | tgtaatgcta | atcggataat | tttgagcctt | gattatagat | 900 |
| gtcttttaa | tgaggcggta | ctttaaaaat | agaaaatagc | aaggatgatg | ttatgcaaac | 960 |
| tatgaaaacc | aaagttgcaa | ttattggttc | tggcccagcg | ggattactac | tcggtcaact | 1020 |
| gctttacaaa | gctggaattg | aacacgttat | tgtggaacag | cgaagtgccg | attacgttgc | 1080 |
| atcacgcatt | cgtgcaggaa | ttttagagca | agtatcggtc | gatttactcg | agcaagctgg | 1140 |
| agttgatcag | aacctcaaag | aaaaaggatt | gccacattcg | ggcattgaaa | ttctgaccaa | 1200 |
| tggccaaaaa | ttccgtgtcg | atttatcggc | attgactcaa | ggtaaacaag | tcacggtata | 1260 |
| tgggcagacc | gaagttacta | aagatttaat | gcaagcacgt | gagcaggctg | gtctttgctc | 1320 |
| attttatgaa | tcgaatgatg | ttcaaattca | tgattttat | aatgcgccaa | aagtgacttt | 1380 |
| tgaatccaac | ggaactcact | atcaaatcga | atgtgatttc | attgcaggat | gtgatggtta | 1440 |
| tcatggcgtg | tgccgtgcta | gtgtgcctca | agataaaatt | aaaacctttg | aaaaggtcta | 1500 |
| tccatttggt | tggttaggtg | tacttgccga | tgtgccgcct | gtggcagacg | agttaattta | 1560 |
| tgttcaatca | gagcgtggtt | ttgcactgtg | tagcatgcgc | tcagaaacgc | gaagccgata | 1620 |
| ttacattcaa | gttcctttaa | ccgatcacgt | agaaaactgg | tcggatgatc | aattttggga | 1680 |
| agagcttaag | aatcgcctcg | accctgaaag | ctgcgaaaaa | ctcgttacag | gcccttcaat | 1740 |
| tgagaaaagt | attgcacctt | tgcggagctt | tgtcacagaa | ccgatgcgat | ttggaaaatt | 1800 |
| attcttagct | ggtgatgccg | cacatattgt | tccaccaacg | ggtgccaaag | gattgaatct | 1860 |
| tgcagcttca | gatattgcat | atttgtcgag | tgcgctcatt | gaatttaca | cgcaaggatc | 1920 |
| tgagcaaggt | atagatcaat | actcagaaaa | atgcttgcaa | cgtgtatgga | aagcagagcg | 1980 |
| tttttcatgg | tggatgaccc | atttgttaca | tcgctttgaa | accgaaagcg | agtttgatca | 2040 |
| taaaattaaa | caagcagaat | tgagctatat | cttaggttct | acggcaggtc | agaccacact | 2100 |
| cgctgaaaac | tatgtgggtt | taccctatga | aatcaaatcc | cttgactatt | taaacatgc | 2160 |

```
cagctaacca gacatcaaat aaaacgaaag gctcagtcga aagactgggc ctttcgtttt    2220
atctgttgtt tgtcggtgaa cgctctcatt aattaatcca gaggcatgag ctgttgacaa    2280
ttaatcatcg gctcgtataa tgtgtggaat tgtgagcgga taacaatttc acacaggaga    2340
gtctatatat gcgtaacgaa tctatccgtc gtcgtgaagc gttaattggt atcgctgcag    2400
cagttgcagc aactggttca ctcgctcaaa gtaaccaacc actgaaaatc gttgtgcctt    2460
tttctgcagg tggtacagcg gacgtattac cacgtcttgt cgctgaaaaa atccgtgccg    2520
attatgctgg tggtgttatc atcgaaaaca aaccaggtgc aggtggtaat attggtgcag    2580
atctagtttt ccgtgctcca ccagacggta tgacggtttt agcttcacca cctggtccta    2640
tcgctattaa tcacaatctt tatcaaaaat tatctttcga tcctactcgt tgggtaccag    2700
taaccattct ggcaacagtt cctaacgtac ttgtaattaa cccaaaacta cctgttaaaa    2760
gccttggcga atttatcgca tacgcaaaag caaatccaaa gaaagtaacc gtagcgactc    2820
aaggtgacgg ttctacttca caccttacag cagcaatgtt tatgcaatta actggtacag    2880
aactaactgt tatcccatac aaaggtacag caccagcttt aatcgatctt attggtggta    2940
atgtagacgt gttttcgat aatatcagct cttctgcaac ttatcaccaa gcaggaaaag    3000
ttcgtattct tgcagttgct gatgaacaac gttcacaaat tcttccacaa gttccaacgt    3060
tcgcagaaca acagtggcca gcaatgcaag ctgtgacatt tttctcagta gtggcacctc    3120
ctggtacatc agcagaaatc gcacaaaaac ttcaaaaaca gatggctctt gccctttctt    3180
cgaacgatat tcgtaagcac ttccaggaac aaggtgctgt gccatgtggt tgggatccaa    3240
gtaaaactgc tcaatttatt cgtcaggaaa ccgaaaaatg gaagaaagta ctcaaagcag    3300
caaacgtaaa actttaagag aggaaagcaa tgcaggaaag cattattcaa tggcatggtg    3360
cgaccaacac acgcgttcca tttggtatct atacagatac cgcaaatgct gaccaagaac    3420
aacagcgtat ttaccgtggc gaagtatgga attaccttg tttggaatca gaaatcccag    3480
gagcgggtga ttttcgtacc acatttgcgg gtgaaacacc tattgtcgta gttcgtgatg    3540
ctgatcaaga aatttatgct ttcgaaaatc gttgtgctca ccgtggtgct ttaattgcat    3600
tagaaaagag cggtcgtact gattcttttc aatgtgttta tcatgcatgg tcatataacc    3660
gtcagggtga ccttacgggt gtggctttcg aaaaaggcgt aaaaggtcag ggtggtatgc    3720
cagctagttt ctgtaaagaa gaacatggtc acgtaaaact tcgcgtagca gttttctgcg    3780
gcttggtttt cggttctttt tctgaagacg ttccaagtat tgaagattat ttgggtccgg    3840
aaatttgtga acgtatcgaa cgtgttctcc ataagcctgt agaagttatc ggtcgtttta    3900
ctcagaaatt acctaataac tggaaacttt attttgaaaa tgtaaaagat agctaccatg    3960
catctctttt acacatgttt ttcacaactt tcgaactgaa ccgtttatct cagaaaggcg    4020
gtgttattgt ggatgagtct gcggccatc atgtatccta tagtatgatt gatcgtgggg    4080
ccaaggatga ttcatataaa gatcaagcta ttcgttctga caatgaacgt atcgtttga    4140 aagatcctag cttactagaa ggttttgaag aattcgaaga tggtgtaacg cttcaaattc    4200
ttagcgtatt cccagggttt gttttgcaac aaatccaaaa cagtattgca gtgcgtcagt    4260
tattgccaaa aagtatttct agttctgaat tgaactggac ttatttaggt tatgccgatg    4320
atagcgcaga acaacgtaaa gttcgtctta acaagctaa tctgattgga cctgctggat    4380
tcatttcaat ggaagatggt gcagtcggcg gtttcgtgca gcgtggtatt gcaggcgctg    4440
ctaaccttga tgcagtaatc gaaatgggcg gtgatcatga aggcagctct gaaggtcgcg    4500
ctactgaaac ttcagtacgt ggcttttgga agcatatcg taaacatatg ggacaagaaa    4560
```

```
tgcaggcatg aggagtccct aaacaatgat caatgaaata cagatcgcag catttaatgc    4620
agcatatgca aaaactattg actctgatgc tatggaacaa tggcctacct tttttactaa    4680
agattgccat tattgtgtaa cgaatgtaga taatcatgat gagggtttag ctgctggtat    4740
agtttgggca gattcacagg acatgttgac tgatcgtatc tcagctttgc gtgaagcgaa    4800
catttacgaa cgtcaccgct atcgtcacat cttaggtctg ccatcaattc aatcaggtga    4860
tgcaacgcag gcatcagcta gcacaccttt catggttctt cgtatcatgc atactggcga    4920
aacggaggtt ttcgcatcgg gtgaatatct cgataaattc actactattg atggtaaatt    4980
gcgccttcag gaacgtattg ctgtttgtga ctctacagta accgatacct taatggcatt    5040
gccattatga aaggaggtaa caatgaacgc aattgttcac cgccgtcttg cacttgcaat    5100
tggtgatcca catggtattg gtcctgaaat cgcattgaaa gctcttcaac agctttcggt    5160
aactgaacgt agcttaatta agtatacgg tccgtggtct gcacttgaac aagcagcacg    5220
cgtttgcgaa atggaaccac tcttacaaga tatcgtacac gaagaagcag gtaccttgac    5280
ccaaccagta cagtggggtg aaattacacc acaagctggt cttagtacag tacaatcagc    5340
tactgctgcg atccgtgcat gtgaaaatgg tgaggtagag gcagttattg cgtgtccaca    5400
ccatgaaact gcaatccacc gtgctggtat cgccttctct ggttatccaa gcctttagc    5460 gaatgtgttg ggtatgaacg aagatcaagt ttttcttatg ttggttggtg ctggtcttcg    5520
tatcgttcat gtgactctac acgaatctgt acgttctgca cttgaacgtc tttctccaca    5580
acttgttgta aatgcagcac aagcagcagt tcaaacctgt acattgcttg gtgttcctaa    5640
accgaaagtg gcagtgttcg gcattaaccc acatgcatca gaaggtcaac ttttcggctt    5700
ggaagatagc caaattaccg ttccagcagt tgaaaccctt cgtaaacgtg gtctagctgt    5760
tgatggtcca atgggtgcgg atatggtact ggcacaacgt aaacatgatt tatatgttgc    5820
gatgcttcat gatcagggtc atataccaat taaacttctt gcaccaaatg gtgcgagtgc    5880
tctctcaatc ggtggtcgtg ttgtattgtc atcagttgga cacggcagcg caatggacat    5940
cgctggccgt ggcgtagctg atgccactgc tcttttacgt accattgctc ttcttggcgc    6000
tcagccagtt tgaggtccct cccaaatgaa ccatcaaatc cacatccatg actcagatat    6060
tgcatttcca tgtgcacctg tcaatcagt tttggatgcg gccttacaag caggtatcga    6120
attgccttat agctgccgta aaggttcatg tgggaattgt gcaagtactc ttttagatgg    6180
taatattgca tctttcaacg gtatggctgt tcgtaatgaa ttatgtgcgt ctgaacaagt    6240
gttattgtgt ggttgcacgg cggcatctga tatacgtatt catccttctt cttttccgtcg    6300 tcttgaccca gaagctcgta acgtttcac tgctaaggta tattcaaata ctcttgctgc    6360
tccagatgta tctcttctcc gtctccgttt acctgttggt aaacgtgcta atttgaagc    6420 tggtcaatat ttactaatcc acttagatga cggtgagagc cgtagctaca gcatggcaaa    6480
tccaccacat gaatctgatg gtatcacctt acatgttcgt catgttccag gtgggcgttt    6540
tagtactatt gtacaacaat tgaaatcagg agatactttg acattgaat tacccttttgg    6600 ttctattgcg cttaaacctg atgacgctcg tcctctgatc tgtgtagctg gtggtaccgg    6660
ctttgctcca atcaaatccg ttttagacga tctcgcgaaa cgtaaagtac agcgcgatat    6720
cacacttatc tggggcgcac gcaatccatc tggcttatat cttccatcag ctatcgataa    6780
gtggcgtaag gtatgccac aattccgtta catcgccgct atcactgatc ttggggatat    6840
gccagctgat gcacacgctg gtcgtgtgga cgacgcatta cgtactcatt ttggtaatct    6900
```

-continued

```
gcatgatcat gttgttcatt gttgtggttc gcctgctcta gttcaaagtg tccgtacagc    6960
cgcctcggac atgggtctac tagcgcaaga tttccatgca gatgtatttg caactggtcc    7020
tacaggtcac cactagggtt aaaacaaaaa gagagcgatt agtcgctctc tttttttatct   7080 cggctgtgtt tatttacaag tgaaattctc ggcttttttca ctgtcacctg taccgttata   7140
acgtgcgatt tttggatatg acatagtgg tcgagttcga ttggccgacc agctcgatgg     7200
taactcgcta ttgatttcgc cacttgcatt accgacaccg cgtgcagaag cgagaatttg    7260
atctggtgct tgaccatatt ctacccagtt caccaaagca gtaagtgcat caaactggtc    7320
ggtcgcaagc ccaccccgcg aatgattcat tcccggaacg cgataaaaac gagcaaaact    7380
ttgtgcgtca cccaaactgc tgctcttgta ttttgccatc agtttatcgt accagttttg    7440
tgtgtcatct accgaaaata cgccatctgc tgtgccttgc accacaatca ttttaccgcc    7500
atgcaagcgt aatttatcca gattgagctc atctggcggg atcataaatg acatcgcgct    7560
ttctgaatag gtcgaattgg ttgcagaaag ttttgggtaa tctgtatcaa aattatagtt    7620
aaaggcaaat tttcgtgaat tttgcacaat tgttggatct ggtggtaccgt gaaatataat   7680 gcctaccgct accgggtcgc gtgccgtacc cacagaagaa acaaatttcc agcttgccca    7740
attgctgcca gtaatcccg gatcgtaagg ctgggtcgca tacaatgctt cgccagatga     7800
attgacaggg ccgcggtaaa tattagccac gacatcgatc tggtctttac tcaaacagct    7860
tccatcacgt gaacccgagc agacaggcac atctttatga atatcaaagg cggttcgaca    7920
ggcttcaacg tcttgtacca taccatctgc tacaccatcg agtgcatcac agcgtgttaa    7980
aatcgcattg gcaagtacgt tacgttctgc ataggtgagt gcagtgctta aatcatttc    8040 atcggtggca acacgacgta attgctgcgc cgtgtatagc tgtgccgctg ctgcacgtgg    8100
tagatgaaat ccgggtgtgc ttgccaagat gccatcgtac tgatcgccta ggcgtgttgc    8160
agccatcatg gcatgtcgac cgccgttaga cgtacctcct gcataagatc gatctggcaa    8220
tttaccgtaa gctgttttaa tcagatcttt ggccataggc gttaactttg taatagcacc    8280
ataaccatag ttgatgcgag cttgcggatc taaaccaaaa agaggatttt gtgcagatga    8340
atgtccggca tcggatgaaa ttaccgcgaa tccgtctttt aaagcattgc ttaacatccc    8400
gccgctgccc acttgtccgg tcgctgtggc gatgttgccg tcggtaccgc catttccttg    8460
atatagaaaa cgtccgttcc agctcaccgg aagtcgcatt tcaaagccaa tctgataggt    8520
ttgaccatcg attgggctaa tacgttgctc catataacct ttgaccaaac aatgcgccgg    8580
aatatttttc cccacgacgg tcagagcgcc tgcattttgt aaagttgcac tttcaactac    8640
ggtggtatca aatttgaaac cgcttaaatc tgtacaactg cctttgagct gagcacctac    8700
tgctgggctt aattgtggaa tactttggct cgactgtgcc gtatcatgat cgttattgtc    8760
attacatgca gctacactga tgcagacgcc gagcaatgca gcatgtttaa aaaaatgttg    8820
aggttttttc attgcaatat ccttatgcct                                     8850
```

<210> SEQ ID NO 15
<211> LENGTH: 13236
<212> TYPE: DNA
<213> ORGANISM: Artificial Sequence
<220> FEATURE:
<223> OTHER INFORMATION: nucleotide sequence of the local chromosomal
      sequence in strain IP131

<400> SEQUENCE: 15

```
gtttaaacca aattacgcag ctcattcgca gtattgcgta ataaaggtaa aacttgatcg     60
ataagatact gtggctgcac ccgattggtt tgtgacatac aattaagtgc tgcaatggta    120
agcccctgtg cgtttaaaac gggtaccgca atcgcaatca gacccagttc atgttcctca    180
gtagacaaac agtagtccga ttgccgaaca gcatctaatg tttctaaaaa agtatgttca    240
tcggtaatgg tataaggcgt gaggcgcttc agaccatatt tttcaatcca ttcaatttgt    300
acttcacgat ccagaacaga agtaatact ttaccggtag aggtggcgtg ggcaggcaaa     360
cgattaccca aatgcatccc ataggggctc acgcgaagat tatcttgctg gggtaaataa    420
ctacgcgcaa caggtacaac ttcatgctca tcgagcacca caattgaaaa ggtgaggctg    480
gtttgagcac acagtagatt taaaaatgac tgtgccactt tgggtaaatg tgccgagctt    540
aaataagaac tagaaaaacg taaaacacga tgtgtaagcc aaaaatagtg ctcatcggta    600
tctaaataac ccaaaaattt aagtgtcttt aaataacgcc gtgcagctgt tctgcttata    660
ccagtacgct ctgcaacctg tgtcacgttc agtcgttgtc tgtcaattcc aaatgcttct    720
aaaagcgcta agccttttggc caagcctgca atgtaatctt ccgtacgtat ttcttcactt    780
gaatggggat gtgcaaggta ttggtgatgt tgttccataa cattcaaatc caaaatggtt    840
ttgtccgatc atcggacagt tgtaatgcta atcggataat tttgagcctt gattatagat    900
gtcttttta tgaggcggta cttaaaaat agaaaatagc aaggatgatg ttatgcaaac      960
tatgaaaacc aaagttgcaa ttattggttc tggcccagcg ggattactac tcggtcaact   1020
gctttacaaa gctggaattg aacacgttat tgtggaacag cgaagtgccg attacgttgc   1080
atcacgcatt cgtgcaggaa ttttagcaga agtatcggtc gatttactcg agcaagctgg   1140
agttgatcag aacctcaaag aaaaaggatt gccacattcg ggcattgaaa ttctgaccaa   1200
tggccaaaaa ttccgtgtcg atttatcggc attgactcaa ggtaaacaag tcacggtata   1260
tgggcagacc gaagttacta aagatttaat gcaagcacgt gagcaggctg gtctttgctc   1320
attttatgaa tcgaatgatg ttcaaattca tgattttat aatgcgccaa aagtgacttt    1380
tgaatccaac ggaactcact atcaaatcga atgtgatttc attgcaggat gtgatggtta   1440
tcatggcgtg tgccgtgcta gtgtgcctca agataaaatt aaaaccttg aaaaggtcta    1500
tccatttggt tggttaggtg tacttgccga tgtgccgcct gtggcagacg agttaattta   1560
tgttcaatca gagcgtggtt ttgcactgtg tagcatgcgc tcagaaacgc gaagccgata   1620
ttacattcaa gttcctttaa ccgatcacgt agaaaactgg tcggatgatc aattttggga   1680
agagcttaag aatcgcctcg accctgaaag ctgcgaaaaa ctcgttacag gcccttcaat   1740
tgagaaaagt attgcaccctt tgcggagctt tgtcacagaa ccgatgcgat ttggaaaatt   1800
attcttagct ggtgatgccg cacatattgt tccaccaacg ggtgccaaag gattgaatct   1860
tgcagcttca gatattgcat atttgtcgag tcgctcatt gaattttaca cgcaaggatc    1920
tgagcaaggt atagatcaat actcagaaaa atgcttgcaa cgtgtatgga agcagagcg   1980
tttttcatgg tggatgaccc atttgttaca tcgctttgaa accgaaagcg agtttgatca   2040
taaaattaaa caagcagaat tgagctatat cttaggttct acggcaggtc agaccacact   2100
cgctgaaaac tatgtgggtt taccctatga atcaaatcc cttgactatt taaaacatgc    2160
cagctaacca gacatcaaat aaaacgaaag gctcagtcga aagactgggc ctttcgtttt   2220
atctgttgtt tgtcggtgaa cgctctcatt aattaatcca gaggcatgag ctgttgacaa   2280
```

```
ttaatcatcg gctcgtataa tgtgtggaat tgtgagcgga taacaatttc acacaggaga    2340
gtctatatat gcgtaacgaa tctatccgtc gtcgtgaagc gttaattggt atcgctgcag    2400
cagttgcagc aactggttca ctcgctcaaa gtaaccaacc actgaaaatc gttgtgcctt    2460
tttctgcagg tggtacagcg gacgtattac cacgtcttgt cgctgaaaaa atccgtgccg    2520
attatgctgg tggtgttatc atcgaaaaca aaccaggtgc aggtggtaat attggtgcag    2580
atctagtttt ccgtgctcca ccagacggta tgacggtttt agcttcacca cctggtccta    2640
tcgctattaa tcacaatctt tatcaaaaat tatctttcga tcctactcgt tgggtaccag    2700
taaccattct ggcaacagtt cctaacgtac ttgtaattaa cccaaaacta cctgttaaaa    2760
gccttggcga atttatcgca tacgcaaaag caaatccaaa gaaagtaacc gtagcgactc    2820
aaggtgacgg ttctacttca caccttacag cagcaatgtt tatgcaatta actggtacag    2880
aactaactgt tatcccatac aaaggtacag caccagcttt aatcgatctt attggtggta    2940
atgtagacgt gttttcgat aatatcagct cttctgcaac ttatcaccaa gcaggaaaag    3000
ttcgtattct tgcagttgct gatgaacaac gttcacaaat tcttccacaa gttccaacgt    3060
tcgcagaaca acagtggcca gcaatgcaag ctgtgacatt tttctcagta gtggcacctc    3120
ctggtacatc agcagaaatc gcacaaaaac ttcaaaaaca gatggctctt gccctttctt    3180
cgaacgatat tcgtaagcac ttccaggaac aaggtgctgt gccatgtggt tgggatccaa    3240
gtaaaactgc tcaatttatt cgtcaggaaa ccgaaaaatg gaagaaagta ctcaaagcag    3300
caaacgtaaa actttaagag aggaaagcaa tgcaggaaag cattattcaa tggcatggtg    3360
cgaccaacac acgcgttcca tttggtatct atacagatac cgcaaatgct gaccaagaac    3420
aacagcgtat ttaccgtggc gaagtatgga attacctttg tttggaatca gaaatcccag    3480
gagcgggtga ttttcgtacc acatttgcgg gtgaaacacc tattgtcgta gttcgtgatg    3540
ctgatcaaga aatttatgct ttcgaaaatc gttgtgctca ccgtggtgct ttaattgcat    3600
tagaaaagag cggtcgtact gattcttttc aatgtgttta tcatgcatgg tcatataacc    3660
gtcagggtga ccttacgggt gtggctttcg aaaaaggcgt aaaaggtcag ggtggtatgc    3720
cagctagttt ctgtaaagaa gaacatggtc cacgtaaact tcgcgtagca gttttctgcg    3780
gcttggtttt cggttctttt tctgaagacg ttccaagtat tgaagattat ttgggtccgg    3840
aaatttgtga acgtatcgaa cgtgttctcc ataagcctgt agaagttatc ggtcgtttta    3900
ctcagaaatt acctaataac tggaaacttt attttgaaaa tgtaaaagat agctaccatg    3960
catctctttt acacatgttt ttcacaactt tcgaactgaa ccgtttatct cagaaaggcg    4020
gtgttattgt ggatgagtct ggcggccatc atgtatccta gtatgatt gatcgtgggg    4080 ccaaggatga ttcatataaa gatcaagcta ttcgttctga caatgaacgt atcgtttga    4140 aagatcctag cttactagaa ggttttgaag aattcgaaga tggtgtaacg cttcaaattc    4200
ttagcgtatt cccagggttt gttttgcaac aaatccaaaa cagtattgca gtgcgtcagt    4260
tattgccaaa aagtatttct agttctgaat tgaactggac ttatttaggt tatgccgatg    4320
atagcgcaga caacgtaaa gttcgtctta aacaagctaa tctgattgga cctgctggat    4380
tcatttcaat ggaagatggt gcagtcggcg gtttcgtgca gcgtggtatt gcaggcgctg    4440
ctaaccttga tgcagtaatc gaaatgggcg gtgatcatga aggcagctct gaaggtcgcg    4500
ctactgaaac ttcagtacgt ggcttttgga aagcatatcg taaacatatg ggacaagaaa    4560
tgcaggcatg aggagtccct aaacaatgat caatgaaata cagatcgcag catttaatgc    4620
agcatatgca aaaactattg actctgatgc tatggaacaa tggcctacct tttttactaa    4680
```

```
agattgccat tattgtgtaa cgaatgtaga taatcatgat gagggtttag ctgctggtat    4740
agtttgggca gattcacagg acatgttgac tgatcgtatc tcagctttgc gtgaagcgaa    4800
catttacgaa cgtcaccgct atcgtcacat cttaggtctg ccatcaattc aatcaggtga    4860
tgcaacgcag gcatcagcta gcacaccttt catggttctt cgtatcatgc atactggcga    4920
aacggaggtt ttcgcatcgg gtgaatatct cgataaattc actactattg atggtaaatt    4980
gcgccttcag gaacgtattg ctgtttgtga ctctacagta accgatacct taatggcatt    5040
gccattatga aaggaggtaa caatgaacgc aattgttcac cgccgtcttg cacttgcaat    5100
tggtgatcca catggtattg gtcctgaaat cgcattgaaa gctcttcaac agctttcggt    5160
aactgaacgt agcttaatta aagtatacgg tccgtggtct gcacttgaac aagcagcacg    5220
cgtttgcgaa atggaaccac tcttacaaga tatcgtacac gaagaagcag gtaccttgac    5280
ccaaccagta cagtggggtg aaattacacc acaagctggt cttagtacag tacaatcagc    5340
tactgctgcg atccgtgcat gtgaaaatgg tgaggtagag gcagttattg cgtgtccaca    5400
ccatgaaact gcaatccacc gtgctggtat cgccttctct ggttatccaa gccttttagc    5460
gaatgtgttg ggtatgaacg aagatcaagt tttcttatg ttggttggtg ctggtcttcg    5520
tatcgttcat gtgactctac acgaatctgt acgttctgca cttgaacgtc tttctccaca    5580
acttgttgta aatgcagcac aagcagcagt tcaaacctgt acattgcttg gtgttcctaa    5640
accgaaagtg gcagtgttcg gcattaaccc acatgcatca gaaggtcaac ttttcggctt    5700
ggaagatagc caaattaccg ttccagcagt tgaaacccct tcgtaaacgtg gtctagctgt    5760 tgatggtcca atgggtgcgg atatggtact ggcacaacgt aaacatgatt tatatgttgc    5820
gatgcttcat gatcagggtc atataccaat taaacttctt gcaccaaatg gtgcgagtgc    5880
tctctcaatc ggtggtcgtg ttgtattgtc atcagttgga cacggcagcg caatggacat    5940
cgctggccgt ggcgtagctg atgccactgc tcttttacgt accattgctc ttcttggcgc    6000
tcagccagtt tgaggtccct cccaaatgaa ccatcaaatc cacatccatg actcagatat    6060
tgcatttcca tgtgcacctg gtcaatcagt tttggatgcg gccttacaag caggtatcga    6120
attgccttat agctgccgta aaggttcatg tgggaattgt gcaagtactc ttttagatgg    6180
taatattgca tctttcaacg gtatggctgt tcgtaatgaa ttatgtgcgt ctgaacaagt    6240
gttattgtgt ggttgcacgg cggcatctga tatacgtatt catccttctt cttttccgtcg   6300 tcttgaccca gaagctcgta acgtttcac tgctaaggta tattcaaata ctcttgctgc    6360
tccagatgta tctcttctcc gtctccgttt acctgttggt aaacgtgcta aatttgaagc    6420
tggtcaatat ttactaatcc acttagatga cggtgagagc cgtagctaca gcatggcaaa    6480
tccaccacat gaatctgatg gtatccacctt acatgttcgt catgttccag gtgggcgttt    6540
tagtactatt gtacaacaat tgaaatcagg agatactttg gacattgaat tacctttggg    6600
ttctattgcg cttaaacctg atgacgctcg tcctctgatc tgtgtagctg gtggtaccgg    6660
ctttgctcca atcaaatccg ttttagacga tctcgcgaaa cgtaaagtac agcgcgatat    6720
cacacttatc tggggcgcac gcaatccatc tggcttatat cttccatcag ctatcgataa    6780
gtggcgtaag gtatggccac aattccgtta catcgccgct atcactgatc ttggggatat    6840
gccagctgat gcacacgctg gtcgtgtgga cgacgcatta cgtactcatt ttggtaatct    6900
gcatgatcat gttgttcatt gttgtggttc gcctgctcta gttcaaagtg tccgtacagc    6960
cgcctcggac atgggtctac tagcgcaaga tttccatgca gatgtatttg caactggtcc    7020
```

-continued

```
tacaggtcac cactagcgga acggcgatgt gaaaattaaa agtcaaaaag attttttttc   7080
tggtttgatg ttccttgcag ttggtttagc atttgcaatt ggtgcttcaa attatactat   7140
tggtactggt gctcgtatgg gtccaggtta tttccctctt atacttggtg tactgatggc   7200
gattctaggt gcagctatct gtgttggtgg tcttactaaa ggtccagagg gtggtgataa   7260
aattggtaaa tgggcatggc gtcaagtttt ttttatcttg gcagcaaatt ttgcattcgg   7320
cattttgtta gtgggtgtac cagcagttgg tattccacaa tttggtctta ttatcgcaat   7380
ttatgcgtta gtcttcatcg cgtctttggg tggccactct ttcaacttca agaaaccgc   7440
gatccttgca acggtgcttg cagttggttc ttacttcgct tttgtttggg cattaaactt   7500
acaattccca gtatggccat catttatcgc gggttaaccg gtaagcggca tggatcttat   7560
tcaaaactta agtaccggct tcggtgtggc tttcactttc caaaatttga tttattgttt   7620
cgttggttgt cttttaggta ctttaattgg cgtacttcca ggcattggtc cagttgctac   7680
aattgcaatg ttattgcctg caacctatgc tttaccacca gtggctgcat tgattatgtt   7740
ggctggtatc tactatggtg cgcagtatgg tggtagtact actgctattt tggtaaatct   7800
tccgggtgaa tcttcttctg tagtcaccgt tatcgatggt taccaaatgg ctcgtaaagg   7860
tcgtgcaggt ccagcgcttg ctgctgctgg tattggttct tttttcgcag ttgtgttgg    7920
tacagtgatc ttagcggctt tcgctccacc tctcacggaa gttgcattca agtttggacc   7980
tgcagagtat ttttcttta tgacattggg tctaattggt gcagttgtcc ttgcttcagg    8040
ctctttgctc aaagcaattg caatgatcgt actcggtctt ttgcttggca tggttggtac   8100
ggacgtaaat tcaggtgtag cgcgttactc atttgacatt ccagagctaa cagatggtat   8160
tgattttgtt gtgatcgcaa tgggtgtttt tggttacggt gaaattattg caaatctttc   8220
aaagcctgat gatgaacgtg aggttttgc agcgaaagtg actggtcttc ttccaacaag    8280
tgaagacttc aaacgtatgt tgccagcaat gttgcgtggt acagcattag gttcagcttt   8340
aggaattttg ccaggtggtg gtgctatgtt gagtgcattt gcagcttata caattgaaaa   8400
aaaaaccaaa ttaaaacctg gtgaagtacc atttggtcag ggcaatattc gtggcgtttg   8460
cgctccggaa tcagcaaaca acgctggtag tcaaacatct ttcattccac tgttaacatt   8520
gggcattcct ccaaacgccg taatggctct catggtaggc gcaatgacta ttcacaacat   8580
tcaaccagga ccacaagtga tgacatctaa ccctgaacta ttttggggtc ttattgcaag   8640
catgtggatt ggtaatttga tgttaattat tttgaaccta ccacttatcg gtgtgtggat   8700
caagttgctt acagtaccat atcgttggtt gtttccatct atcgtattat tttgtgcaat   8760
tggtgtgtat ggtactaata caacgtttg ggatgtttgg atggtaggta ttttttggttt   8820
cattggttat gtattccaca gttagggac tgaacctgct cctttgttgt tgggtttcat   8880
tttaggtcca atgatggaag aaaaccttcg ccgtgctcta ttgctatcgc gtggcgactg   8940
gtctgtattt gttacgcgtc caattagtgc atgcttactg gcagcggctg ttgtgcttct   9000
tgtaatcgtt cttatgcctg cagttaagaa taaacgtgaa gaggcctttg tagaagattg   9060
aactagttct agagcggccg ccaccgcggt ggagctcggt acgatccggt gattgattga   9120
gcaagcttta tgcttgtaaa ccgttttgtg aaaaaatttt taaaataaaa aaggggacct   9180
ctagggtccc caattaatta gtaatataat ctattaaagg tcattcaaaa ggtcatccac   9240
cggatcaatt cccctgctcg cgcaggctgg gtgccaagct ctcgggtaac atcaaggccc   9300
gatccttgga gcccttgccc tcccgcacga tgatcgtgcc gtgatcgaaa tccagatcct   9360
tgacccgcag ttgcaaaccc tcactgatcc gtcgaccaaa gcggccatcg tgcctcccca   9420
```

```
ctcctgcagt tcggggggcat ggatgcgcgg atagccgctg ctggtttcct ggatgccgac   9480
ggatttgcac tgccggtaga actccgcgag gtcgtccagc ctcaggcagc agctgaacca   9540
actcgcgagg ggatcgagcc cggggtgggc gaagaactcc agcatgagat ccccgcgctg   9600
gaggatcatc cagccggcgt cccggaaaac gattccgaag cccaacccttt catagaaggc   9660 ggcggtggaa tcgaaatctc gtgatggcag gttgggcgtc gcttggtcgg tcatttcgaa   9720
ccccagagtc ccgctcagaa gaactcgtca agaaggcgat agaaggcgat gcgctgcgaa   9780
tcgggagcgg cgataccgta aagcacgagg aagcggtcag cccattcgcc gccaagctct   9840
tcagcaatat cacgggtagc caacgctatg tcctgatagc ggtccgccac acccagccgg   9900
ccacagtcga tgaatccaga aaagcggcca ttttccacca tgatattcgg caagcaggca   9960
tcgccatggg tcacgacgag atcctcgccg tcgggcatgc gcgccttgag cctggcgaac  10020
agttcggctg gcgcgagccc ctgatgctct tcgtccagat catcctgatc gacaagaccg  10080
gcttccatcc gagtacgtgc tcgctcgatg cgatgtttcg cttggtggtc gaatgggcag  10140
gtagccggat caagcgtatg cagccgccgc attgcatcag ccatgatgga tactttctcg  10200
gcaggagcaa ggtgagatga caggagatcc tgccccggca cttcgcccaa tagcagccag  10260
tcccttcccg cttcagtgac aacgtcgagc acagctgcgc aaggaacgcc cgtcgtggcc  10320
agccacgata gccgcgctgc ctcgtcctgc agttcattca gggcaccgga caggtcggtc  10380
ttgacaaaaa gaaccgggcg cccctgcgct gacagccgga cacggcggc atcagagcag  10440 ccgattgtct gttgtgccca gtcatagccg aatagcctct ccacccaagc ggccggagaa  10500
cctgcgtgca atccatcttg ttcaatcatg cgaaacgatc ctcatcctgt ctcttgatca  10560
gatcttgatc ccctgcgcca tcagatcctt ggcggcaaga aagccatcca gtttactttg  10620
cagggcttcc caaccttacc agaggggcgcc ccagctggca attccggttc gcttgctgtc  10680
cataaaaccg cccagtctag ctatcgccat gtaagcccac tgcaagctac ctgctttctc  10740
tttgcgcttg cgttttccct tgtccagata gcccagtagc tgacattcat ccggggtcag  10800 caccgttttct gcggactggc tttctacgtg ttccgcttcc tttagcagcc cttgcgccct  10860
gagtgcttgc ggcagcgtga agctcgcgca gatcagttgg aagaatttgt ccactacgtg  10920
aaaggcgaga tcaccaaggt agtcggcaaa taatgtctaa caattcgttc aagccgacgc  10980
cgcttcgcgg cgcggcttaa ctcaagcgtt agatgcacta agcacataat tgctcacagc  11040
caaactatca ggtcaagtct gctttttatta ttttttaagcg tgcataataa gccctacaca  11100
aattgggaga tatatcatga aaggctggct ttttcttgtt atcgcaatag ttggcgaagt  11160
aatcgcaaca tccgcattaa aatctagcga gggctttact aagctgatcc ggtggatgac  11220
cttttgaatg acctttaata gattatatta ctaattaatt ggggacccta gaggtcccct  11280 ttttttatttt aaaaatttt tcacaaaacg gtttacaagc ataaagcttg ctcaatcaat  11340
caccggatct accgggcccc ccctcgaggt cgacggtatc gataagcttg atatcgaatt  11400
cctgcagccc gggggatcca ctagttaaaa caaaaagaga gcgattagtc gctctctttt  11460
ttatctcggc tgtgtttatt tacaagtgaa attctcggct ttttcactgt cacctgtacc  11520
gttataacgt gcgattttg gatatggaca tagtggtcga gttcgattgg ccgaccagct  11580
cgatggtaac tcgctattga tttcgccact tgcattaccg acaccgcgtg cagaagcgag  11640
aatttgatct ggtgcttgac catattctac ccagttcacc aaagcagtaa gtgcatcaaa  11700
ctggtcggtc gcaagcccac cccgcgaatg attcattccc ggaacgcgat aaaaacgagc  11760
```

| | | | | |
|---|---|---|---|---|
| aaaactttgt | gcgtcaccca | aactgctgct | cttgtatttt | gccatcagtt tatcgtacca | 11820 |
| gttttgtgtg | tcatctaccg | aaaatacgcc | atctgctgtg | ccttgcacca caatcatttt | 11880 |
| accgccatgc | aagcgtaatt | tatccagatt | gagctcatct | ggcgggatca taaatgacat | 11940 |
| cgcgctttct | gaataggtcg | aattggttgc | agaaagtttt | gggtaatctg tatcaaaatt | 12000 |
| atagttaaag | gcaaattttc | gtgaattttg | cacaattgtt | ggatctggtg gtacctgaaa | 12060 |
| tataatgcct | accgctaccg | ggtcgcgtgc | cgtacccaca | gaagaaacaa atttccagct | 12120 |
| tgcccaattg | ctgccaagta | atcccggatc | gtaaggctgg | gtcgcataca atgcttcgcc | 12180 |
| agatgaattg | acagggccgc | ggtaaatatt | agccacgaca | tcgatctggt ctttactcaa | 12240 |
| acagcttcca | tcacgtgaac | ccgagcagac | aggcacatct | ttatgaatat caaaggcggt | 12300 |
| tcgacaggct | tcaacgtctt | gtaccatacc | atctgctaca | ccatcgagtg catcacagcg | 12360 |
| tgttaaaatc | gcattggcaa | gtacgttacg | ttctgcatag | gtgagtgcag tgcttaaatc | 12420 |
| attttcatcg | gtggcaacac | gacgtaattg | ctgcgccgtg | tatagctgtg ccgctgctgc | 12480 |
| acgtggtaga | tgaaatccgg | gtgtgcttgc | caagatgcca | tcgtactgat cgcctaggcg | 12540 |
| tgttgcagcc | atcatggcat | gtcgaccgcc | gttagacgta | cctcctgcat aagatcgatc | 12600 |
| tggcaattta | ccgtaagctg | ttttaatcag | atctttggcc | ataggcgtta actttgtaat | 12660 |
| agcaccataa | ccatagttga | tgcgagcttg | cggatctaaa | ccaaaaagag gattttgtgc | 12720 |
| agatgaatgt | ccggcatcgg | atgaaattac | cgcgaatccg | tcttttaaag cattgcttaa | 12780 |
| catcccgccg | ctgcccactt | gtccggtcgc | tgtggcgatg | ttgccgtcgg taccgccatt | 12840 |
| tccttgatat | agaaaacgtc | cgttccagct | caccggaagt | cgcatttcaa agccaatctg | 12900 |
| ataggtttga | ccatcgattg | ggctaatacg | ttgctccata | taacctttga ccaaacaatg | 12960 |
| cgccggaata | tttttcccca | cgacggtcag | agcgcctgca | ttttgtaaag ttgcactttc | 13020 |
| aactacggtg | gtatcaaatt | tgaaaccgct | taaatctgta | caactgcctt tgagctgagc | 13080 |
| acctactgct | gggcttaatt | gtggaatact | ttggctcgac | tgtgccgtat catgatcgtt | 13140 |
| attgtcatta | catgcagcta | cactgatgca | gacgccgagc | aatgcagcat gtttaaaaaa | 13200 |
| atgttgaggt | ttttcattg | caatatcctt | atgcct | | 13236 |

```
<210> SEQ ID NO 16
<211> LENGTH: 78
<212> TYPE: DNA
<213> ORGANISM: Artificial Sequence
<220> FEATURE:
<223> OTHER INFORMATION: Codon optimized to P. putida KT 2440 signal
      sequences

<400> SEQUENCE: 16
atgaacttcc ctcgcgcgtc gcgcctgatg caggcggcgg tcctcggtgg tctgatggca      60
gtcagcgccg cggccacc                                                    78

<210> SEQ ID NO 17
<211> LENGTH: 27
<212> TYPE: PRT
<213> ORGANISM: Artificial Sequence
<220> FEATURE:
<223> OTHER INFORMATION: amino acid sequence of signal peptide

<400> SEQUENCE: 17

Met Asn Phe Pro Arg Ala Ser Arg Leu Met Gln Ala Ala Val Leu Gly
1               5                   10                  15
```

<210> SEQ ID NO 18
<211> LENGTH: 51
<212> TYPE: DNA
<213> ORGANISM: Artificial Sequence
<220> FEATURE:
<223> OTHER INFORMATION: codon-optimized for P. putida KT 2440 signal
      sequence for MHETase

<400> SEQUENCE: 18
atgcagacca ccgtcaccac tatgctgctg gcatcggtcg ccctggccgc c          51

<210> SEQ ID NO 19
<211> LENGTH: 17
<212> TYPE: PRT
<213> ORGANISM: Artificial Sequence
<220> FEATURE:
<223> OTHER INFORMATION: amino acid sequence of signal peptide for
      MHETase

<400> SEQUENCE: 19

Met Gln Thr Thr Val Thr Thr Met Leu Leu Ala Ser Val Ala Leu Ala
1               5                   10                  15

Ala

<210> SEQ ID NO 20
<211> LENGTH: 48
<212> TYPE: DNA
<213> ORGANISM: Artificial Sequence
<220> FEATURE:
<223> OTHER INFORMATION: Primer LJ227

<400> SEQUENCE: 20
gacatgatta cgaattcgag ctcggtaccc gtgcgattac tgtgggag               48

<210> SEQ ID NO 21
<211> LENGTH: 34
<212> TYPE: DNA
<213> ORGANISM: Artificial Sequence
<220> FEATURE:
<223> OTHER INFORMATION: Primer LJ232

<400> SEQUENCE: 21
ccggaggctt ttgactcgga ggcgcggcgc aggc                             34

<210> SEQ ID NO 22
<211> LENGTH: 36
<212> TYPE: DNA
<213> ORGANISM: Artificial Sequence
<220> FEATURE:
<223> OTHER INFORMATION: Primer LJ228

<400> SEQUENCE: 22
cggataacaa tttcacactg agtattgcct gaaccg                           36

<210> SEQ ID NO 23
<211> LENGTH: 112
<212> TYPE: DNA
<213> ORGANISM: Artificial Sequence
<220> FEATURE:
<223> OTHER INFORMATION: Primer LJ229

<400> SEQUENCE: 23
ttcaggcaat actcagtgtg aaattgttat ccgctcacaa ttccacacat tatacgagcc    60
gatgattaat tgtcaacagc tcttcatcaa gtcaaaacac tatataggaa cg    112

<210> SEQ ID NO 24
<211> LENGTH: 36
<212> TYPE: DNA
<213> ORGANISM: Artificial Sequence
<220> FEATURE:
<223> OTHER INFORMATION: Primer LJ230

<400> SEQUENCE: 24
atgtaatcct tgttataggc tgcagttcgc agtgcg    36

<210> SEQ ID NO 25
<211> LENGTH: 66
<212> TYPE: DNA
<213> ORGANISM: Artificial Sequence
<220> FEATURE:
<223> OTHER INFORMATION: Primer LJ231

<400> SEQUENCE: 25
actgcgaact gcagcctata acaaggatta catataaggg tatatcaaat gcagaccacc    60
gtcacc    66

<210> SEQ ID NO 26
<211> LENGTH: 70
<212> TYPE: DNA
<213> ORGANISM: Artificial Sequence
<220> FEATURE:
<223> OTHER INFORMATION: Primer LJ233

<400> SEQUENCE: 26
tgcgccgcgc ctccgagtca aaagcctccg gtcggaggct tttgacttca aaaccaccct    60
gctgtcgatg    70

<210> SEQ ID NO 27
<211> LENGTH: 50
<212> TYPE: DNA
<213> ORGANISM: Artificial Sequence
<220> FEATURE:
<223> OTHER INFORMATION: Primer LJ234

<400> SEQUENCE: 27
cggccagtgc caagcttgca tgcctgcagg aaatctaact gccttcgccc    50

<210> SEQ ID NO 28
<211> LENGTH: 74
<212> TYPE: DNA
<213> ORGANISM: Artificial Sequence
<220> FEATURE:
<223> OTHER INFORMATION: Primer LJ406

<400> SEQUENCE: 28
tatgttgtgt ggaattgtga gcggataaca atttcacact ttcatcaagt caaaacacta    60
tataggaacg aaac    74

<210> SEQ ID NO 29
<211> LENGTH: 47
<212> TYPE: DNA
<213> ORGANISM: Artificial Sequence
<220> FEATURE:

<223> OTHER INFORMATION: Primer LJ407

<400> SEQUENCE: 29
tccgcactgc gaactgcagc ggtggttctg aggaatctta catgagc          47

<210> SEQ ID NO 30
<211> LENGTH: 39
<212> TYPE: DNA
<213> ORGANISM: Artificial Sequence
<220> FEATURE:
<223> OTHER INFORMATION: Primer LJ408

<400> SEQUENCE: 30
gtaagattcc tcagaaccac cgctgcagtt cgcagtgcg                   39

<210> SEQ ID NO 31
<211> LENGTH: 58
<212> TYPE: DNA
<213> ORGANISM: Artificial Sequence
<220> FEATURE:
<223> OTHER INFORMATION: Primer LJ409

<400> SEQUENCE: 31
agtccagtta cgctggagtc tgaggctcgt cctgaatgat ctacttgtag agttcgtc    58

<210> SEQ ID NO 32
<211> LENGTH: 34
<212> TYPE: DNA
<213> ORGANISM: Artificial Sequence
<220> FEATURE:
<223> OTHER INFORMATION: nt sequence of sRBS for PETase

<400> SEQUENCE: 32
tcatcaagtc aaaacactat ataggaacga aacc                        34

<210> SEQ ID NO 33
<211> LENGTH: 30
<212> TYPE: DNA
<213> ORGANISM: Artificial Sequence
<220> FEATURE:
<223> OTHER INFORMATION: nt sequence of sRBS for MHETase

<400> SEQUENCE: 33
taacaaggat tacatataag ggtatatcaa                             30

<210> SEQ ID NO 34
<211> LENGTH: 18
<212> TYPE: DNA
<213> ORGANISM: Artificial Sequence
<220> FEATURE:
<223> OTHER INFORMATION: Primer CJ366

<400> SEQUENCE: 34
cgattgcgcc atgaacag                                          18

<210> SEQ ID NO 35
<211> LENGTH: 18
<212> TYPE: DNA
<213> ORGANISM: Artificial Sequence
<220> FEATURE:
<223> OTHER INFORMATION: Primer CJ367

<400> SEQUENCE: 35
aggctgccga gtatcatg                                          18

```
<210> SEQ ID NO 36
<211> LENGTH: 30
<212> TYPE: DNA
<213> ORGANISM: Artificial Sequence
<220> FEATURE:
<223> OTHER INFORMATION: Primer CJ911

<400> SEQUENCE: 36
ttgaattcga gctgttgaca attaatcatc                                          30

<210> SEQ ID NO 37
<211> LENGTH: 19
<212> TYPE: DNA
<213> ORGANISM: Artificial Sequence
<220> FEATURE:
<223> OTHER INFORMATION: Primer CJ912

<400> SEQUENCE: 37
gacctcgagg atacggttg                                                      19

<210> SEQ ID NO 38
<211> LENGTH: 60
<212> TYPE: DNA
<213> ORGANISM: Artificial Sequence
<220> FEATURE:
<223> OTHER INFORMATION: Primer LJ426

<400> SEQUENCE: 38
aaacagctat gacatgatta cgaattcgag ctcggtaccc cgtggtgctg gactacaagg         60

<210> SEQ ID NO 39
<211> LENGTH: 39
<212> TYPE: DNA
<213> ORGANISM: Artificial Sequence
<220> FEATURE:
<223> OTHER INFORMATION: Primer LJ427

<400> SEQUENCE: 39
tcttcgtgcc tcgagagccc tcgtttgcct gcgtgatcg                                39

<210> SEQ ID NO 40
<211> LENGTH: 36
<212> TYPE: DNA
<213> ORGANISM: Artificial Sequence
<220> FEATURE:
<223> OTHER INFORMATION: Primer LJ428

<400> SEQUENCE: 40
tcgatcacgc aggcaaacga gggctctcga ggcacg                                   36

<210> SEQ ID NO 41
<211> LENGTH: 58
<212> TYPE: DNA
<213> ORGANISM: Artificial Sequence
<220> FEATURE:
<223> OTHER INFORMATION: Primer LJ429

<400> SEQUENCE: 41
tgtaaaacga cggccagtgc caagcttgca tgcctgcagg cggcatcgac atcacccc          58

<210> SEQ ID NO 42
<211> LENGTH: 18
<212> TYPE: DNA
<213> ORGANISM: Artificial Sequence
<220> FEATURE:
<223> OTHER INFORMATION: Primer LJ430
```

```
<400> SEQUENCE: 42
ccttctgccc cacctcca                                                    18

<210> SEQ ID NO 43
<211> LENGTH: 15
<212> TYPE: DNA
<213> ORGANISM: Artificial Sequence
<220> FEATURE:
<223> OTHER INFORMATION: Primer LJ431

<400> SEQUENCE: 43
cccccgcagc actct                                                       15

<210> SEQ ID NO 44
<211> LENGTH: 18
<212> TYPE: DNA
<213> ORGANISM: Artificial Sequence
<220> FEATURE:
<223> OTHER INFORMATION: Primer CJ546

<400> SEQUENCE: 44
atagtcctgt cgggtttc                                                    18

<210> SEQ ID NO 45
<211> LENGTH: 20
<212> TYPE: DNA
<213> ORGANISM: Artificial Sequence
<220> FEATURE:
<223> OTHER INFORMATION: Primer CJ547

<400> SEQUENCE: 45
ccatcttgtt caatcatgcg                                                  20

<210> SEQ ID NO 46
<211> LENGTH: 100
<212> TYPE: DNA
<213> ORGANISM: Artificial Sequence
<220> FEATURE:
<223> OTHER INFORMATION: Primer CJ915

<400> SEQUENCE: 46
aattaatcat cggctcgtat aatgtgtgga attgtgagcg gataacaatt tcacaccgga      60
gggagttttg cgatgaatat cctgtacgac gaacgcgtcg                           100

<210> SEQ ID NO 47
<211> LENGTH: 67
<212> TYPE: DNA
<213> ORGANISM: Artificial Sequence
<220> FEATURE:
<223> OTHER INFORMATION: Primer CJ916

<400> SEQUENCE: 47
ccacacatta tacgagccga tgattaattg tcaacagctc gaattcaaaa aaccgcacct      60
gggtgcg                                                                67

<210> SEQ ID NO 48
<211> LENGTH: 75
<212> TYPE: DNA
<213> ORGANISM: Artificial Sequence
<220> FEATURE:
<223> OTHER INFORMATION: Primer LJ189
```

<400> SEQUENCE: 48
ggaattgtga gcggataaca atttcacact tcatcaagtc aaaacactat ataggaacga      60
aaccatgaac ttccc                                                      75

<210> SEQ ID NO 49
<211> LENGTH: 48
<212> TYPE: DNA
<213> ORGANISM: Artificial Sequence
<220> FEATURE:
<223> OTHER INFORMATION: Primer LJ190

<400> SEQUENCE: 49
cgctggagtc tgaggctcgt cctgaatgat cggaggcgcg gcgcaggc                   48

<210> SEQ ID NO 50
<211> LENGTH: 24
<212> TYPE: DNA
<213> ORGANISM: Artificial Sequence
<220> FEATURE:
<223> OTHER INFORMATION: Primer CJ906

<400> SEQUENCE: 50
cttcgccaac aacaacaaaa accg                                             24

<210> SEQ ID NO 51
<211> LENGTH: 18
<212> TYPE: DNA
<213> ORGANISM: Artificial Sequence
<220> FEATURE:
<223> OTHER INFORMATION: Primer CJ907

<400> SEQUENCE: 51
cctgcgggtt gacctcga                                                    18

<210> SEQ ID NO 52
<211> LENGTH: 16
<212> TYPE: DNA
<213> ORGANISM: Artificial Sequence
<220> FEATURE:
<223> OTHER INFORMATION: Primer CJ913

<400> SEQUENCE: 52
gtagcacccg cctgcc                                                      16

<210> SEQ ID NO 53
<211> LENGTH: 19
<212> TYPE: DNA
<213> ORGANISM: Artificial Sequence
<220> FEATURE:
<223> OTHER INFORMATION: Primer CJ912

<400> SEQUENCE: 53
gacctcgagg atacggttg                                                   19

<210> SEQ ID NO 54
<211> LENGTH: 53
<212> TYPE: DNA
<213> ORGANISM: Artificial Sequence
<220> FEATURE:
<223> OTHER INFORMATION: Primer CJ929

<400> SEQUENCE: 54
gcttgacaat taatcatcgg ctcgtataat gtgtggaatt gtgagcggat aac             53

<210> SEQ ID NO 55
<211> LENGTH: 51
<212> TYPE: DNA
<213> ORGANISM: Artificial Sequence
<220> FEATURE:
<223> OTHER INFORMATION: Primer CJ930

<400> SEQUENCE: 55
ttatacgagc cgatgattaa ttgtcaagcc tggggtgcct aatgcaaaat c            51

<210> SEQ ID NO 56
<211> LENGTH: 21
<212> TYPE: DNA
<213> ORGANISM: Artificial Sequence
<220> FEATURE:
<223> OTHER INFORMATION: Primer CJ054

<400> SEQUENCE: 56
atcggctcgt ataatgtgtg g                                             21

<210> SEQ ID NO 57
<211> LENGTH: 19
<212> TYPE: DNA
<213> ORGANISM: Artificial Sequence
<220> FEATURE:
<223> OTHER INFORMATION: Primer LJ484

<400> SEQUENCE: 57
ggccccacca cttgatcga                                                19

<210> SEQ ID NO 58
<211> LENGTH: 42
<212> TYPE: DNA
<213> ORGANISM: Artificial Sequence
<220> FEATURE:
<223> OTHER INFORMATION: Primer CJ935

<400> SEQUENCE: 58
cccctcgatc acgcaggcaa acgaagtcaa aagcctccgg tc                      42

<210> SEQ ID NO 59
<211> LENGTH: 40
<212> TYPE: DNA
<213> ORGANISM: Artificial Sequence
<220> FEATURE:
<223> OTHER INFORMATION: Primer CJ936

<400> SEQUENCE: 59
cttcgtgcct cgagagccca aaactaaagc gccacaaggg                         40

<210> SEQ ID NO 60
<211> LENGTH: 18
<212> TYPE: DNA
<213> ORGANISM: Artificial Sequence
<220> FEATURE:
<223> OTHER INFORMATION: Primer CJ920

<400> SEQUENCE: 60
gcaaagtgga caccgctc                                                 18

<210> SEQ ID NO 61
<211> LENGTH: 20
<212> TYPE: DNA
<213> ORGANISM: Artificial Sequence
<220> FEATURE:
<223> OTHER INFORMATION: Primer CJ921

```
<400> SEQUENCE: 61
gtagttgaag tggccgcatg                                                20

<210> SEQ ID NO 62
<211> LENGTH: 20
<212> TYPE: DNA
<213> ORGANISM: Artificial Sequence
<220> FEATURE:
<223> OTHER INFORMATION: Primer CJ922

<400> SEQUENCE: 62
catcctcggt acttgcgatg                                                20

<210> SEQ ID NO 63
<211> LENGTH: 19
<212> TYPE: DNA
<213> ORGANISM: Artificial Sequence
<220> FEATURE:
<223> OTHER INFORMATION: Primer CJ947

<400> SEQUENCE: 63
gttcctcgtc ccaggcatg                                                 19

<210> SEQ ID NO 64
<211> LENGTH: 20
<212> TYPE: DNA
<213> ORGANISM: Artificial Sequence
<220> FEATURE:
<223> OTHER INFORMATION: Primer CJ948

<400> SEQUENCE: 64 gccectacgc tggatcttgc                                                20

<210> SEQ ID NO 65
<211> LENGTH: 17
<212> TYPE: DNA
<213> ORGANISM: Artificial Sequence
<220> FEATURE:
<223> OTHER INFORMATION: Primer CJ928

<400> SEQUENCE: 65
gaaggcgaag gcgacac                                                   17

<210> SEQ ID NO 66
<211> LENGTH: 2810
<212> TYPE: DNA
<213> ORGANISM: Artificial Sequence
<220> FEATURE:
<223> OTHER INFORMATION: nt sequence for expressed codon optimized
      PETase and MHETase from Ideonella sakaiensis

<400> SEQUENCE: 66
gagctgttga caattaatca tcggctcgta taatgtgtgg aattgtgagc ggataacaat    60
ttcacactca tcaagtcaaa acactatata ggaacgaaac catgaacttc cctcgcgcgt   120
cgcgcctgat gcaggcggcg gtcctcggtg gtctgatggc agtcagcgcc gcggccaccg   180
ctcagaccaa cccatacgcc cgcggcccaa accctaccgc ggccagcctg aagcctctg    240 ccggcccatt caccgtgcgc agcttcaccg tcagtcgccc gtcgggctat ggtgccggca   300
ccgtctacta cccaaccaac gctggcggca ccgtcggcgc catcgcaatc gtgccgggct   360
ataccgcccg ccagtcctcg atcaagtggt ggggcccacg tctggcctcc cacggcttcg   420
ttgttatcac catcgacacc aactcgaccc tggaccagcc gtcctcccgc tcgagccagc   480
```

```
agatggctgc tctgcgccag gtagcttcgc tgaacggcac cagctctagc ccaatctacg    540
gcaaagtgga caccgctcgc atgggcgtga tgggttggtc catgggcggt ggtggttccc    600
tgatctccgc tgctaataat ccttccctga aggccgccgc cccgcaggcc ccatgggact    660
cctcgaccaa cttctcgagc gtgaccgtgc cgaccctgat cttcgcttgc gaaaacgaca    720
gcatcgctcc ggtgaactcc tccgcgctgc ctatctacga ctccatgagc cgcaacgcca    780
agcaattcct ggaaatcaac ggcggttccc actcctgcgc taactcgggc aactcgaacc    840
aagccctgat cggcaagaag ggcgtagcat ggatgaagcg tttcatggat aacgacaccc    900
gttactcgac cttcgcctgc gaaaacccga actctactcg cgtcagcgac ttccgcactg    960
cgaactgcag ctaacaagga ttacatataa gggtatatca aatgcagacc accgtcacca   1020
ctatgctgct ggcatcggtc gccctggccg cctgcgcagg cggcggcagc accccgctgc   1080
cgctgccgca gcaacagccg ccacagcagg agccgccgcc tcctccagtc ccgctggctt   1140
cccgtgctgc gtgtgaggcc ctgaaggacg gcaacgggga catggtttgg ccgaacgccg   1200
ccaccgtagt tgaagtggcc catggcgcg acgctgcccc ggctaccgcg tccgccgccg   1260
ctctgccgga acactgcgaa gttagcgcg ccatcgccaa gcgcactggt attgacggtt   1320
atccgtacga aatcaagttc cgcctgcgca tgccggcgga gtggaatggc cgtttcttca   1380
tggagggtgg ttccggcacc aacggctccc tgagcgcggc caccggcagc atcggtggcg   1440
gccagatcgc ctcggccctg tcccgcaact tcgccaccat cgcgaccgac ggtggccacg   1500
acaacgctgt caacgacaat ccagacgccc tgggtacggt agcgttcggc ctggacccac   1560
aggctcgcct ggacatgggt tacaattcgt acgaccaggt gacccaagct ggcaaagccg   1620
ccgttgcccg tttctacggc cgtgccgccg acaagtcgta cttcatcggc tgctcggaag   1680
gtggtcggga gggcatgatg ctcagccaac gcttcccatc ccactacgac ggtatcgtcg   1740
ccggtgcccc tggctaccag ctgcctaaag ccggtatctc gggcgcttgg accactcagt   1800
cgctggcccc ggcggcggtg ggcctggacg ctcagggcgt cccgctgatc aacaagagct   1860
tctccgatgc cgacctgcac ctgctgtcgc aggccatcct cggtacttgc gatgcgctgg   1920
acggcctggc tgacggcatc gttgacaact accgcgcgtg ccaggccgct ttcgacccgg   1980
ctaccgcggc taaccctgcc aacggtcaag ctctgcaatg tgtgggtgcc aaaaccgccg   2040
attgcctgag cccggtacag gttaccgcca tcaaacgtgc aatggccggc ccggtcaaca   2100
gcgccggcac cccgctgtac aaccgttggg cctgggacgc tggtatgagc ggcctgtccg   2160
gtaccaccta caatcagggc tggcgttcct ggtggctggg tagcttcaac tcctcggcga   2220
acaacgcgca gcgtgtttcg ggtttctccg cccgctcctg gctggtcgac ttcgccaccc   2280
caccagagcc tatgccgatg acccaggtgg ctgcacgcat gatgaaattc gacttcgaca   2340
tcgacccgct gaagatctgg gccaccagcg gccagttcac ccagtcgagc atggactggc   2400
acggggccac ctccaccgac ctggccgcct tccgcgatcg tggcggcaag atgatcctgt   2460
accacggtat gagcgacgca gccttctcgg ccctggacac cgctgactac tacgaacgcc   2520
tgggcgccgc tatgccgggc gccgcgggct tcgctcgtct gttcctcgtc ccaggcatga   2580
accactgttc gggcggtcca ggtaccgacc gtttcgacat gctgacccct ctggtggcgt   2640
gggttgagcg cggcgaagcc ccggaccaga tctcggcgtg gagcggcacc ccaggctact   2700
tcggcgtcgc tgcccgtacc cgcccgctgt gcccgtaccc gcaaatcgca cgctacaagg   2760
gttccggcga tatcaacacc gaagcaaact tcgcctgcgc cgcgcctccg            2810
```

ENGINEERED MICROORGANISMS FOR THE DECONSTRUCTION OF POLYMERS

CROSS-REFERENCE TO RELATED APPLICATIONS

This application is a continuation in part of and claims priority under 35 U.S.C. § 119 to U.S. patent application Ser. No. 17/055,626 filed on 16 Nov. 2020 which is a national stage 371 application of PCT/US19/32480 filed on 15 May 2019, which claims priority under 35 U.S.C. § 119 to U.S. Provisional Patent Application No. 62/671,477 filed on 15 May 2018, the contents of which are hereby incorporated in their entirety.

CONTRACTUAL ORIGIN

The United States Government has rights in this disclosure under Contract No. DE-AC36-08GO28308 between the United States Department of Energy and Alliance for Sustainable Energy, LLC, the Manager and Operator of the National Renewable Energy Laboratory. The United States Government has rights in this invention pursuant to contract no. DE-AC05-00OR22725 between the United States Department of Energy and UT-Battelle, LLC.

SEQUENCE LISTING

The instant application contains a Sequence Listing which has been submitted via EFS-web and is hereby incorporated by reference in its entirety. The ASCII copy as filed herewith was originally created on 6 Oct. 2023. The ASCII copy as filed herewith is named NREL 18-76A_ST25.txt, is 83 kilobytes in size and is submitted with the instant application.

BACKGROUND

Poly (ethylene terephthalate) (PET) is one of the most abundant manmade synthetic polyesters. Crystalline PET is being widely used for production of single-use beverage bottles, clothing, packaging, and carpeting materials. PET resistance to biodegradation due to limited accessibility to ester linkage, and disposal of PET products into the environment pose a serious threat to biosphere, particularly to marine environment. PET can be chemically recycled; however, the extra costs in chemical recycling are not justified when converting PET back to PET. Thus, there remains a need for alternative strategies for recycling/recovering/reusing PET.

SUMMARY

In an aspect disclosed herein is a genetically modified organism comprising an exogenous gene addition, wherein the exogenous gene addition encodes functional enzymes comprising a PETase and a MHETase, and the genetically modified organism is capable of metabolizing poly (ethylene terephthalate) (PET) to produce PET deconstruction products. In an embodiment, the genetically modified organism has an exogenous gene is from *Ideonella sakaiensis*. In another embodiment, the genetically modified organism has an exogenous gene is codon optimized. In another embodiment, the genetically modified organism has an exogenous gene is incorporated into the genome of the genetically modified organism. In another embodiment, the genetically modified organism has an exogenous gene addition further comprises genes encoding a secretion signal peptide. In another embodiment, the genetically modified organism has a genetically modified organism is a species of *Pseudomonas*. In another embodiment, the genetically modified organism is the species is *Pseudomonas putida*. In another embodiment, the genetically modified organism has PET deconstruction products comprise at least one of bis(2-Hydroxyethyl) terephthalate, mono-(2-hydroxyethyl) terephthalate, terephthalate, ethylene glycol, ß-ketoadipate, or muconate. In another embodiment, the method comprising contacting poly (ethylene terephthalate) (PET) with the genetically modified organisms of claim 1 to produce PET deconstruction products. In another embodiment, the contacting is performed in minimal salt medium. In another embodiment, a genetically modified organism comprising an exogenous gene addition, wherein the exogenous gene addition encodes functional enzymes comprising a PETase and a MHETase, and the genetically modified organism is capable of metabolizing poly (ethylene terephthalate) (PET) to produce PET deconstruction products; and wherein said genetically modified organism further comprises heterologous TPA transporters. In another embodiment, the genetically modified organism further comprising catabolic gene clusters I or II. In another embodiment, the genetically modified organism wherein the catabolic gene clusters I or II are from *Comamonas* sp. E6. In another embodiment, the genetically modified organism is capable of using TPA as a sole carbon source. In another embodiment, the genetically modified organism is capable of metabolizing TPA at about $0.05$ g $L^{-1}$ $h^{-1}$. In another embodiment, the genetically modified organism is lacking a pcaIJ gene. In another embodiment, the genetically modified organism is capable of metabolizing TPA to ß-ketoadipate. In another embodiment, the genetically modified organism is a species of *Pseudomonas*. In another embodiment, the genetically modified organism the exogenous gene is from *Ideonella sakaiensis*. In another embodiment, the genetically modified organism has a PET deconstruction products that comprise at least one of bis(2-Hydroxyethyl) terephthalate, mono-(2-hydroxyethyl) terephthalate, terephthalate, ethylene glycol, ß-ketoadipate, or muconate.

BRIEF DESCRIPTION OF THE DRAWINGS

FIG. 1A illustrates bright field microscopic observation of the strain expressing PETase with GFP tag; FIG. 1B illustrates microscopic observation of GFP signal of the strain expressing PETase with GFP tag; FIG. 1C illustrates GFP signal of the supernatant of wild-type strain and the strain expressing GFP tagged PETase; FIG. 1D illustrates immunoprecipitation of GFP tagged PETase with GFP specific GFP-Trap® (ChromoTek GmbH, Planegg-Martinsried, Germany); and FIG. 1E illustrates a microscopic image of PET particle incubated with the strain expressing GFP tagged PETase.

FIG. 5A depicts curves of the strain (FIG. 5B) growth rate of the strains (FIG. 5C) TPA utilization of the strains. Growth of the strains was assessed in minimal medium containing either 10 mM TPA or 10 mM PCA as the sole substrate for growth, and TPA utilization was measured during growth in minimal medium with 10 mM TPA as the sole growth substrate. Concentrations of TPA were measured using high performance liquid chromatography (HPLC) by injecting culture supernatant onto a Rezex RFQ-Fast Acid H+ (8%) HPLC column. Mobile phase consisted of 5 mM $H_2SO_4$, and samples were run at 0.6 ml/min at 60° C. TPA eluted at ~21 minutes and was detected at a wavelength of 230 nm via a UV-Vis detector. Area under the elution peak was integrated and TPA concentration was calculated against a standard.

FIG. 6A depicts codon optimized sequences of PETase (SEQ ID NO: 1) and FIG. 6B depicts codon optimized sequences of MHETase (SEQ ID NO: 2) genes from *Ideonella sakaiensis* 201-F6 to *P. putida* KT2440.

FIG. 8 depicts the nucleotide sequence of plasmid pLJ080 (SEQ ID NO: 3).

FIG. 9A depicts the amino acid sequence of PETase (SEQ ID NO: 4) and FIG. 9B depicts the amino acid sequence of MHETase (SEQ ID NO: 5).

FIG. 11 depicts the plasmid sequence (SEQ ID NO: 6) of PETase with GFP tag (pLJ081).

FIG. 12 depicts (SEQ ID NO: 7) the nucleotide sequence of synthetic $tphC_{II}$ gene.

FIG. 13 depicts (SEQ ID NO: 8) the nucleotide sequence of synthetic $tphA2_{II}$ gene.

FIG. 14 depicts (SEQ ID NO: 9) the nucleotide sequence of synthetic $tphA3_{II}$ gene.

FIG. 15 depicts (SEQ ID NO: 10) the nucleotide sequence of synthetic $tphB_{II}$ gene.

FIG. 16 depicts (SEQ ID NO: 11) the nucleotide sequence of synthetic $tphA1_{II}$ gene.

FIG. 17 depicts (SEQ ID NO: 12) the nucleotide sequence of synthetic tpiB gene.

FIG. 18 depicts (SEQ ID NO: 13) the nucleotide sequence of synthetic tpiA gene.

FIG. 19 depicts (SEQ ID NO: 14) the nucleotide sequence of the local chromosomal sequence in strain IP103. Homology arms sequences are shown in italic. Synthetic ribosome binding sites are shown in bold. Coding sequences for tph genes are underlined.

FIG. 20 depicts (SEQ ID NO: 15) the nucleotide sequence of the local chromosomal sequence in strain IP131. Homology arms sequences are shown in italic. Synthetic ribosome binding sites are shown in bold. Coding sequences for tph, tpi and kanamycin selection marker genes are underlined.

(FIG. 23a) Conceptual overview of PET plastic upcycling to performance-advantaged nylon: chemocatalytic glycolysis to deconstruct PET to BHET, bioconversion of BHET to βKA, and processing of βKA to performance-advantaged nylon. The bioconversion process (highlighted in pink) is enabled in this body of work. (FIG. 23b) Chemocatalytic glycolysis with a titanium butoxide catalyst and ethylene glycol as the solvent depolymerizes PET into BHET. (FIG. 23c) A metabolic pathway for the conversion of BHET to βKA is engineered in *P. putida*. Enzymes displayed in pink are overexpressed; subscript indicates heterologous expression (Is, *Ideonella sakiensis*; RHA1, *Rhodococcus jostii* RHA1; E6, Comamomas E6); Δ symbols indicate a gene deletion. (FIG. 23d) Acidification and organic solvent extraction efficiently separates βKA (98%, 99+% purity) from culture broth. Steiglich esteriviation to dimethyl βKA enables polymerization with hexamethylenediamine to produce a performance-advantaged nylon. Abbreviations: MHET, mono(2-hydroxyethyl) terephthalic acid; TPA, terephthalic acid; DCD, 1,2-dihydroxy-3,5-cyclohexadiene-1,4-dicarboxylate; PCA, protocatechuic acid; EG, ethylene glycol PETase, PET hydrolase; MHETase, MHET hydrolase; TpaK, probable TPA transporter, MFS superfamily protein; TphA, TPA 1,2-dioxygenase; TphB, DCD dehydrogenase; PcaHG, PCA 3,4-dioxygenase; PcaB, 3-carboxy-cis,cis-muconate cycloisomerase; PcaC, 4-carboxymuconolactone decarboxylase; PcaD, 3-oxoadipate enol-lactonase; PcaIJ, 3-oxoadipate CoA-transferase; GlcDEF, glycolate oxidase; Gcl, glyoxylate carboligase; GclR, GclR transcriptional regulator.

(FIG. 24a) Schematic of beneficial engineering modifications for EG catabolism. (FIG. 24b) Growth of RC0002, MFL185, and RC024 in M9 minimal medium plus 100 mM EG as the sole carbon source. Growth was measured in a Tecan Infinite® F500 at 30° C. (FIG. 24c) Growth and EG concentrations of RC024 shaken flask cultivations in M9 minimal medium supplemented with 100 mM EG as the sole carbon source. Error bars represent the standard deviation among biological triplicates.

(FIG. 25a) Schematic of beneficial engineering modifications for TPA catabolism. (FIG. 25b) Growth rates in x mM PCA and x mM TPA for the four strain which grew in TPA (TDM083, TDM084, TDM086, and TDM087) and growth rate in x mM TPA for 1-2 evolved isolates from each strain. Growth was measured; n=3-4, average±standard deviation is plotted. (FIG. 25c) Growth of serially passaged cultures of TDM087, provided as an illustrative example for the gradual growth improvements observed in TDM083, TDM084, TDM086, and TDM087 lineages. See FIG. S4 for growth profiles and rates across the ALE for all evolved lineages. (FIG. 25d) Growth of wild-type P. putida KT2440, TDM461, Comamonas sp. E6, R. jostii RHA1, and IP250 in 10 mM TPA. Growth was measured in a BioscreenC; n=3, average±standard deviation is plotted. (FIG. 25e) Growth and TPA utilization of strain TDM461 in 45 mM TPA. Cultivations were performed in shaken flasks; n=2, average±absolute difference is plotted.

(FIG. 26a) Schematic of additional engineering modifications for BHET catabolism. PETase and MHETase expression cassette was engineered into RC026 (containing EG and TPA engineering) to generate RC038. (FIG. 26b) Growth RC026 and RC038 cultivated in a BioscreenC® in M9 minimal medium supplemented with 10 mM BHET as the sole carbon source. Growth and analyte concentrations of RC038 cultivated in shaken flasks with M9 minimal medium supplemented with (FIG. 26c) ~10 mM BHET as the sole carbon source or (FIG. 26d) ~10 mM BHET plus 20 mM glucose and fed to 20 mM glucose every 24 h. Error bars represent the standard deviation among biological triplicates.

(FIG. 27a) Schematic of the cumulative P. putida engineering modifications which enabled bKA production from BHET. (FIG. 27b) Solid BHET powder was fed via a headplate port (amounts and times indicated by instantaneous BHET feed "X"s) to a final concentration of 31.5 g/L. (FIG. 27c) Cell growth (measured as $OD_{600}$) and measured concentrations of BHET, metabolic intermediates (MHET and TPA), and beta-ketoadipate (BKA) in bioreactor cultiations of AW165 in M9 minimal medium. Glucose was provided as a DO-stat in 2 mM pulses. The grey arrow indicates where one of the three reactors went offline. Error bars represent the standard deviation among three replicates before the grey arrow and absolute difference after the grey arrow. (FIG. 27d) bKA titer, yield, and productivity every ~24 h. Errors are reported as indicated for (FIG. 27b).

(FIG. 31a) Growth curves for starting strains and end-point isolates (indicated by "e1" or "e2"). (FIG. 31b) Calculated growth rates for the eight starting strains and evolved lineages.

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

In an embodiment, disclosed herein is an engineered *P. putida* KT2440 co-expressing PETase and MHETase enzymes that selectively degrades PET into monomers, ethylene glycol and terephthalate (TPA). In another embodiment, disclosed herein are methods for making and using a highly efficient EG metabolizing *P. putida* KT2440 strain. Given that native *P. putida* does not have a TPA metabolic pathway, nor the proteins to transport TPA into the cell, the next metabolic engineering challenge for developing synthetic *P. putida* strain to plastic upcycling was enabling TPA catabolism in *P. putida* KT2440. TPA transporters and catabolic pathway have been characterized in several microorganisms including *Comamonas* sp. strain E6 and *Rhodococcus jostii* RHA1.

Figure 4:
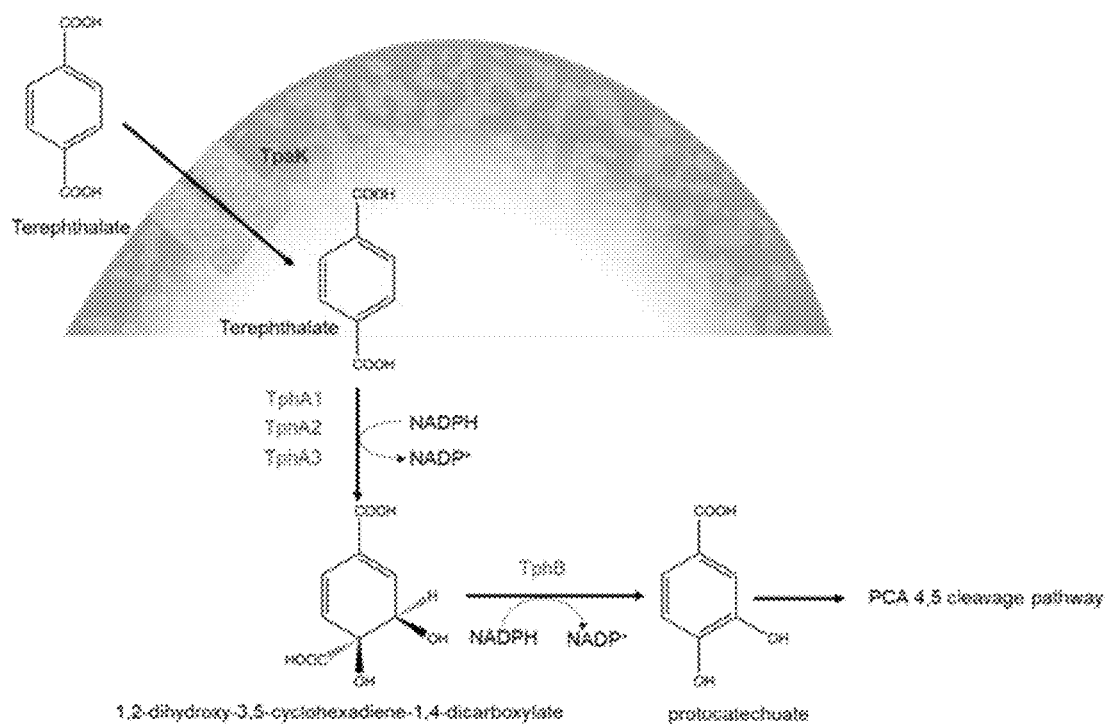
FIG. 4 depicts Engineered TPA catabolic pathway in *P. putida* KT2440, transporter TpaK and catabolic genes (TphA1, TphA2, TphA3, and TphB) are originally from *R. jostii* RHA1 and *Comamonas* sp. strain E6, respectively.

In an embodiment, disclosed herein are engineered *P. putida* KT2440 strains that use TPA through heterologous expression of a TPA transporter from *Rhodococcus jostii* RHA1 and catabolic genes from *Comamonas* sp. E6 (FIG. 4). In an embodiment, the pcaIJ gene was knocked out in the engineered strains, enabling the biological conversion of TPA to ß-ketoadipate. Ultimately, the engineered strains disclosed herein enable the upcycling of PET-derived TPA into atom-efficient ß-ketoadipic acid, a high-value chemical that can be used to produce a biodegradable plastic material with superior properties.

As disclosed herein, in an embodiment, TPA catabolism is enabled in *P. putida* KT2440 by heterologous expression of TPA transporters (tpaK) and catabolic genes cluster I or II from *R. jostii* RHAI and *Comamonas* sp. E6, respectively. The engineered, non-naturally occurring strains can use TPA as a sole carbon source and use TPA at about 0.05 g L$^{-1}$ h$^{-1}$. In an embodiment, the pcaIJ gene was knocked out in an engineered TPA utilizing strain. The strain could convert TPA to ß-ketoadipate. In another embodiment, TPA utilization strain can be engineered for consolidated bioprocessing of PET by enabling selective degradation of PET and ethylene glycol utilization. In an embodiment, strains could be evolved to enhance TPA catabolic rates.

The present disclosure also relates to a biological strategy for degrading PET, which can subsequently enable atom-efficient biological transformations to novel intermediates (e.g., ß-ketoadipate and/or muconate), which may be converted to high strength composites. PETase hydrolyses PET to produce bis(2-hydroxyethyl) terephthalate (BHET), mono-(2-hydroxyethyl) terephthalate (MHET), terephthalate (TPA), and ethylene glycol (EG), and MHETase catalyzes MHET to TPA and EG. Hence, as shown herein, co-expression of PETase and MHETase in an engineered strain can enable PET degradation to TPA and EG. Thus, in some embodiments of the present disclosure, a biological method is provided for the selective degradation of PET into PET monomers via co-expression and secretion of PETase and MHETase in *Pseudomonas putida*, which can grow well in simple minimal salt medium.

Therefore, the present disclosure relates to biological methods for the selective degradation of PET into PET monomers via co-expression PETase and MHETase in *Pseudomonas putida*, which can grow well in simple minimal salt medium. Among other things, *I. sakaiensis* PETase, ISF6_4831 and MHETase, ISF6_0224 genes were codon optimized for expression in KT2440 including their secretion signal peptides, which are compatible to the *P. putida* chaperone SecB-dependent secretion system. In addition, the genes were integrated into the *P. putida* genome with the tac promoter to enable constitutive expression. In certain embodiment, the term "tac", "Ptac" and "P-Tac" may be used interchangeable to mean a tac promoter. The developed LJ041 strain formed a biofilm on PET. LJ041 enables highly-selectively degradation of PET into monomer TPA via BHET and MHET and confirmed secretion of PETase and MHETase enzymes via the chaperone-dependent native *P. putida* secreting system. These innovations could lead to a *P. putida* strain for selective biological degradation and conversion of PET into bio-derived chemical building blocks.

*I. sakaiensis* PETase, ISF6_4831 and MHETase, ISF6_0224 genes were codon optimized to KT2440 including their secretion signal peptides, which are compatible to the *P. putida* chaperone Sec-dependent secretion system. To confirm secretion of codon optimized PETase in *P. putida* via the *I. sakaienesis* secretion signal peptide, green fluorescent protein (GFP) was genetically linked to the C-terminus of PETase and expressed in *P. putida*. Efficient secretion of GFP-tagged PETase was confirmed via microscopy and immunoprecipitation, see FIG. 1: Panel A illustrates bright field microscopic observation of the strain expressing PETase with GFP tag; Panel B illustrates microscopic observation of GFP signal of the strain expressing PETase with GFP tag; Panel C illustrates GFP signal of the supernatant of wild-type strain and the strain expressing GFP tagged PETase; Panel D illustrates immunoprecipitation of GFP tagged PETase with GFP specific GFP-Trap® (ChromoTek GmbH, Planegg-Martinsried, Germany); and Panel E illustrates a microscopic image of PET particle incubated with the strain expressing GFP tagged PETase.

Figures 2A, 2B, 2C, 2D, 2E, 2F, 2G, 2H, 2I, 2J:
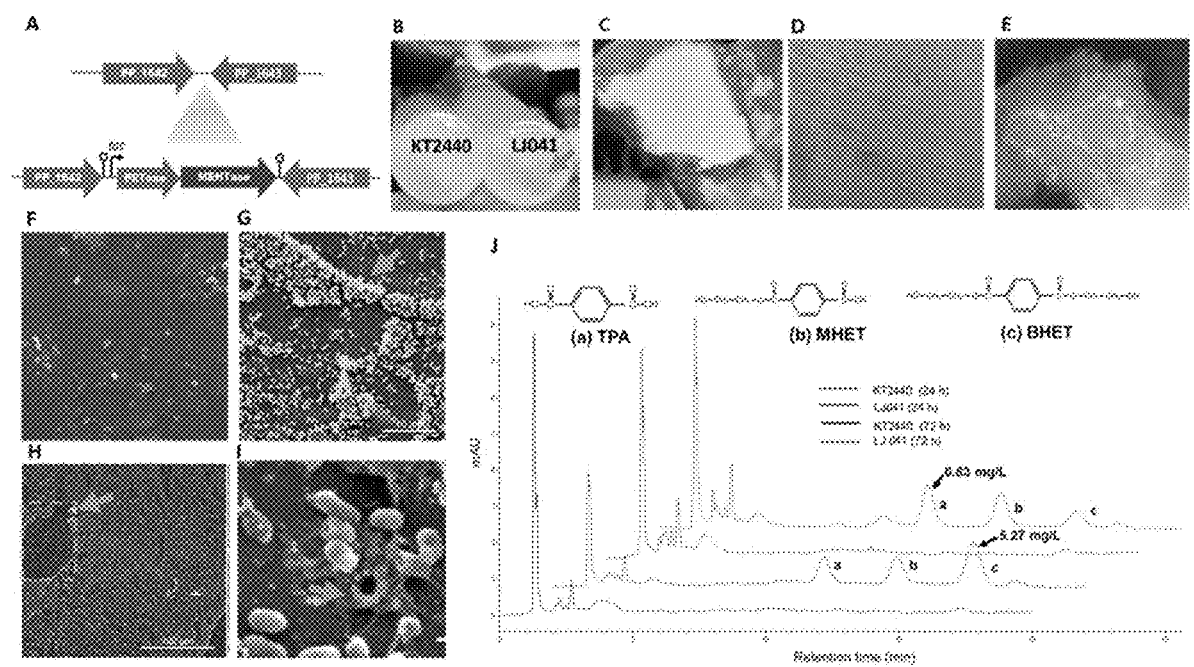
FIG. 2A, FIG. 2B, FIG. 2C, FIG. 2D, FIG. 2E, FIG. 2F, FIG. 2G, FIG. 2H, and FIG. 2I depict degradation results of PET by LJ041 (FIG. 2A) integrated gene cassette (FIG. 2B) visual observation of biofilm of LJ41 on PET film (arrow) (FIG. 2C) fragmenting PET by LJ041 (FIG. 2D) SEM observation of PET particles cultured with KT2440, after 5 days of incubation (FIG. 2E) SEM observation of PET cultured with LJ041, and arrow indicates the biofilm on PET (FIG. 2F) SEM image revealed that KT2440 does not form biofilm on PET (FIG. 2G) SEM observation of LJ041 biofilm forming cells on PET (FIG. 2H) SEM observation of fragmenting PET film (highlighted area with arrow) by LJ041 (FIG. 2I) LJ041 forms holes on PET film (FIG. 2J) HPLC chromatographs of PET-degraded products after 24 h and 72 h. Experiments were conducted in 5 mL M9 medium containing 20 mM glucose and about 60 mg of amorphous PET particle.

Next, referring to FIG. 2, the codon optimized PETase and MHETase genes were successfully integrated into the *P. putida* genome with the tac promoter to enable constitutive expression, and obtained the LJ041 strain (see Panel A). LJ041 formed a biofilm (see FIG. 2, Panels B, E, and G) on amorphous PET coupon and visually observed the fragmenting PET (see FIG. 2, Panels C and H). HPLC analysis revealed that LJ041 enabled highly-selectively degradation of PET into monomer TPA via BHET and MHET (see FIG. 2, Panel J). These results indicate that the codon-optimized signal sequences (which are codon optimized to KT2440), (SEQ ID NO: 16)
"ATGAACTTCCCTCGCGCGTCGCGCCTGATGCAGGCGGCGGTCCTCGGT GGTCTGATGGCAGTCAGCGCCGCGGCCACC" which encode (SEQ ID NO: 17)
"MNFPRASRLMQAAVLGGLMAVSAAATA", and (SEQ ID NO: 18)
"ATGCAGACCACCGTCACCACTATGCTGCTGGCATCGGTCGCCCTGGCC GCC", which is enclosed signal peptide "MQTTVTTMLLASVA-LAA" (SEQ ID NO: 19), for MHETase, respectively, are sufficient for enzyme secretion. These secretion signal peptides may be used for trafficking other proteins in *P. putida* via the Sec-dependent native *P. putida* secreting system. Of note, *Ideonella sakaiensis* 201-F6 grows only in rich-medium but not in the minimal salt medium (data not shown). Thus, the LJ014 has an advantage over the *Ideonella sakaiensis* 201-F6 as an industrial biocatalyst to degrade PET and to subsequently upgrade the degradation products into high-value chemicals. In addition, we introduced PETase and MHETase encoding genes into the genome of *P. putida* EM42 strain via deploying pLJ080 plasmid, the genome reduced version of *P. putida* KT2440, and developed LJ042 strain.

FIG. 2 illustrates degradation results of PET by LJ041 (Panel A) integrated gene cassette (Panel B) visual observation of biofilm of LJ41 on PET film (arrow) (Panel C) fragmenting PET by LJ041 (Panel D) SEM observation of PET particles cultured with KT2440, after 5 days of incubation (Panel E) SEM observation of PET cultured with LJ041, and arrow indicates the biofilm on PET (Panel F) SEM image revealed that KT2440 does not form biofilm on PET (Panel G) SEM observation of LJ041 biofilm forming cells on PET (Panel H) SEM observation of fragmenting PET film (highlighted area with arrow) by LJ041 (Panel I) LJ041 forms holes on PET film (Panel J) HPLC chromatographs of PET-degraded products after 24 h and 72 h. Experiments were conducted in 5 mL M9 medium containing 20 mM glucose and about 60 mg of amorphous PET particle.

Figure 3:
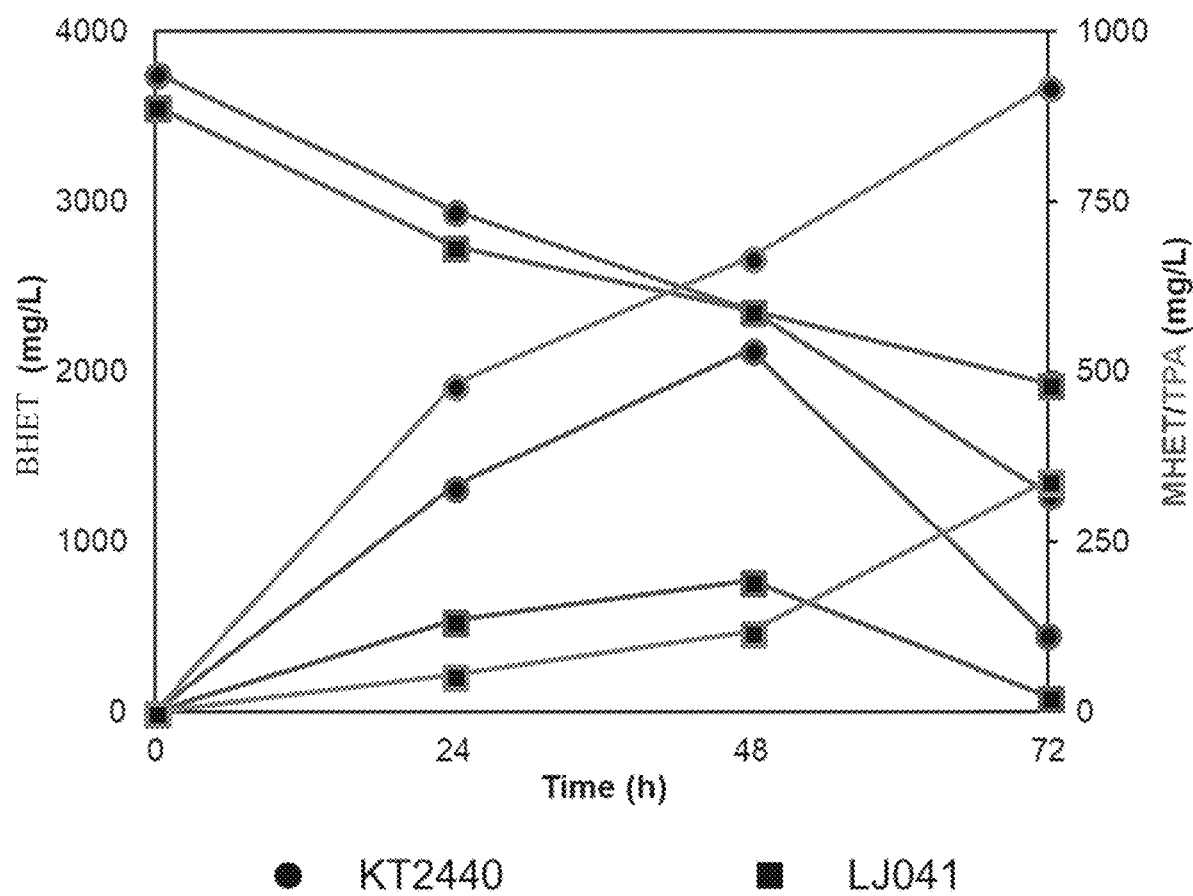
FIG. 3 depicts strain LJ041 that was tested for selective degradation of BHET to TPA. The LJ041 strain converted BHET to TPA at 3-fold higher rate relative to wild-type *P. putida* KT2440 (LJ041:12.8 mg/L/h vs KT2440: 4.7 mg/L/h).

Next, the LJ041 strain was tested for selective degradation of BHET to TPA (see FIG. 3). The LJ041 strain converted BHET to TPA at 3-fold higher rate relative to wild-type *P. putida* KT2440 (LJ041:12.8 mg/L/h vs KT2440: 4.7 mg/L/h). Taken together, this innovation could lead to a *P. putida* strain for selective biological degradation and conversion of PET into bio-derived chemical building blocks.

Materials and Methods

Plasmid construction: Q5 Hot Start High-Fidelity 2× Master Mix (New England Biolabs) and primers synthesized by Integrated DNA Technologies (IDT) were used in all PCR amplification. Plasmids were constructed using Gibson Assembly® Master Mix (New England Biolabs) according to the manufacturer's instructions. Primers used for PCR amplification and Gibson assembly are listed in Table 1. The vector, pBLT-2 (Addgene plasmid #22806) was used for plasmid-based overexpression of PETase with a green fluorescence protein (GFP) tag. Plasmids for gene integration were constructed in pK18sB, which is unable to replicate in *P. putida* KT2440, and contains the kanamycin-resistant marker to select for integration of the plasmid into the genome by homologous recombination and sacB to counter select for a second recombination event to subsequently remove the plasmid backbone from the genome. Detail of plasmids construction is provided in Table 2.

TABLE 1

List of Primers

| Primer ID | 5'-3' |
|---|---|
| oLJ227 | GACATGATTACGAATTCGAGCTCGGTACCCGTGCGATTACTGTGGGAG |
| oLJ232 | CCGGAGGCTTTTGACTCGGAGGCGCGGCGCAGGC |
| oLJ228 | CGGATAACAATTTCACACTGAGTATTGCCTGAACCG |
| oLJ229 | TTCAGGCAATACTCAGTGTGAAATTGTTATCCGCTCACAATTCCACACATTATACGAGCCGATGATTAATTGTCAACAGCTCTTCATCAAGTCAAAACACTATATAGGAACG |
| oLJ230 | ATGTAATCCTTGTTATAGGCTGCAGTTCGCAGTGCG |
| oLJ231 | ACTGCGAACTGCAGCCTATAACAAGGATTACATATAAGGGTATATCAAATGCAGACCACCGTCACC |
| oLJ233 | TGCGCCGCGCCTCCGAGTCAAAAGCCTCCGGTCGGAGGCTTTTGACTTCAAAACCACCCTGCTGTCGATG |
| oLJ234 | CGGCCAGTGCCAAGCTTGCATGCCTGCAGGAAATCTAACTGCCTTCGCCC |
| oLJ406 | TATGTTGTGTGGAATTGTGAGCGGATAACAATTTCACACTTTCATCAAGTCAAAACACTATATAGGAACGAAAC |
| oLJ407 | TCCGCACTGCGAACTGCAGCGGTGGTTCTGAGGAATCTTACATGAGC |
| oLJ408 | GTAAGATTCCTCAGAACCACCGCTGCAGTTCGCAGTGCG |
| oLJ409 | AGTCCAGTTACGCTGGAGTCTGAGGCTCGTCCTGAATGATCTACTTGTAGAGTTCGTC |

TABLE 2

Plasmid construction details

| Plasmid | Purpose | Construction detail |
|---|---|---|
| pLJ080 | Genome integration of overexpressing cassette of PETase and MHETase | The PETase genes cassette was amplified with primers oLJ229 (Fwd) and oLJ230 (Rev), and MHETase oLJ231 (Fwd) and oLJ232 (Rev) using synthesizes gBlock as a temple. The 5' homology region was amplified from *P. putida* KT2440 genomic DNA with primers oLJ227(Fwd), and oLJ228 (Rev), and 3' homology region was amplified with oLJ233 (Fwd) and oLJ234 (Rev). These products were assembled into pK18sB digested with SmaI and SalI. |
| pLJ081 | Overexpressing PETase-GFP | A DNA fragment containing the PETase genewas amplified from pLJ080 with primers oLJ406 (Fwd) and oLJ407 (Rev), and GFP gene fragment was obtained with primers oLJ408 (Fwd) and oLJ409 (Rev), amplified from GFP containing plasmid. This product was assembled into pBLT-2 digested with XbaI and EcoRV. |

Figure 7:
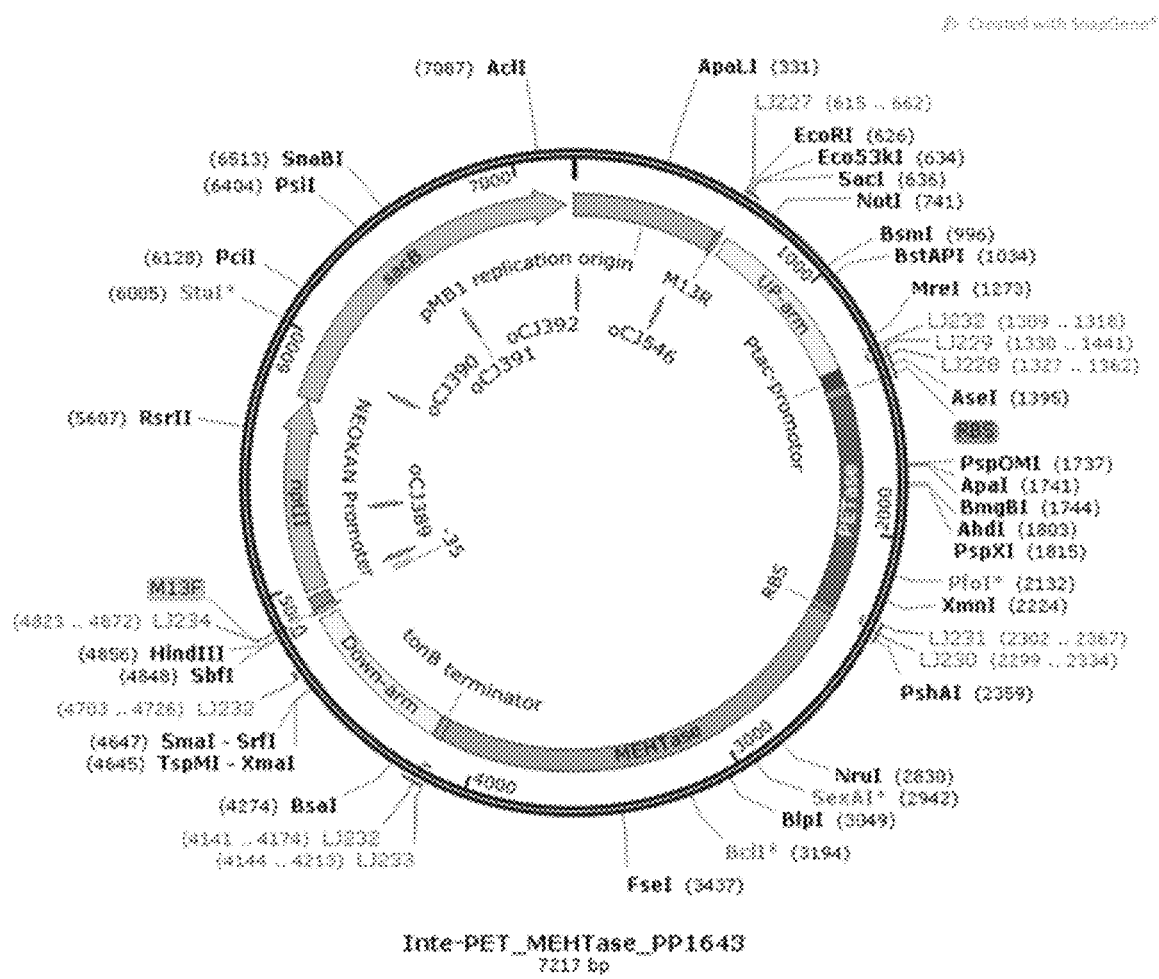
FIG. 7 depicts a plasmid map of pLJ080.

The PETase and MHETase genes from *Ideonella sakaiensis* 201-F6 were codon optimized to *P. putida* KT2440 using online program Optimizer with a random approach (http://genomes.urv.es/OPTIMIZER/), gene fragments were synthesized at Integrated DNA Technologies, Inc, and obtained the double-stranded and linear gBlock, see FIG. 6. The plasmid used for of integration of codon optimize PETase and MHETase to *P. putida* KT2440 contain the approximately 0.7 kb homology region on either side of the intergenic region immediately after PP_1642 and PP_1643 of *P. putida* KT2440. Features include the tac promoter to drive gene expression and a tonB terminator situated behind the fragments cloned into the plasmid backbone, which are depicted in FIG. 7. Synthetic ribosomal binding site (sRBS) were designed using an online program from the Salis laboratory at Penn State University, in front of genes, the designed sRBS (TCATCAAGTCAAAACACTATATAGGAACGAAACC) (SEQ ID NO: 32) of PETase was predicted to have a translation initiation rate (TIR) of 27306.09, and MHETase has a sRBS (TAACAAGGATTACATATAAGGGTATATCAA) (SEQ ID NO: 33) with TIR of 32480.74. Plasmid sequence of pLJ80 is provided in Table S5 in the Appendix. The protein sequences of PETase and MHETase are provided in FIG. 8. Plasmid was transformed into competent NEB 5-alpha FI$^q$ *E. coli* (New England Biolabs) according to the manufacturer's instructions. Transformants were selected on LB plates containing 10 g/L tryptone, 5 g/L yeast extract, 5 g/L NaCl, and 15 g/L agar, supplemented with 50 g/mL kanamycin grown at 37° C. The sequences of all plasmid inserts were confirmed using Sanger sequencing (GENEWIZ, Inc.).

Figure 10:
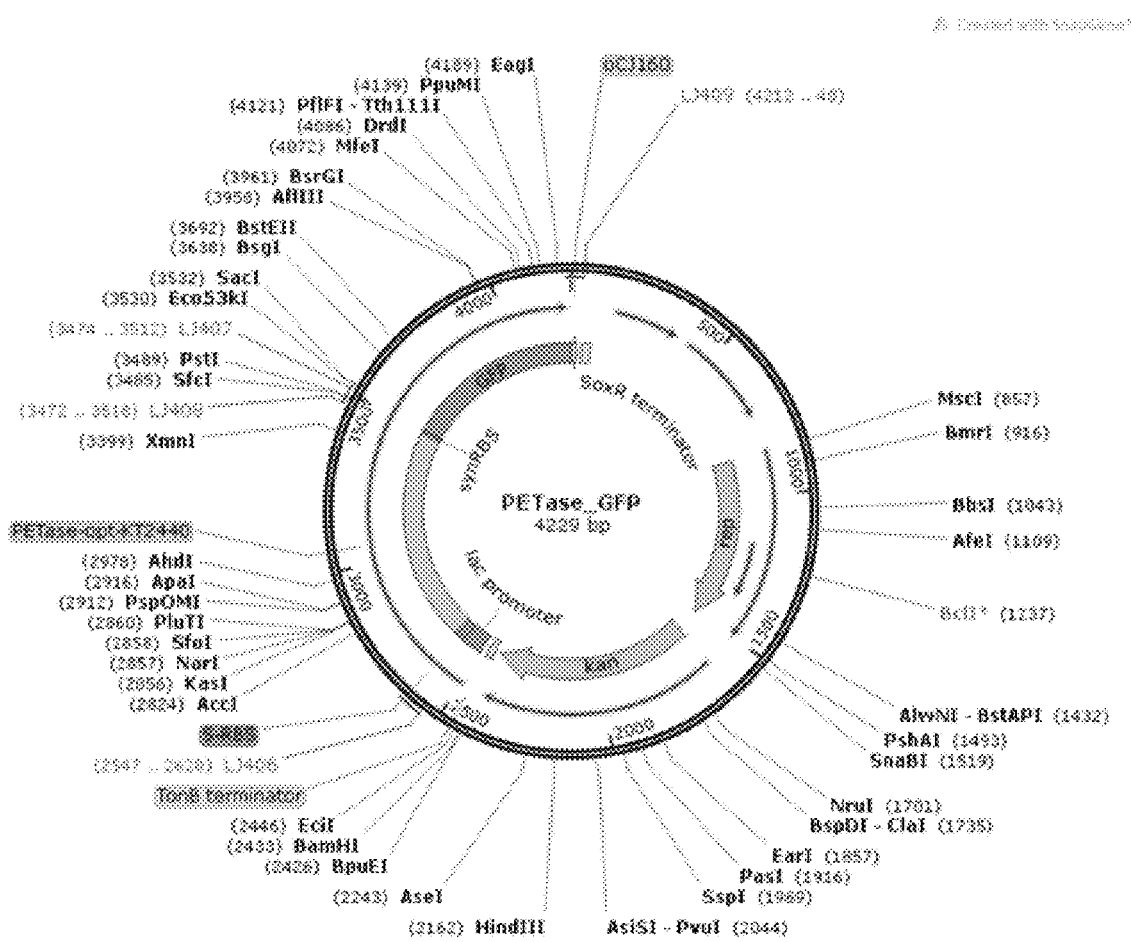
FIG. 10 depicts a plasmid map of pLJ081.
Figure 21:
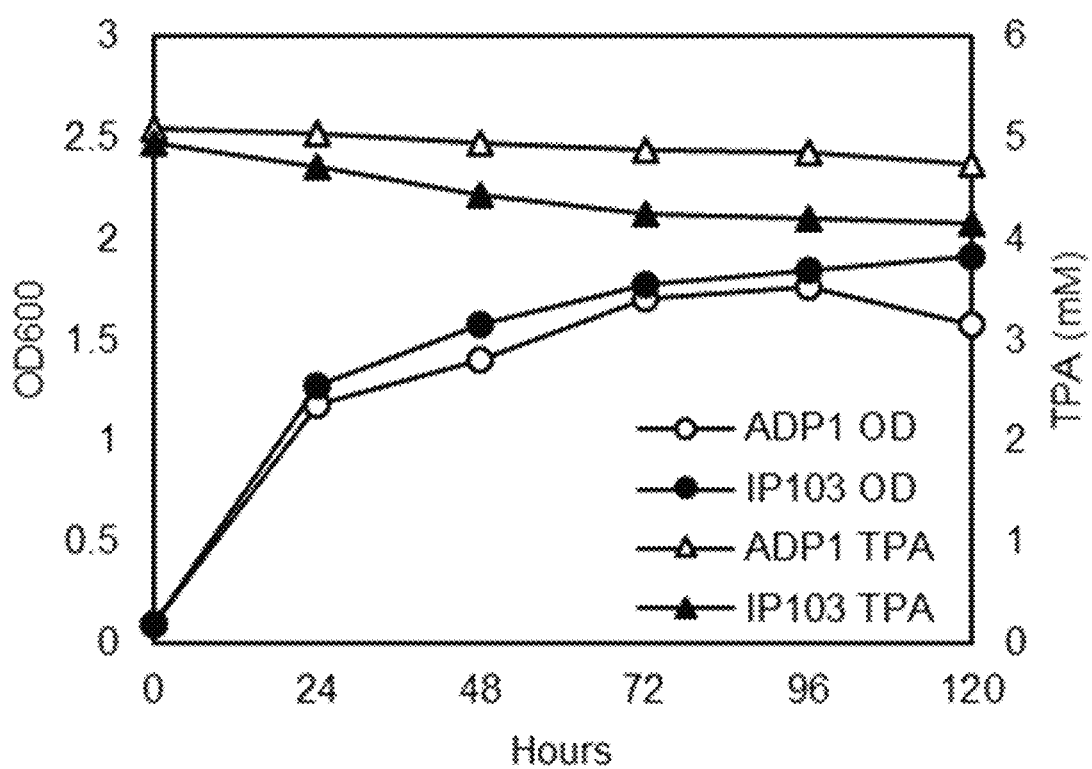
FIG. 21 depicts growth and TPA concentration in a medium containing an engineered *Acinetobacter baylyi* ADP1 strain, IP103, expressing the $tphC_{II}A2_{II}A3_{II}B_{II}A1_{II}$ synthetic genes was grown in *Acinetobacter* minimal media in the presence of 5 mM terephthalic acid and 20 mM pyruvate.
Figure 22:
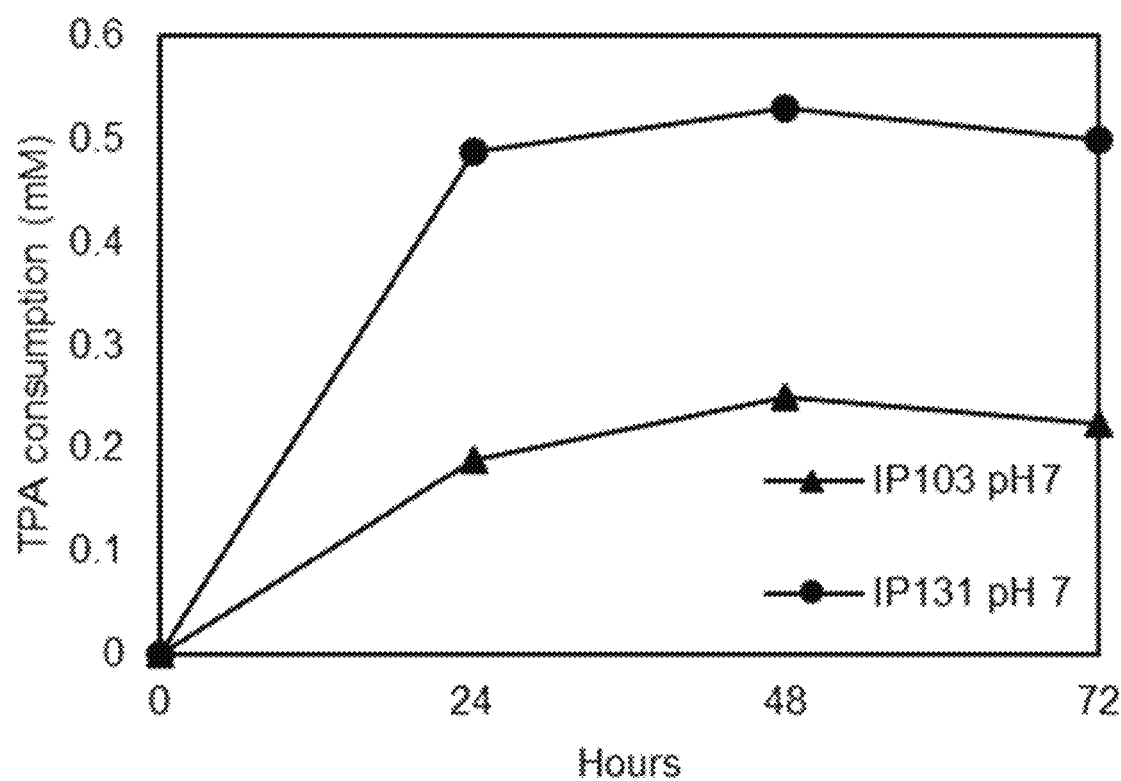
FIG. 22 depicts TPA consumption over time of an engineered *Acinetobacter baylyi* ADP1 strain, IP131, expressing the synthetic terephthalate transporter genes, tpiAB, as well as the $tphC_{II}A2_{II}A3_{II}B_{II}A1_{II}$ genes, and the parent strain, IP103, expressing only the $tphC_{II}A2_{II}A3_{II}B_{II}A1_{II}$ genes, were grown in *Acinetobacter* minimal media supplemented with 5 mM terephthalic acid and 20 mM pyruvate. The strains were fed only at the beginning of the experiment.

Strain construction: *P. putida* KT2440 (ATCC 47054) was used as the basis of strain engineering and gene replacements were made using the antibiotic/sacB system of selection and counter-selection. In an embodiment, the properties and description of some strains disclosed herein is depicted in Table 3. To prepare electrocompetent cells of *P. putida* KT2440 strains, a modified sucrose-based protocol was used. The plasmid was introduced to competent cells via electroporated at 1.6 kV, 25 µF, 200 Ohms. The transformation was plated on an LB agar plate containing 50 µg/ml kanamycin antibiotics and incubated at 30° C. overnight. Initial colonies from the transformation plates were re-streaked on selective LB agar plates and grown at 30° C. overnight to obtain clonal transformants. For sucrose counter-selection, clonal transformants were streaked on YT plates containing 25% (YT+25%; w/v) sucrose (10 g/L yeast extract, 20 g/L tryptone, 250 g/L sucrose, 18 g/L agar), and incubated at 30° C. overnight. The single colony of *P. putida* KT2440 containing the PETase and MHETase genes were successfully isolated. The strain was analyzed for the correct gene replacement by performing a colony PCR at the site of integration. The LJ102 was constructed by transforming pLJ081 plasmid into *P. putida* KT2440, the plasmid map and sequence are provided in FIG. 10 and FIG. 11.

TABLE 3

Strains

| Strain ID | Genotype | Description of strain |
|---|---|---|
| KT2440 | *P. putida* KT2440 | Wild-type *P. putida* KT2440 (ATCC 47054) |
| EM42 | *P. putida* KT2440 Δprophage 1-4 Δflagellum ΔendA-1 ΔendA-2 ΔTn7 ΔhsdRMS ΔTn4652 | Genome reduced strain derived from *P. putida* KT2440 obtained from Victor de Lorenzo's laboratory (Centro Nacional de Biotecnología (CNB-CSIC), Madrid, Spain) |
| LJ102 | KT2440 + pBTL-2-PETase_GFP | KT2440 containing the pBTL-2 plasmid with PETase and GFP |
| LJ041 | KT2440 1642::Ptac::PETase-MHET | KT2440 with the PETase and MHETase cassette integrated within the intergenic region between PP_1642 and PP_1643 |
| LJ042 | EM42 PP 1642::Ptac::PETase-MHET | EM42 with the PETase and MHETase cassette integrated within the intergenic region between PP_1642 and PP_1643 |

PET and BHET degradation experiment: To assess the selective degradation of PET/BHET by the PETase and MHETase expressing strain, shake flask experiments were performed using 125 mL baffled flasks containing 25 mL modified M9 media (6.78 g/L $Na_2HPO_4$, 3.00 g/L $K_2HPO_4$, 0.50 g/L NaCl, 1.66 g/L $NH_4Cl$, 0.24 g/L $MgSO_4$, 0.01 g/L $CaCl_2$, and 0.002 g/L $FeSO_4$) supplemented with 20 mM of glucose and amorphous PET coupons (amorphous PET films with a crystallinity of 14.8±0.2%, synthesized at NREL) or BHET (Obtained from IBM Almaden Research Center, BHET was derived from waste PET bottles via chemical depolymerization process), and inoculated to $OD_{600}$ 0.1 with pre-culture. Pre-cultures of the strains were prepared by inoculating 25 mL M9 medium supplemented with 20 mM glucose in a 125 mL baffled flask to an $OD_{600}$ of 0.05-0.1 and incubating shaking at 225 rpm, 30° C. At mid log phase ($OD_{600}$ 0.5-1.0) cells were harvested by centrifugation at 13,000 rpm, and the cell pellets were washed twice and resuspended in M9 medium without a carbon source. Cultures were incubated shaking at 225 rpm, 30° C. 1 mL samples were collected periodically and subjected to HPLC analysis to detect the degraded products. After the fermentation, PET coupons were subjected to microscopic observation.

Scanning Electron Microscopy (SEM): Imaging by scanning electron microscopy (SEM) was performed using a FEI Quanta 400 FEG instrument under low vacuum (0.45 Torr) operating with the gaseous solid-state detector (GAD). Samples were prepared for imaging by fixation in 2.5% gluteraldehyde buffered in 1×PBS (EMS, Hatfield, PS), dehydration in an ethanol series, then freezing in liquid nitrogen followed by lyophilization. Dry samples were mounted on aluminum stubs using carbon tape, and sputter coated with 9 nm of Ir metal. Images were captured at a beam accelerating voltage of 24 keV.

High performance liquid chromatography (HPLC) analysis: Concentrations of TPA, MHET, and BHET were measured using HPLC by injecting 6 µL of 0.2-µm filter-sterilized culture supernatant onto an Agilent1100 series system (Agilent USA, Santa Clara, CA) equipped with a Phenomenex Rezex RFQ-Fast Fruit H+ column (Phenomenex, Torrance, CA) and cation H+ guard cartridge (Bio-Rad Laboratories, Hercules, CA) at 85° C. A mobile phase of 0.1N sulfuric acid was used at a flow rate of 1.0 mL/min. Diode array detectors were used for compound detection. Compounds were identified by relating the retention times and spectral profiles with standard HPLC grade pure compounds (Sigma Aldrich, St. Louis, MO, USA) and the concentration of each compound was calculated based on a calibration curves generated using pure compounds.

To enable TPA catabolism in *P. putida* KT2440, genes for TPA transport and for conversion of TPA into protocatechuic acid (PCA), an intermediate metabolite of ß-ketoadipate pathway were introduced into the chromosome of *P. putida* strain KT2440. Three different operons containing genes required for TPA catabolism [two operons from *Comamonas* sp. E6 (operon I: tphA2I, tphA3I, tphBI, and tphA1I) and (operon II: tphA2II, tphA3II, tphBII, and tphA1II), and one from *R. jostii* RHA1 (tpaA1, tpaA2, tpaC, and tpaB)], and two different operons containing transport genes [one from *Comamonas* sp. E6 (tphC, tpiA, and tpiB) and one from *R. jostii* RHA1(tpaK) were tested in various combinations (Table 4). Additionally, each operon was placed under control of 3 different promoters of varying strengths (from strongest to weakest: P-Tac, P-549, P-Lac, P-3079). Those gene clusters were successfully integrated into a modified version of *P. putida* KT2440 that has 3 poly-attB genetic islands for DNA insertion via highly efficient phage integrase system.

Figures 5A, 5B, 5C:
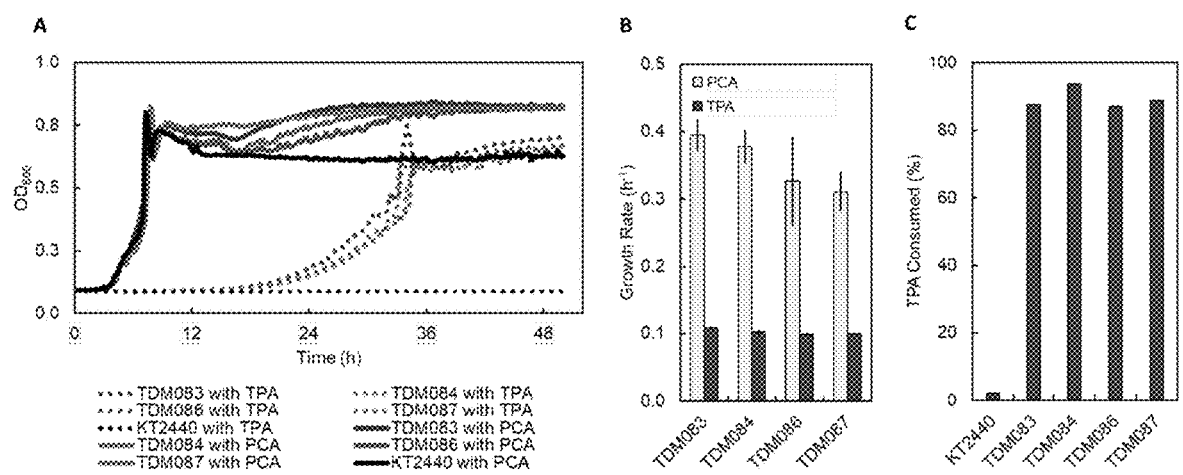
FIG. 5A, FIG. 5B, and FIG. 5C depict engineered *P. putida* KT2440 strains that enable TPA utilization.

In an embodiment, thirty-five strains were generated, of which four had substantial growth with TPA as the sole carbon source. Each of the four strains that were able to metabolize TPA contained one of the two *Comamonas* sp. E6 catabolic operons (I or II) in combination with the *R. jostii* transporter. Robust expression was a requirement for TPA utilization, as growth was only detected when catabolic and transport genes were expressed from the strongest tested promoters (P-Tac or P-549). Of note, the growth data revealed that neither *Comamonas* sp. E6 TPA transporter nor *R. jostii* RHA1 catabolic genes enable TPA catabolism in *P. putida* KT2440. Growth in minimal media containing either 10 mM TPA or 10 mM PCA was compared for each of the TPA catabolizing strains. An extended lag phase and about a 3-fold slower growth rate for all strains indicated that TPA is not used as efficiently as PCA as a substrate (FIGS. 5A and 5B, Table 5). However, quantification of TPA from late exponential phase cultures grown in minimal media with 10 mM TPA indicated that about 90% of TPA was consumed (FIG. 5C). Ongoing experiments are aimed at optimizing import and processing of TPA. Additionally, the ultimate objective of this project is to use *P. putida* for the valorization of TPA into other high value products, such as ß-ketoadipate. To that end, the genes that facilitate ß-ketoadipate consumption, pcaIJ, have been deleted from the TPA utilizing strains to allow ß-ketoadipate accumulation, and the strains have been confirmed by PCR.

TABLE 4

Generated strains of *P. putida* containing genes for terephthalic acid transport and catabolism under control of promoters with varying strengths.

| | Catabolic Genes | | | Transport Gene(s) | | | |
|---|---|---|---|---|---|---|---|
| TDM# | Source Organism | Operon | Promoter | Source Organism | Operon | Promoter | TPA growth |
| 56 | *Comamonas* | tphA2$_I$A3$_I$B$_I$Al$_I$ | P-Tac | *Comamonas* | tphC- | P-549 | No |
| 57 | sp. E6 | | P-Tac | sp. E6 | tpiBA | | No |
| 58 | | | P-Lac | | | | No |
| 59 | *Comamonas* | tphA2$_{II}$A3$_{II}$B$_{II}$Al$_{II}$ | P-Tac | *Comamonas* | tphC- | P-549 | No |
| 60 | sp. E6 | | P-Tac | sp. E6 | tpiBA | | No |
| 61 | | | P-Lac | | | | No |
| 62 | *Rhodococcus* | tpaA1A2CB | P-Tac | *Comamonas* | tphC- | P-549 | No |
| 63 | *jostii* RHA1 | | P-Tac | sp. E6 | tpiBA | | No |
| 64 | | | P-Lac | | | | No |
| 65 | *Comamonas* | tphA2$_I$A3$_I$B$_I$Al$_I$ | P-Tac | *Comamonas* | tphC- | P-Lac | No |
| 66 | sp. E6 | | P-Tac | sp. E6 | tpiBA | | No |
| 67 | | | P-Lac | | | | No |
| 68 | *Comamonas* | tphA2$_{II}$A3$_{II}$B$_{II}$Al$_{II}$ | P-Tac | *Comamonas* | tphC- | P-Lac | No |
| 69 | sp. E6 | | P-Tac | sp. E6 | tpiBA | | No |
| 70 | | | P-Lac | | | | No |
| 71 | *Rhodococcus* | tpaA1A2CB | P-Tac | *Comamonas* | tphC- | P-Lac | No |
| 72 | *jostii* RHA1 | | P-Tac | sp. E6 | tpiBA | | No |
| 73 | | | P-Lac | | | | No |
| 74 | *Comamonas* | tphA2$_I$A3$_I$B$_I$Al$_I$ | P-Tac | *Comamonas* | tphC- | P-3079 | No |
| 75 | sp. E6 | | P-Tac | sp. E6 | tpiBA | | No |
| 76 | | | P-Lac | | | | No |
| 77 | *Comamonas* | tphA2$_{II}$A3$_{II}$B$_{II}$A$_{II}$ | P-Tac | *Comamonas* | tphC- | P-3079 | No |
| 78 | sp. E6 | | P-Tac | sp. E6 | tpiBA | | No |
| 79 | | | P-Lac | | | | No |
| 80 | *Rhodococcus* | tpaA1A2CB | P-Tac | *Comamonas* | tphC- | P-3079 | No |
| 81 | *jostii* RHA1 | | P-Tac | sp. E6 | tpiBA | | No |
| 82 | | | P-Lac | | | | No |
| 83 | *Comamonas* | tphA2$_I$A3$_I$B$_I$Al$_I$ | P-Tac | *Rhodococcus* | tpaK | P-549 | Yes |
| 84 | sp. E6 | | P-Tac | *jostii* RHA1 | | | Yes |
| 85 | | | P-Lac | | | | No |
| 86 | *Comamonas* | tphA2$_{II}$A3$_{II}$B$_{II}$Al$_{II}$ | P-Tac | *Rhodococcus* | tpaK | P-549 | Yes |
| 87 | sp. E6 | | P-Tac | *jostii* RHA1 | | | Yes |
| 88 | | | P-Lac | | | | No |
| 89 | *Rhodococcus* | tpaA1A2CB | P-Tac | *Rhodococcus* | tpaK | P-549 | No |
| 90 | *jostii* RHA1 | | P-Tac | *jostii* RHA1 | | | No |

TABLE 5

Growth characteristics of TPA utilizing strains of
P. putida in minimal medium containing either 10 mM
TPA or 10 mM PCA as the sole growth substrate.

| Strain | Substrate | Lag Phase (h) | Growth Rate ($h^{-1}$) | Doubling Time (h) |
|---|---|---|---|---|
| TDM083 | TPA | 16.4 ± 0.1 | 0.108 ± 0.002 | 6.41 ± 0.13 |
| TDM084 | TPA | 16.4 ± 0.8 | 0.102 ± 0.003 | 6.81 ± 0.20 |
| TDM086 | TPA | 17.4 ± 0.9 | 0.099 ± 0.003 | 7.01 ± 0.19 |
| TDM087 | TPA | 17.6 ± 0.5 | 0.099 ± 0.001 | 6.98 ± 0.07 |
| KT2440 | TPA | No Growth | No Growth | No Growth |
| TDM083 | PCA | 2.8 ± 0.0 | 0.395 ± 0.024 | 1.76 ± 0.10 |
| TDM084 | PCA | 2.8 ± 0.0 | 0.378 ± 0.026 | 1.84 ± 0.13 |
| TDM086 | PCA | 2.9 ± 0.1 | 0.327 ± 0.066 | 2.17 ± 0.40 |
| TDM087 | PCA | 2.8 ± 0.3 | 0.311 ± 0.029 | 2.24 ± 0.22 |
| KT2440 | PCA | 2.6 ± 0.3 | 0.300 ± 0.010 | 2.31 ± 0.08 |

Different versions of a synthetic operon coding for a terephthalic acid degradation pathway were constructed for chromosomal integration and expression in *Acinetobacter baylyi* ADP1. This operon includes codon-optimized versions of the genes $tphC_{II}A2_{II}A3_{II}B_{II}A1_{II}$ and tpiBA from *Comamonas* sp. E6 under control of a constitutive promoter, with each gene being preceded by a synthetic ribosome binding site sequence. The description and accession numbers for the wild-type *Comamonas* sp. E6 $tphC_{II}A2_{II}A3_{II}B_{II}A1_{II}$ and tpiBA genes are listed in Table 6. For the homologous recombination and insertion of the operon in the chromosome of *Acinetobacter baylyi* ADP1, upstream and downstream homology arms of ~2000 bp were amplified from genomic DNA and assembled by overlap extension PCR to flank the synthetic genes. Linear DNA fragments were transformed into naturally competent *Acinetobacter baylyi* ADP1 cells as described in the literature.

TABLE 6

| Gene | Protein accession number | Description |
|---|---|---|
| $tphC_{II}$ | BAE47084.1 | Periplasmic terephthalate binding receptor |
| $tphA2_{II}$ | BAE47085.1 | Oxygenase large subunit of terephthalate 1,2-dioxygenase |
| $tphA3_{II}$ | BAE47086.1 | Oxygenase small subunit of terephthalate 1,2-dioxygenase |
| $tphB_{II}$ | BAE47087.1 | 1,2-dihydroxy-3,5-cyclohexadiene-1,4-dicarboxylate dehydrogenase |
| $tphA1_{II}$ | BAE47088.1 | Reductase component of terephthalate 1,2-dioxygenase |
| tpiB | BAN66715.1 | Small transmembrane protein of the aromatic acids transporter |
| tpiA | BAN66716.1 | Large transmembrane protein of the aromatic acids transporter |

Figures 1A, 1B, 1C, 1D, 1E:
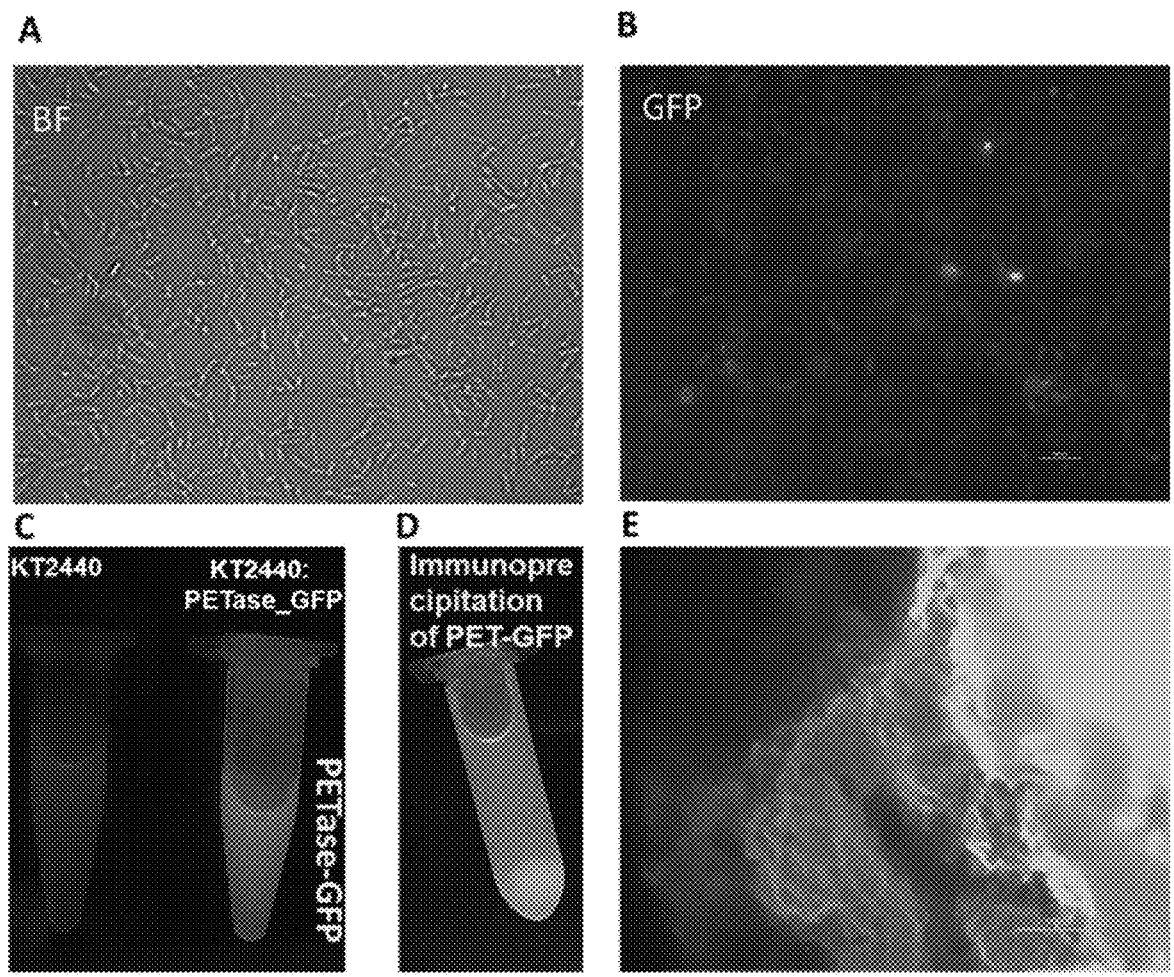
FIG. 1A, FIG. 1B, FIG. 1C, FIG. 1D, FIG. 1E depict.

In a first shake-flask experiment, an engineered *Acinetobacter baylyi* ADP1 strain, IP103, expressing the $tphC_{II}A2_{II}A3_{II}B_{II}A1_{II}$ synthetic genes was grown in *Acinetobacter* minimal media in the presence of 5 mM terephthalic acid and 20 mM pyruvate, the latter being fed every 24 hours to support cell growth. As seen in FIG. 1, more terephthalic acid was consumed by IP103 than by the wild-type strain. The slight decrease in TPA concentration for the wild-type strain is an effect of the dilution caused by feeding daily with 20 mM pyruvate to support cell growth.

Genes expressing the terephthalate transporter from *Comamonas* sp. E6, tpiBA, were then similarly codon optimized and incorporated into the genome of IP103 downstream of the $tphC_{II}A2_{II}A3_{II}B_{II}A1_{II}$ genes, such that expression of all of these genes was driven as an operon by the same promoter. In a shake-flask experiment, this new strain expressing the synthetic terephthalate transporter genes, tpiAB, as well as the $tphC_{II}A2_{II}A3_{II}B_{II}A1_{II}$ genes, IP131, and the parent strain expressing only the $tphC_{II}A2_{II}A3_{II}B_{II}A1_{II}$ genes, IP103, were grown in *Acinetobacter* minimal media supplemented with 5 mM terephthalic acid and 20 mM pyruvate, fed only at the beginning of the experiment. As seen in FIG. 2, IP131 was able to degrade terephthalic acid more quickly, than IP103, indicating that expression of the terephthalate transporter improved the ability of this strain to metabolize this substrate.

Poly(ethylene terephthalate) (PET) is among the most widely consumed synthetic plastics and thus also a major component of plastic waste in landfills. The development of chemical catalysis approaches for PET depolymerization to monomers offers new options for both closed-loop recycling and open-loop upcycling of PET, the latter of which can leverage biological transformations to higher-value products. To that end, here we apply catalytic glycolysis to deconstruct PET to bis(2-hydroxyethyl) terephthalate (BHET). For BHET conversion to terephthalate and ethylene glycol, we engineer *Pseudomonas putida* KT2440 with PETase and MHETase enzymes from *Ideonella sakaiensis*. We further engineer *P. putida* to convert terephthalate to a performance-advantaged bioproduct, b-ketoadipic acid, and for improved utilization of ethylene glycol, a byproduct of BHET catabolism. In a bioreactor, we produce 15.1±0.6 g/L of b-ketoadipic acid (b KA) from BHET at 76±3% molar yield. Lastly, we demonstrate conversion of catalytically depolymerized PET to bKA. Overall, this work highlights the potential of tandem catalytic deconstruction and biological conversion as a means to upcycle waste PET.

The accumulation of plastics in landfills and the natural environment is now widely recognized to be a global pollution crisis. As a primary component of a holistic solution to address this global challenge, chemical recycling technologies hold considerable promise to break down waste synthetic polymers into processable intermediates, including the original monomers. The resulting intermediates from these deconstruction processes can be either reformulated into chemically identical materials, known as closed-loop recycling, or converted into new materials, known as open-loop recycling. Open-loop recycling offers the potential to both incentive the economics of waste plastics reclamation via the production of higher-value materials (upcycling), as well as produce new materials that are more readily recyclable than the parent polymer. For open-loop polymer recycling strategies, a portfolio of synthetic chemistry and synthetic biology-based transformations can be leveraged and combined to produce new building blocks.

Figures 23A, 23B, 23C, 23D:
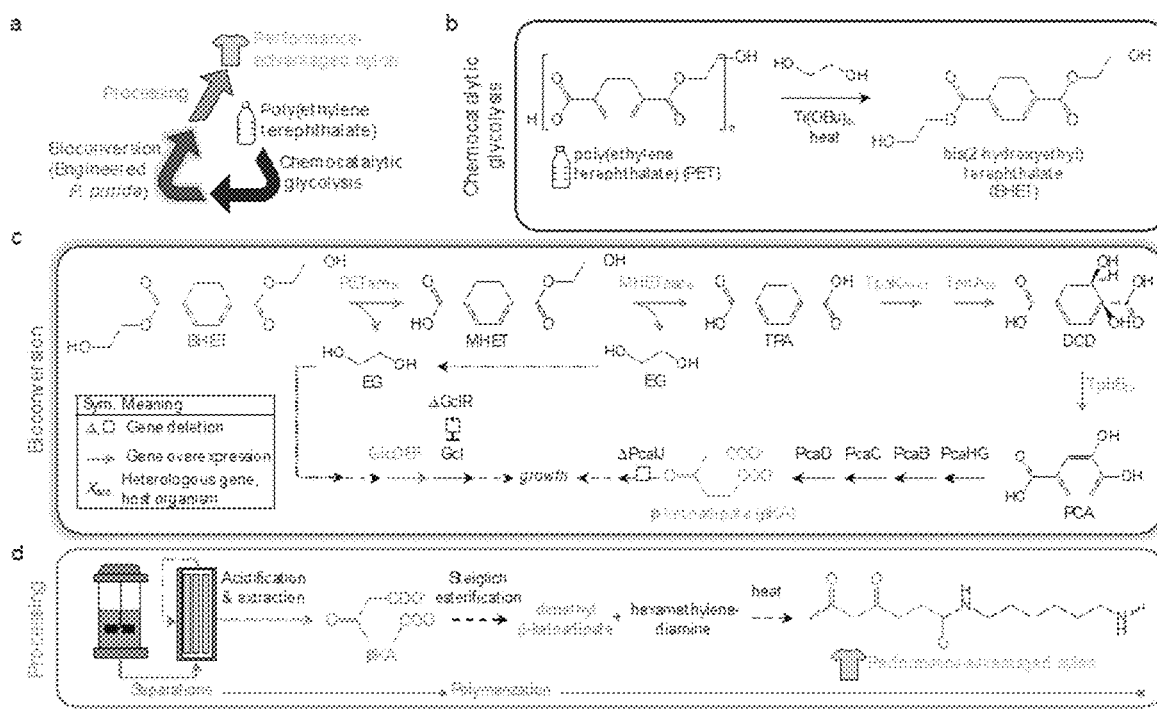
FIGS. 23a, 23b, 23c, and 23d depict conceptual process and metabolic pathways to enable open-loop upcycling of poly(ethylene terephthalate) (PET) to β-ketoadipate (βKA) by an engineered *P. putida* strain.

Due to its widespread use in single-use beverage bottles, clothing, carpet, and food packaging, poly(ethylene terephthalate) (PET) has long been a primary target substrate for chemical recycling. Today, only single-use beverage bottles and other rigid PET materials are able to be recycled at any appreciable global scale via mechanical recycling, which primarily converts the polymer to lower-value textiles or fibers, meaning ultimately the plastic waste will still end its functional life in the landfill or into the natural environment. Chemical recycling approaches for PET offer the potential to dramatically increase the volume of material that can be recycled to include textiles, films, packaging, etc. Deconstruction strategies for PET into monomers include glycolysis, chemical hydrolysis, enzymatic hydrolysis methanolysis, and thermal depolymerization, among many emerging, catalysis-enabled options. Glycolysis is a particularly promising approach to depolymerize PET to bis(2-hydroxyethyl) terephthalate (BHET) in the presence of various catalysts when ethylene glycol is used as the reactant (and typically the solvent as well) (FIG. 23). Upon purification, BHET can be readily converted back to PET, or converted to higher-value products.

The potential for metabolic engineering, synthetic biology, biochemistry, and industrial biotechnology to play a role in chemical recycling of plastics is well recognized. For biological conversion of BHET to value-added chemicals, there are a considerable number of existing components that can be combined to enable its biological conversion. For BHET hydrolysis into its constituent building blocks, the two-component PETase and MHETase enzyme system discovered by Yoshida and co-workers from *Ideonella sakaiensis* 201-F6 converts BHET into terephthalate (TPA) and ethylene glycol (EG).16 Microbial conversion metabolic pathways for both PET building blocks, TPA and EG, have been reported. For EG, we previously reported engineering of the aromatic catabolic bacterium, *Pseudomonas putida* KT2440 (hereafter *P. putida*), to convert up to 2 M EG substrates in shake flasks cultivations by constitutive overexpression of native genetic machinery. Additional work using adaptive laboratory evolution (ALE) in the same strain also resulted in similar performance, and revealed the importance of a key regulator in EG catabolism in *P. putida*. The catabolic pathways for TPA, including both transporters and enzymes, have been described in diverse bacteria, including *Comomonas* sp. E6 (hereafter *Comamonas*), *Rhodococcus jostii* RHA1 (hereafter *R. jostii*), *Pseudomonas* sp. GO16, and *I. sakaiensis* 201-F6 (hereafter *I. sakaiensis*). Conveniently, TPA catabolism in these microbes all proceeds via protocatechuate (PCA), a central intermediate in aerobic aromatic catabolism including in *P. putida*.22 This central intermediate can be converted into aromatic catabolic intermediates such as muconic acid or β-ketoadipic acid, or converted to central carbon metabolism to produce any number of accessible products, such as polyhydroxyalkanoates.

In the current work, we present a metabolic engineering effort that culminates in a *P. putida* strain which expresses PETase and MHETase for BHET conversion to TPA, transforms TPA into a performance-advantaged bioproduct, β-ketoadipic acid, and rapidly utilizes the byproduct EG (FIG. 23). We conduct bioreactor cultivations to demonstrate 15.1±0.6 g/L βKA titers and demonstrate βKA biosynthesis from a crude PET chemocatalytic glycolysis product. Overall, this study contributes to the emerging literature in the use of metabolic engineering for the important problem of plastics upcycling.

RESULTS

Deregulation and Overexpression of Native *P. puitda* Genes Improved EG Catabolism Two units of EG are released for every BHET molecules (FIG. 23) and glycolyzed PET streams will likely contain trace EG despite solvent recycling. Robust tolerance to, and utilization of, EG is therefore required for a biocatalyst converting PET-derived BHET to βKA. *P. putida* natively catabolizes EG albeit slowly and in a heavily regulated process, likely due to the acute toxicity of pathway intermediates. Constituitive overexpression of the gclDEFG: PP_3794 and gcl:hyi:glxR:ttuD:pykF catabolic operons17 (strain MFL185) or deletion of the glcR repressor18 which de-represses expression of gcl:hyi:glxR:ttuD:pykF (strain RC002) (FIG. 23) have been shown to improve EG utilization but both engineering modifications had not yet been combined into a single strain.

Figures 24A, 24B, 24C:
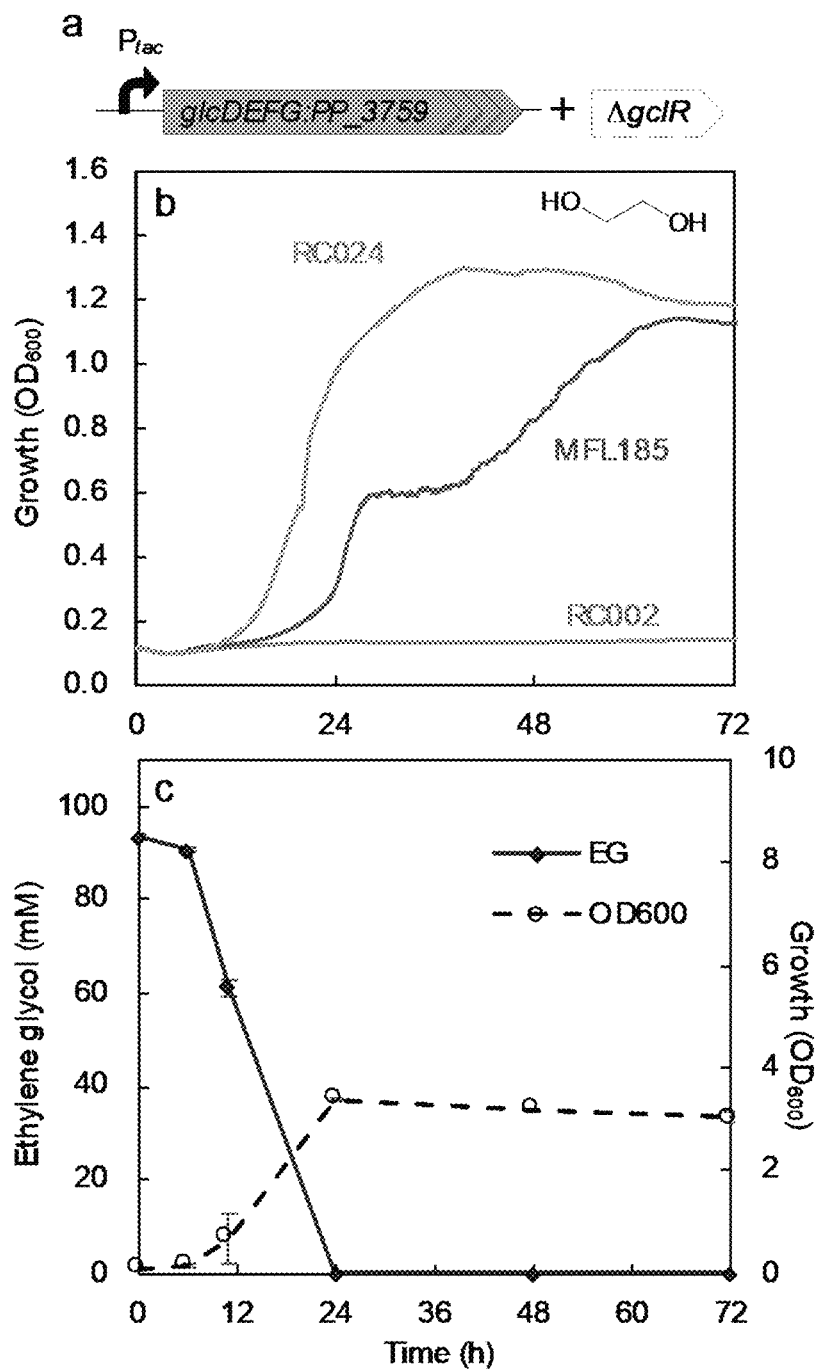
FIGS. 24a, 24b, and 24c depict Growth and utilization of ethylene glycol (EG) by engineered *P. putida*.
Figures 29A, 29B, 29C:
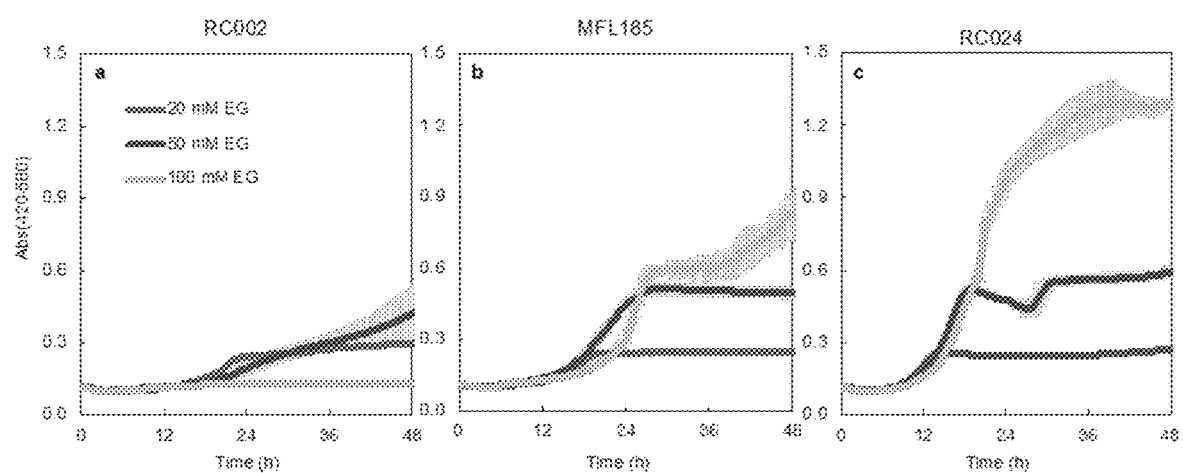
FIGS. 29a, 29b, 29c depict Growth of engineered P. putida strains in ethylene glycol. Growth in M9 minimal medium supplemented with 20, 50, or 100 mM EG of (FIG. 29a) RC002 (P. putida ΔgclR), (FIG. 29b) MFL185 (P. putida fpvA:$P_{tac}$:gcl:hyi:glxR:ttuD:pykF $P_{tac}$*:glcDEFG:PP_3749), or (FIG. 29c) RC024 (P. putida ΔgclR $P_{tac}$:glcDEFG:PP_3749). *, a 49 bp mutation was found in the $P_{tac}$ promoter, as described in Franden et al. (2021). Growth was monitored in a BioscreenC® as wideband absorbance every 15 min. Error bars represent the standard deviation among biological triplicates.
Figure 30:
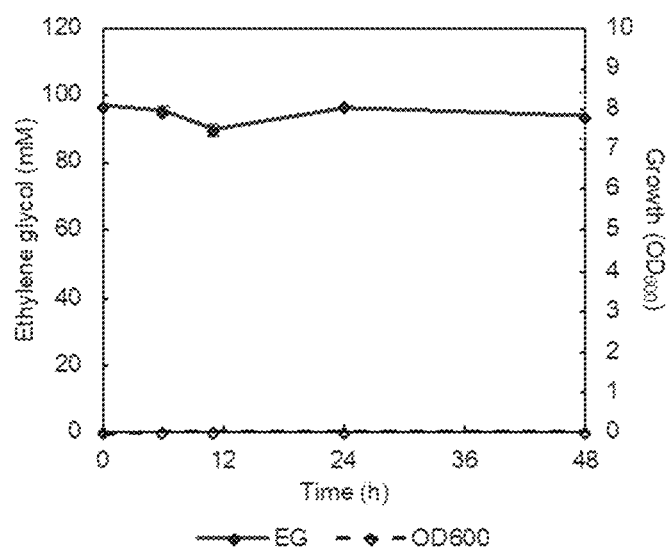
FIG. 30 depicts EG concentration and OD600 over time in non-inoculated controls. Analyte concentrations and OD600 of shaken flasks with M9 minimal medium supplemented with 100 mM EG. Error bars represent the standard deviation among biological triplicates.

We combined the overexpression of gclDEFG:PP_3794 and a gclR deletion into one strain, named RC024 (strain genotypes are provided in Table 1). RC024 was compared to RC002 and MFL185 in M9 minimal medium with 100 mM EG as the sole carbon source. As compared to MFL185, RC024 displayed an improved growth rate (0.26±0.0 vs. 0.17±0.01 h-1, respectively; p<0.05, paired one-tailed t-test) and decreased lag phase (11.7±0.5 vs. 16±1.1 h, respectively; p<0.05), whereas RC002 did not display any growth in 100 mM EG (FIG. 24a) but did at lower concentrations of 20 and 50 mM (FIG. 29). Evaluation in shaken flasks was conducted to confirm complete EG utilization. EG concentrations were stable in non-inoculated controls (FIG. 30). Complete utilization of 100 mM EG was observed within 24 h of RC024 cultivations (FIG. 24b). Together the growth data demonstrates combining deregulation (ΔgclR) and overexpression (Ptac:glcDEFG:PP_3749) of native *P. puitda* genes into a single strain improves EG utilizaiton.

TABLE 7

Bacterial strains utilized in this study. Strains for which data is provided in the main text are listed here in alphabetical order; see Table 10 for a complete list and accompanying construction details. Subscript indicates the host organism for heterologously expressed genes: E6, Comamonas sp. E6; RHA1, *Rhodococcus jostii* RHA1; Is, *Ideonella sakiensis*.

| Name | Genotype | Ref |
|---|---|---|
| *P. putida* | Wild-type *Pseudomonas putida* KT2440 (KT2440) | ATCC ® 47054 |
| AW165 | *P. putida* ΔhsdM-hsdR::$P_{tac}$:tphA2$_{II}$A3$_{II}$B$_{II}$A1$_{II\text{-}E6}$ fpvA:$P_{tac}$:tpaK$_{RHA1}$ $P_{tac}$:glcDEFG:PP_3749 ΔgclR::PETase$_{Is}$:MHETase$_{Is}$ ΔpcaIJ | This study |
| TDM083 | | |
| TDM084 | | |
| TDM086 | | |
| TDM087 | | |
| TDM461 | *P. putida* ΔhsdM-hsdR::$P_{tac}$:tphA2$_{II}$A3$_{II}$B$_{II}$A1$_{II\text{-}E6}$ fpvA:$P_{tac}$:tpaK$_{RHA1}$ | This study |
| MFL185 | | |
| RC002 | *P. putida* ΔgclR | This study |
| RC024 | *P. putida* ΔgclR $P_{tac}$:glcDEFG:PP_3749 | This study |
| RC025 | *P. putida* ΔhsdM-hsdR::$P_{tac}$:tphA2$_{II}$A3$_{II}$B$_{II}$A1$_{II\text{-}E6}$ fpvA:$P_{tac}$:tpaK$_{RHA1}$ ΔgclR | This study |
| RC026 | *P. putida* ΔhsdM-hsdR::$P_{tac}$:tphA2$_{II}$A3$_{II}$B$_{II}$A1$_{II\text{-}E6}$ fpvA:$P_{tac}$:tpaK$_{RHA1}$ $P_{tac}$:glcDEFG:PP_3749 ΔgclR | This study |

TABLE 7-continued

Bacterial strains utilized in this study. Strains for which data is provided in the main text are listed here in alphabetical order; see Table 10 for a complete list and accompanying construction details. Subscript indicates the host organism for heterologously expressed genes: E6, Comamonas sp. E6; RHA1, *Rhodococcus jostii* RHA1; Is, *Ideonella sakiensis*.

| Name | Genotype | Ref |
|---|---|---|
| RC038 | P. putida ΔhsdM-hsdR::P$_{tac}$:tphA2$_{II}$A3$_{II}$B$_{II}$A1$_{II-E6}$ fpvA:P$_{tac}$:tpaK$_{RHA1}$ P$_{tac}$:glcDEFG:PP_3749 ΔgcIR::PETase$_{Is}$:MHETase$_{Is}$ | This study |
| RC043 | P. putida ΔhsdM-hsdR::P$_{tac}$:tphA2$_{II}$A3$_{II}$B$_{II}$A1$_{II-E6}$ fpvA:P$_{tac}$:tpaK$_{RHA1}$ P$_{tac}$:glcDEFG:PP_3749 ΔgcIR::PETase$^{S238F/W159H}_{Is}$:MHETase$_{Is}$ | This study |

RC002, MFL185, and RC024 in M9 minimal medium plus 100 mM EG as the sole carbon source. Growth was measured in a Tecan Infinite® F500 at 30° C. (c) Growth and EG concentrations of RC024 shaken flask cultivations in M9 minimal medium supplemented with 100 mM EG as the sole carbon source. Error bars represent the standard deviation among biological triplicates. Strain genotypes are provided in Table 7.

Heterologous expression of tpaK and tphA2A3BA1 enabled TPA catabolism by *P. putida*.

Figures 25A, 25B, 25C, 25D, 25E:
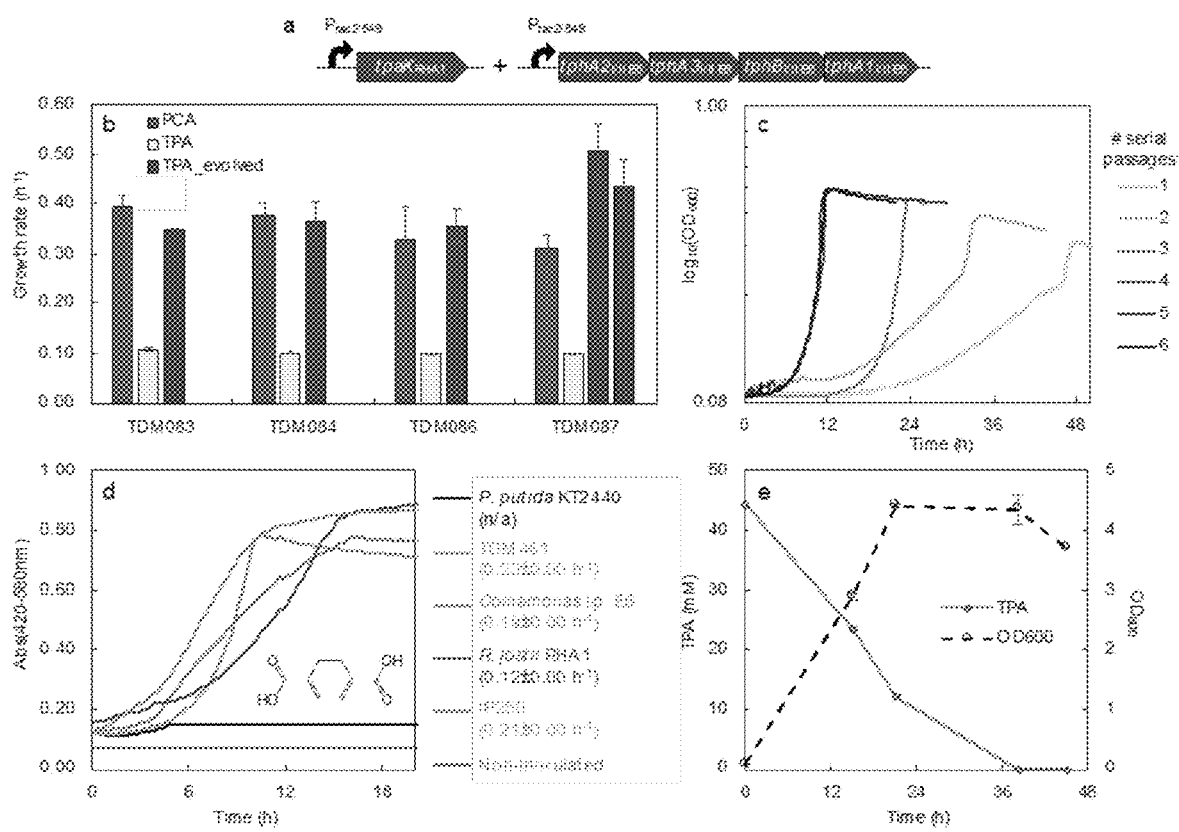
FIGS. 25a, 25b, 25c, 25d, and 25e depict the engineered catabolism of terephthalate (TPA) in *P. putida*.

TPA is the product of PETase- and MHETase-mediated BHET breakdown but is not natively catabolized natively by *P. putida* (FIG. 25d). TPA catabolism has been reported in *Comomonas* sp. E6, *R. jostii, Pseudomonas* sp. GO16, and *I. sakaiensis*, beginning by hydroxylation of the aromatic ring via a TPA dioxygenase (TphA) and followed by conversion to PCA via a diol dehydrogenase (TphB, FIG. 23). For heterologous expression in *P. putida*, we sourced two operons from *Comamonas* (tphA2IA3IBIA1I and tphA2IIA3IIBIIA1II) and a third from *R. jostii*, (tpaA1A2CB). Each operon was driven by one of three promoters: Ptac2, P549 (a lower expression Ptac derivative), or Plac. Three promoters and three catabolic operons combined to generate nine expression cassettes each built into a plasmid (Tables 8-10).

Aromatic carboxylates are predicted to minimally passively diffuse across a phospholipid bilayer akin to the bacterial inner membrane, so we hypothesized that active TPA transport is necessary for TPA catabolism in *P. putida*. In *R. jostii*, the TPA transporter is encoded by tpaK. In *Comamonas*, tphC and tpiBA are required for TPA uptake which were combined into a single operon for expression in *P. putida*. DNA constructs were built with both the P549 and Plac promoters, resulting in four plasmids (Tables 8-10).

A combinatorial library of 36 *P. putida* variants was built by moving one of the catabolic plasmids and one of the transport plasmids into the *P. putida* genome via insertion into a landing pad based on the previously-developed high efficiency site-specific recombination system.36 All isolates grew with PCA as the sole carbon source, as expected. Growth in TPA as the sole carbon source was observed only by four of the 36 strains—TDMM083, TDM084, TDM086, and TDM087—all of which harbor plasmids expressing the tpaK transporter combined with either tph catabolic operon from *Comamonas* (FIGS. 25a-b).

Figures 31A, 31B:
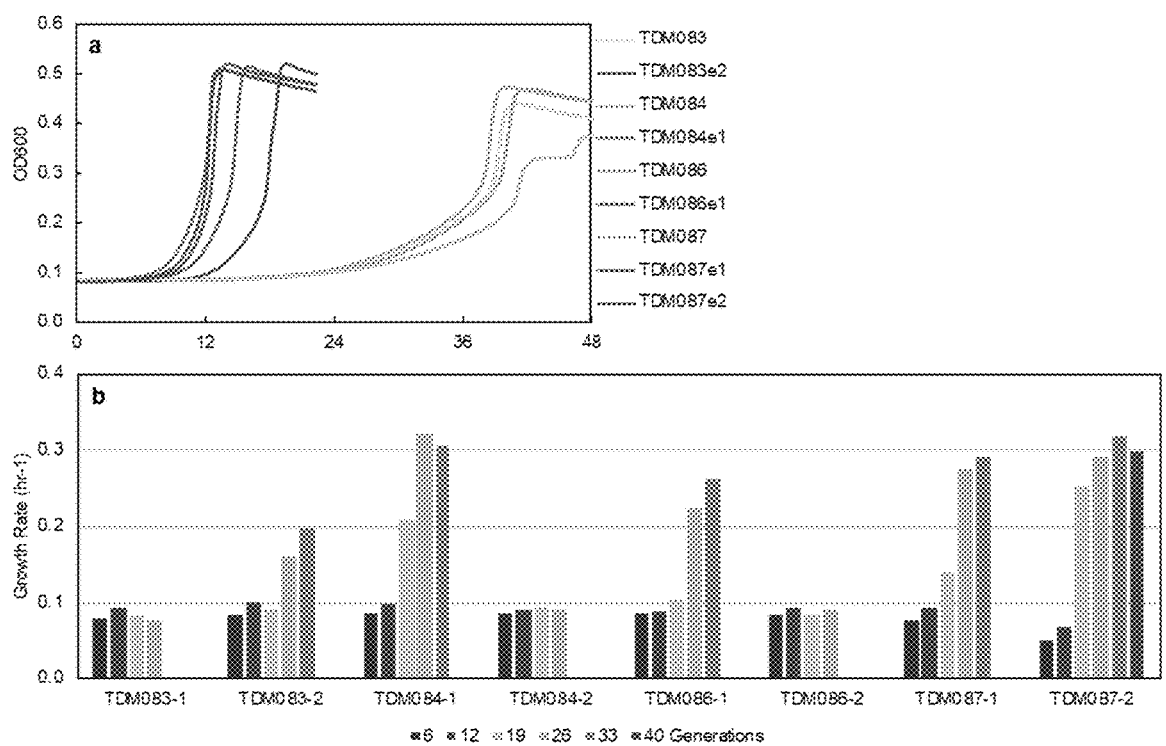
FIGS. 31a and 31b depict growth of TPA ALE evolved isolates in 10 mM TPA over up-to 40 generations of serial passaging.

While these strains could grow in TPA, the growth rate was slow as compared to PCA (FIG. 25b). To enhance the grow rate on TPA, we performed ALE by serially passaging duplicate cultures of the four strains which grew on TPA for 26-40 generations in minimal medium with 10 mM TPA as the sole carbon source (FIG. 31, FIG. 25c). Single colonies were isolated from end-point populations (TDM083e2, TDM084e1, TDM086e1, TDM087e1, and TDM087e2) and displayed 3.2 to 5.2-fold increases in growth rate on TPA which was similar to growth rate on PCA (FIG. 31, FIG. 25c). Whole-genome Illumina sequencing revealed three SNPs in the tpaK promoter in two of the fastest growing strains that converted the P549 promoter into the stronger Ptac promoter suggesting that TPA uptake was rate limiting to growth.

Figure 32:
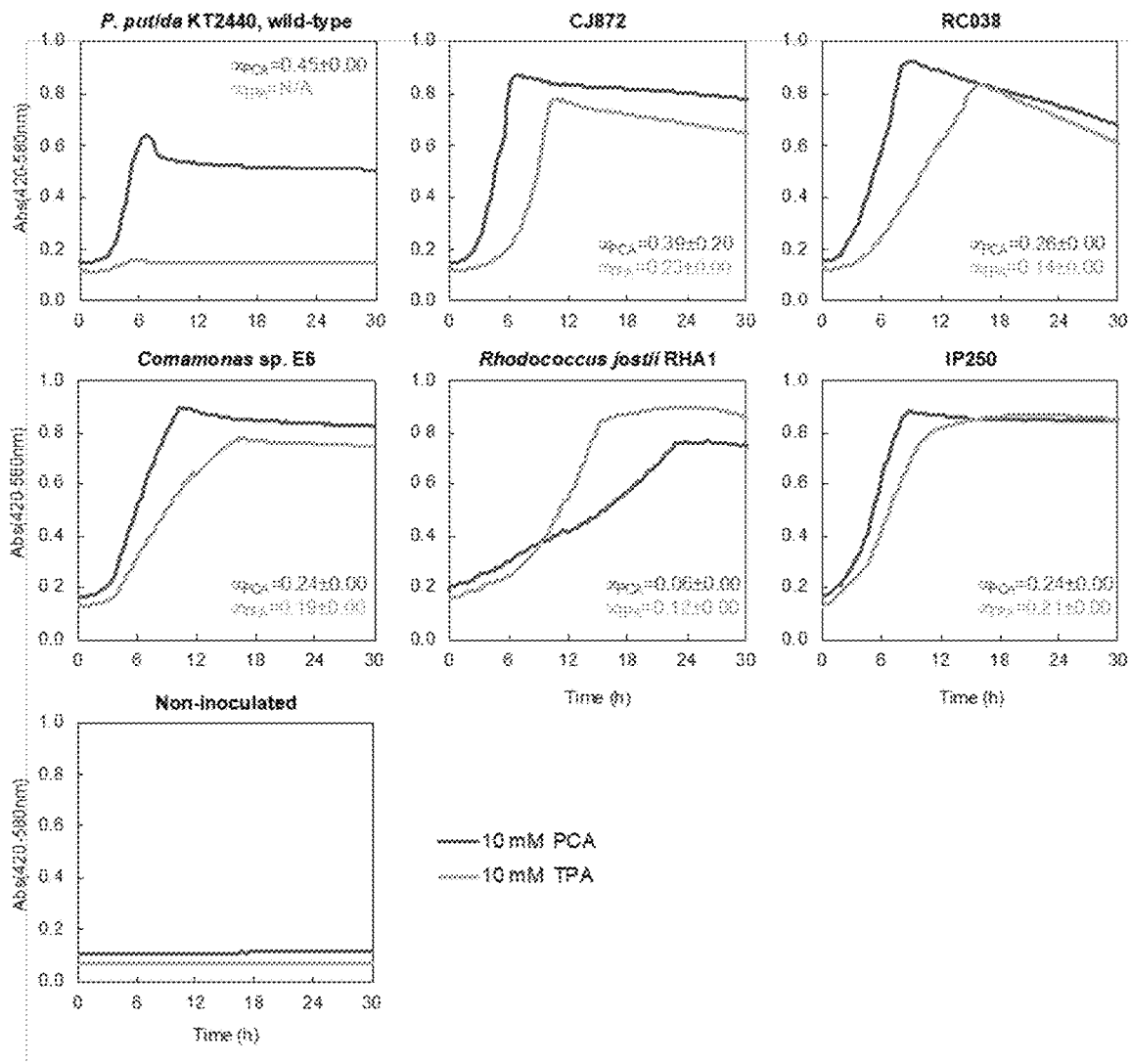
FIG. 32 depicts Growth of selected strains in 10 mM PCA or 10 mM TPA. Strain genotypes are provided in Table S3. Growth was monitored in a BioscreenC® as wideband absorbance every 15 min. Error bars represent the standard deviation among biological triplicates. Average growth rate for PCA and TPA is provided in the inset of each plot.

Using this information, we inserted the best TPA catabolic and transport pathway designs into the *P. putida* chromosome via homologous recombination. Ptac:tphA2IIA3IIBIIA1II replaced the inactive Type I DNA-restriction system genes hsdRM (PP_4740-PP_4741), and Ptac:tpaK was inserted into the intergenic region following fpvA (PP_4217). The resulting strain, TDM461, displayed a growth rate of 0.39±0.20 h-1 in 10 mM PCA and 0.23±0.00 h$^{-1}$ in 10 mM TPA (FIG. 32); this growth rate in TPA is slower than the evolved isolates but faster than *Comamonas* sp. E6 and *R. jostii* RHA1, the host organisms for the TPA catabolic and transport genes, respectively (FIG. 25d, FIG. 32). We also compared growth to IP250, a strain of *A. baylyi* our group previous engineered for TPA catabolism.37 IP250 had slightly slower growth rate (0.21 h$^{-1}$) as compared to TDM461 (FIG. 25d, FIG. 32). In confirmation of TPA catabolic activity, TDM461 utilized 45 mM TPA within 38 h of cultivation in shake flasks (FIG. 25e). Thus, while the growth improvement observed in ALE isolates was not fully recapitulated in TDM461, we considered the growth and utilization of TPA to be sufficient towards enabling BHET catabolism Stacked Expression of PETase and MHETase Enabled BHET Catabolism by *P. putida*

Figures 26A, 26B, 26C, 26D:
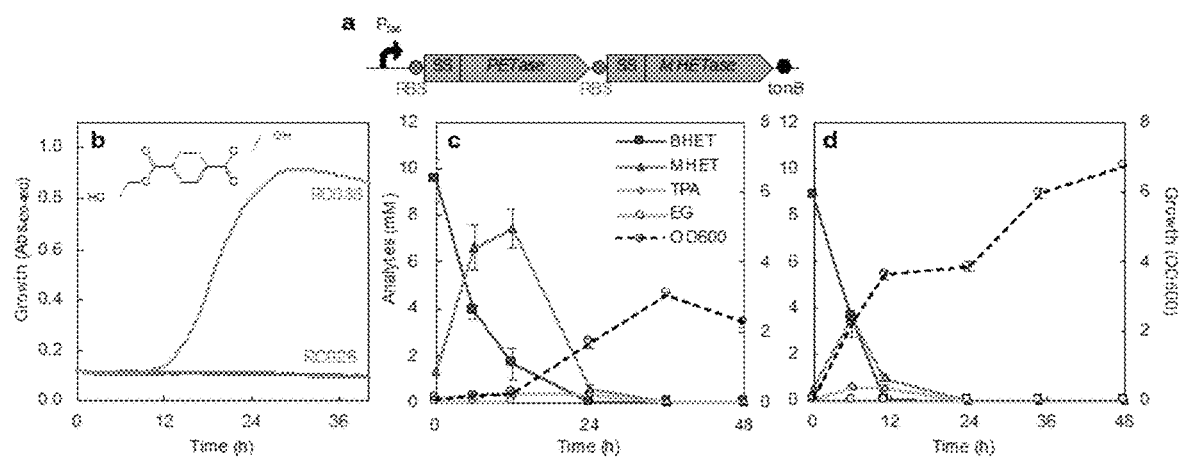
FIGS. 26a, 26b, 26c, and 26d depict Engineered catabolism of bis(2-hydroxyethyl)terephthalate (BHET) in P. putida.
Figure 33:
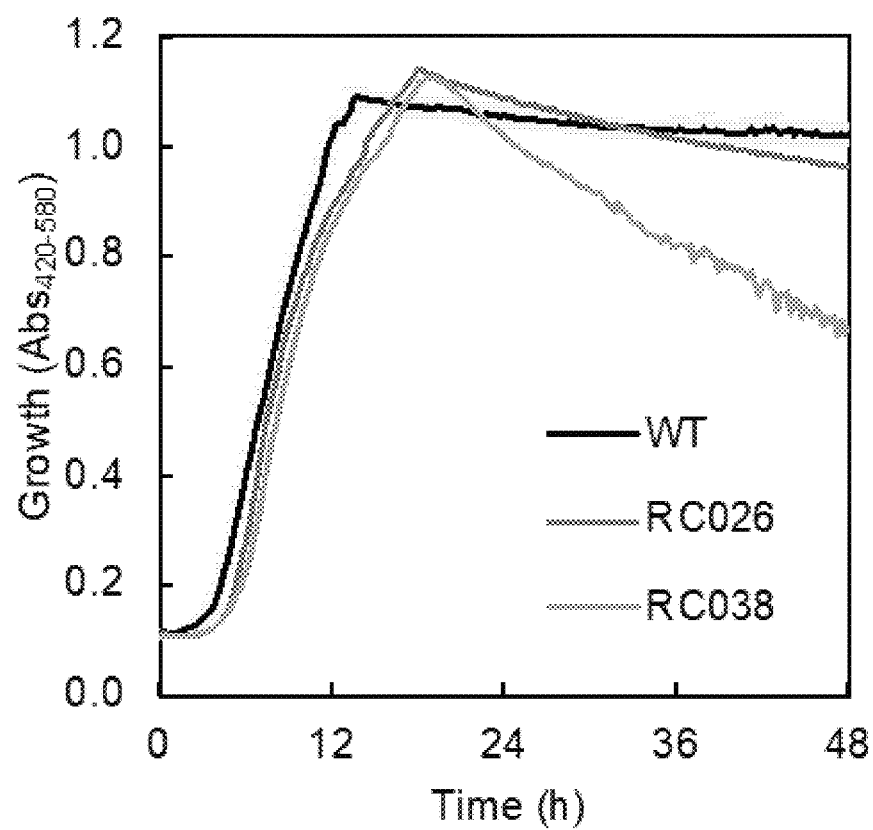
FIG. 33 depicts Engineered P. putida growth in 20 mM glucose. P. putida wild-type (WT), RC026 (P. putida $P_{tac}$: glcDEFG:PP_3749 ΔgclR ΔhsdM-hsdR::$P_{tac}$: tphA2$_{II}$A3$_{II}$B$_{II}$A1$_{II-E6}$ fpvA:$P_{tac}$:tpaK$_{RHA1}$), and RC038 (P. putida $P_{tac}$:glcDEFG:PP_3749 ΔgclR::PETase$_{Is}$:MHETase$_{Is}$ ΔhsdM-hsdR::$P_{tac}$:tphA2$_{II}$A3$_{II}$B$_{II}$A1$_{II-E6}$ fpvA:$P_{tac}$: tpaK$_{RHA1}$) growth in M9 minimal medium supplemented with 20 mM glucose. Growth was monitored in a BioscreenC® as wideband absorbance every 15 min. Error bars represent the standard deviation across biological triplicates.

Enzymatic conversion of BHET to TPA by *I. sakaiensis* occurs sequentially via two esterases, PETase and MHETase. To enable BHET conversion in *P. putida*, we first combined the TPA and EG genetic modifications described in the first two sections, generating strain RC026. For heterologous expression of PETase and MHETase, we maintained the *I. sakiensis* secretion signals, codon optimized each gene, designed synthetic RBSs, arranged a two-gene PETase:MHETase operon, drove expression via Ptac, and integrated this expression cassette into the chromosome at the gclR locus of RC026, generating strain RC038 (FIG. 26a, Table 9). RC038 had only a slightly decreased growth in 20 mM glucose as compared to RC026 (0.51±0.01 h-1 and 0.63±0.0 h-1, respectively) which was comparable to wild-type (0.53 h$^{-1}$, FIG. 33), indicating the accumulation of overexpressed enzymes did not incur an excessive metabolic burden. To assess microbial BHET mineralization, we solubilized BHET pellets in water via sonication (see Materials and Methods) and cultivated RC026 and RC038 in M9 minimal media supplemented with 10 mM BHET as the sole carbon source. RC026 did not grow, whereas RC038 grew with 12.2±1 h lag and 0.28 h-1 growth rate (FIG. 26b), which is 56% of the RC038 growth rate observed in 20 mM glucose (FIG. 33). This demonstrates PETase and MHETase expression is sufficient to enable catabolism of BHET in a RC026 background.

Figures 34A, 34B:
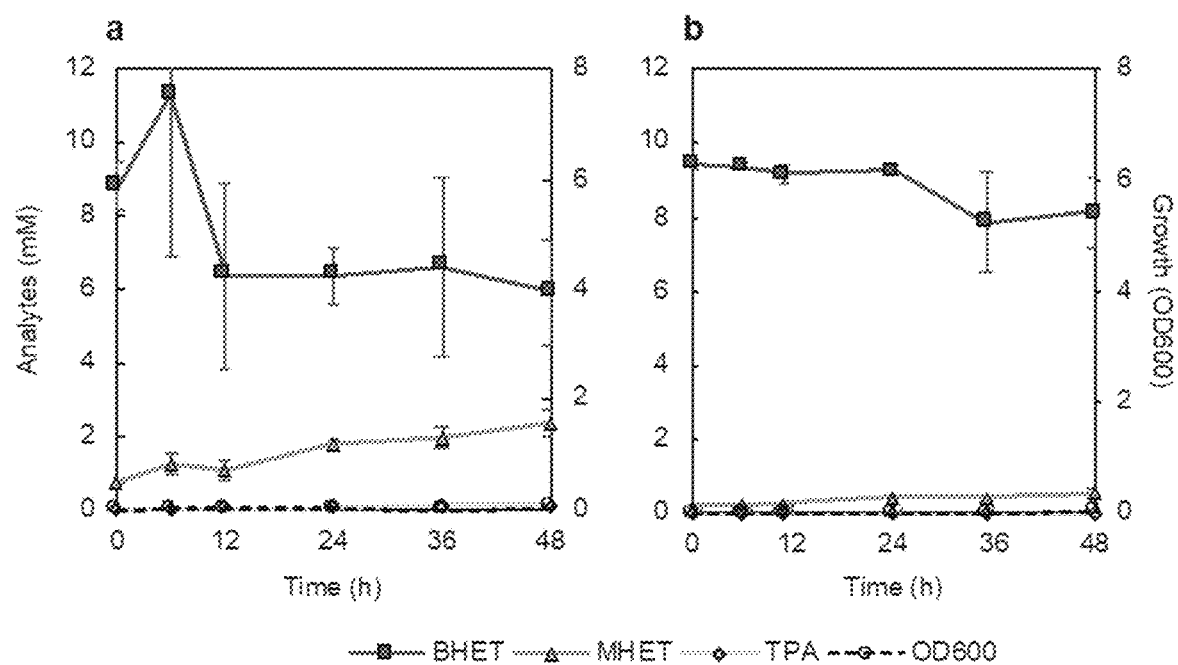
FIGS. 34a, 34b depict BHET and derived metabolite concentrations over time in non-inoculated controls. Analyte concentrations of shaken flasks with M9 minimal medium supplemented with (FIG. 34a) ~10 mM BHET or (FIG. 34b) ~10 mM BHET plus 20 mM glucose and feeding to 20 mM glucose every 24 h. Error bars represent the standard deviation among biological triplicates.

BHET, MHET, and TPA utilization dynamics were assessed in shaken flasks. Non-inoculated controls displayed 14±10% BHET degradation at 48 h of cultivation (FIG. 34), indicating a basal level of abiotic hydrolysis to MHET. Complete utilization of MHET and BHET was observed within 36 h by RC038 (FIG. 26c). Glucose supplementation increased the rate of BHET utilization (100% BHET utilization within 12 h) and reduced intermittent MHET accumulation (3.57 vs. 6.65 mM MHET at 6 h, FIG. 26d). These results suggest that MHETase activity is a bottleneck but can be largely alleviated by additional carbon/energy supplementation.

Bioconversion of BHET to β-Ketoadipate (βKA)

βKA can be polymerized into a nylon-6,6 analog with performance advantages, including a higher Tg and Tm, and a lower permeability.24 Notably, βKA is a metabolic intermediate of the βKA pathway, found in both bacterial and eukaryotic microrganisms—espeically soil-dwelling—for the degradataion of lignin-derived aromatics and environmental pollutants.41 In P. putida, ortho-cleavage of PCA by the PcaHG 3,4-dioxygenase (intradiol) generates a β-carboxymuconate moleucle which is converted to βKA by the PcaB, PcaC, and PcaD cycloisomerase, decarboxylase, and enol-lactonase activities, respectively (FIG. 23). To enable accumulation of βKA, we deleted pcaIJ, encoding 3-oxoadipate CoA-transferase, in RC038 to generate strain AW165 (FIG. 27a).

Figure 35:
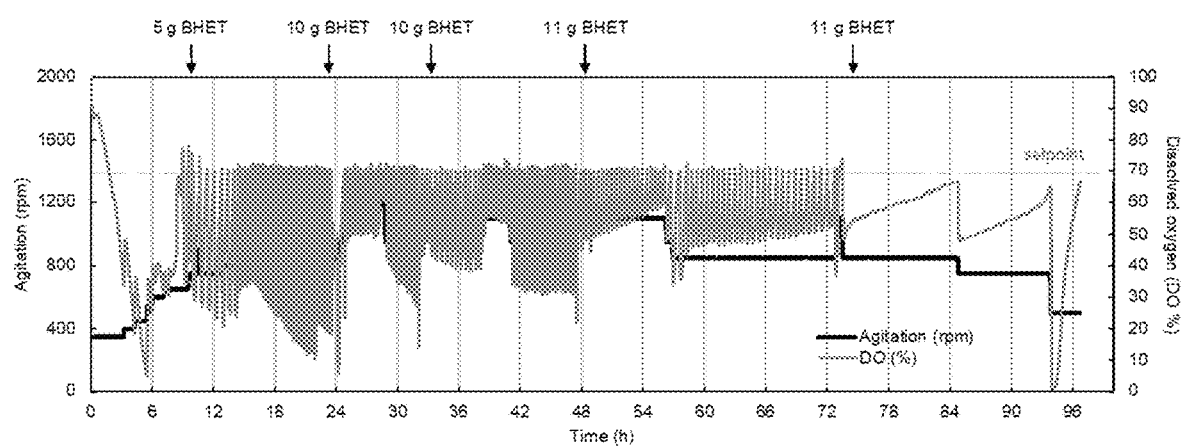
FIG. 35 depicts dissolved oxygen profiles from bioreactor. Agitation (rpm) was adjusted manually. Feed solution (100 g/L ammonium sulfate, 500 g/L glucose, 2% (v/v) antifoam) were pulsed to provide 2 mM glucose when the DO reached the 70% setpoint. BHET was added manually at the amounts and times indicated by black arrows.

Bioreactors were employed to evaluate βKA production from BHET as pH control is necessary when producing the βKA acid. P. putida also produces 2-ketogluconic acid (2KGA) in excess when glucose accumulates. To mitigate 2KGA accumulation, a dissolved oxygen (DO)-stat strategy was used to limit glucose accumulation. Pulses of 2 mM glucose from a 500 g/L glucose, 100 g/L (NH4)2SO4, and 2% (v/v) antifoam feed solution were fed when the DO reached 70% (FIG. 35). In this way, glucose was supplemented to support cellular growth and maintenance while maintaining low glucose concentration.

Figures 36A, 36B:
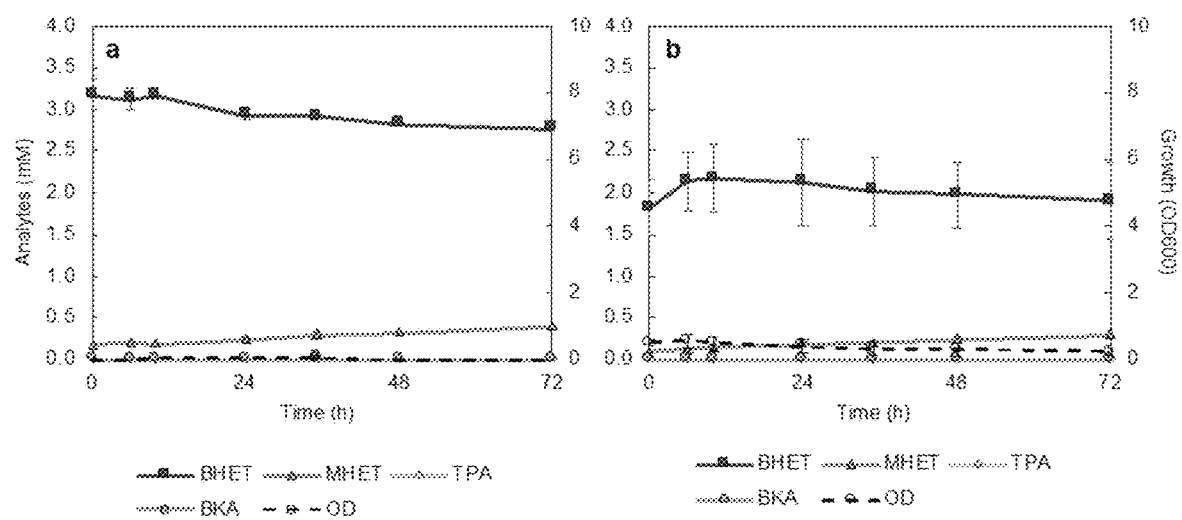
FIGS. 36a, 36b depict BHET, derived metabolites, and beta-ketoadipate concentrations over time from crude reaction product from glycolysis on PET. $OD_{600}$ and metabolite concentrations of non-inoculated cultivations in M9 minimal medium supplemented with 40 mM glucose and (FIG. 36a) 2.54 g/L pasteurized crude product solids plus 100 mM ampicillin, (FIG. 36b) 47% (v/v) crude product solution. Glucose was fed to 20 mM every 24 h. Error bars represent the standard deviation among biological triplicates.

BHET was fed separately from glucose via manual powder additions. We resorted to a solid feed because BHET solubility in water was so low it prohibited the preparation of a concentrated liquid stock. BHET power was ground, pasteurized, and added to the bioreactors via a port in the headplate (FIG. 27b). Solubilization of the power required several hours: white powder pelleted in samples such that accurrate quantification of BHET in solution was not achieved due to simultaneous solubilization and microbial conversion (FIG. 36). Thus, BHET addition was recorded based on the weight of the powder added in each feeding.

Figures 27A, 27B, 27C, 27D:
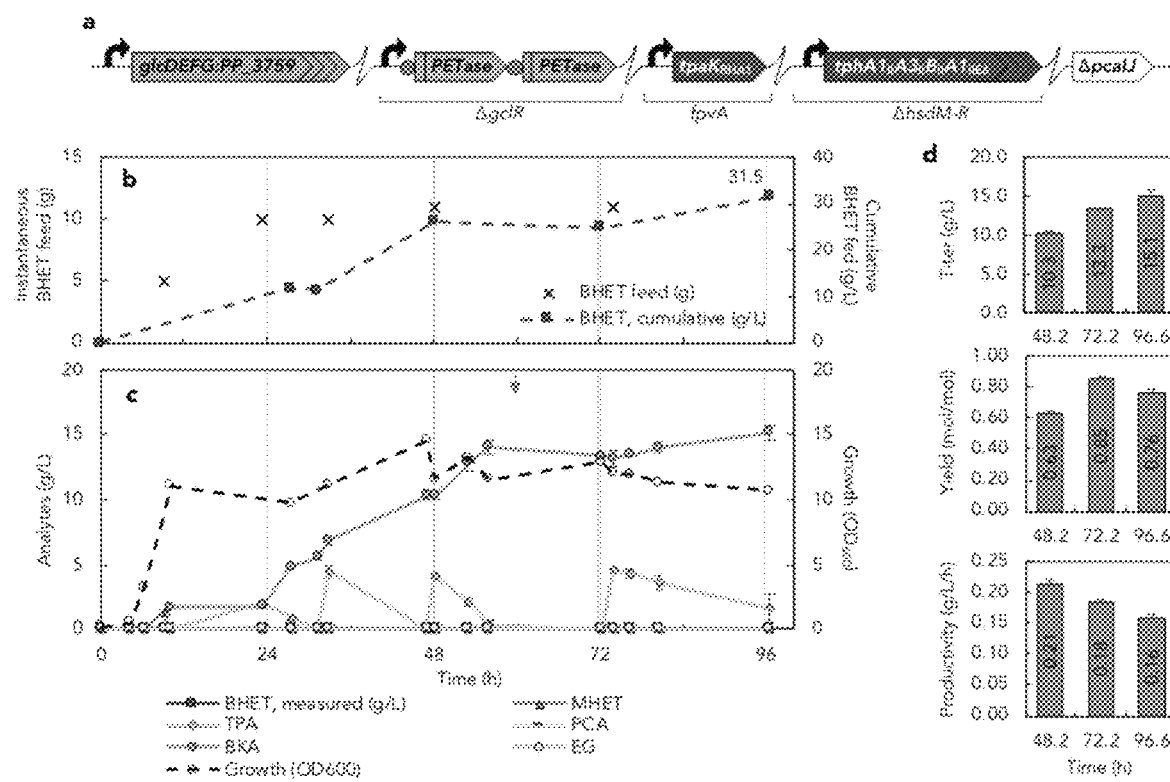
FIGS. 27a, 27b, 27c, 27d depict conversion of BHET to bKA in bioreactors.

BHET powder was added to each of three bioreactors in five discrete manual feedings totalling 47 g (FIG. 27a). Cell density remained relatively constant after BHET feeding had begun (OD600 of 11.1 and 10.7 at 10 and 96.6 h, respectively) despite frequent feedings of glucose (FIG. 36), suggesting a high energetic demand for cell maintenance and/or bioconversion. Of the BHET intermediates, only TPA accumulated (FIG. 27c,). This result is aligned with our shaken flask experimetns, and suggests TPA import or turnover is a bottleneck, especially at the latter timepoints.

At 96.6 h of cultivation, 31.5 g/L BHET had been converted to 15.1±0.6 g/L βKA at 76±3% molar yield and a productivity of 0.16±0.01 g βKA/L/h (FIG. 27d). The 76% molar yield, after accounting for resultial TPA, leaves a 10% error in the mol balance; we posit this error could be attributable to BHET powder which was not solubilized (e.g., physically stuck to the air-exposed baffles), trace impurities in the BHET powder, and instrumentation error. Yield and productivity fluctuated across the cultivation, reaching maximums of 0.85±0.02 mol/mol and 0.21 g/L/h at 72.2 and 48.2 h, respectively (FIG. 27c). This is the highest reported titer of an atom-efficient product from BHET—or any plastic-derived substrate—by an engineered microognamism, to our knowledge.

Biological Conversion of Chemically Depolymerized PET to βKA

Figure 37:
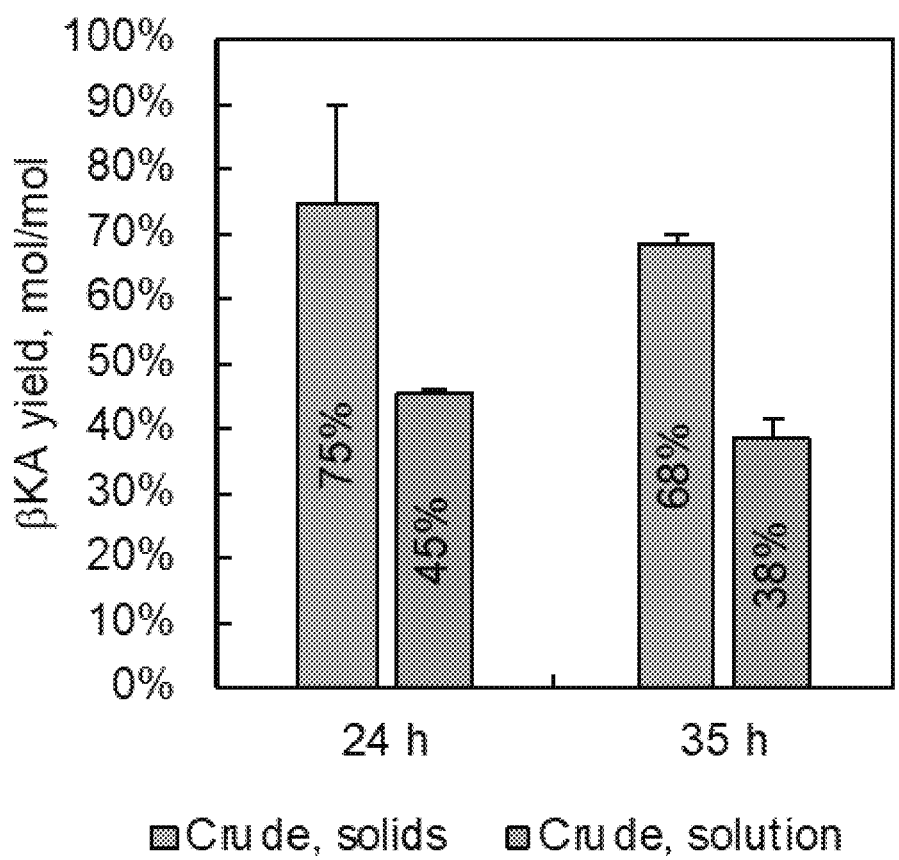
FIG. 37 depicts βKA yield from PET glycolysis crude solids or solution. Error bars represent the standard deviation among biological triplicates.

Lastly, we pursued a proof-of-concept for tandem chemical deconstruction of PET followed by biological upcycling to βKA. Goodfellows Biaxially Oriented PET flakes were deconstructed via transesterification where ethylene glycol was used as the diol and titanium butoxide was used as the catalyst (FIG. 23b), as previously described.30 [FIG. 29b, FIG. 36-37].

Figures 28A, 28B:
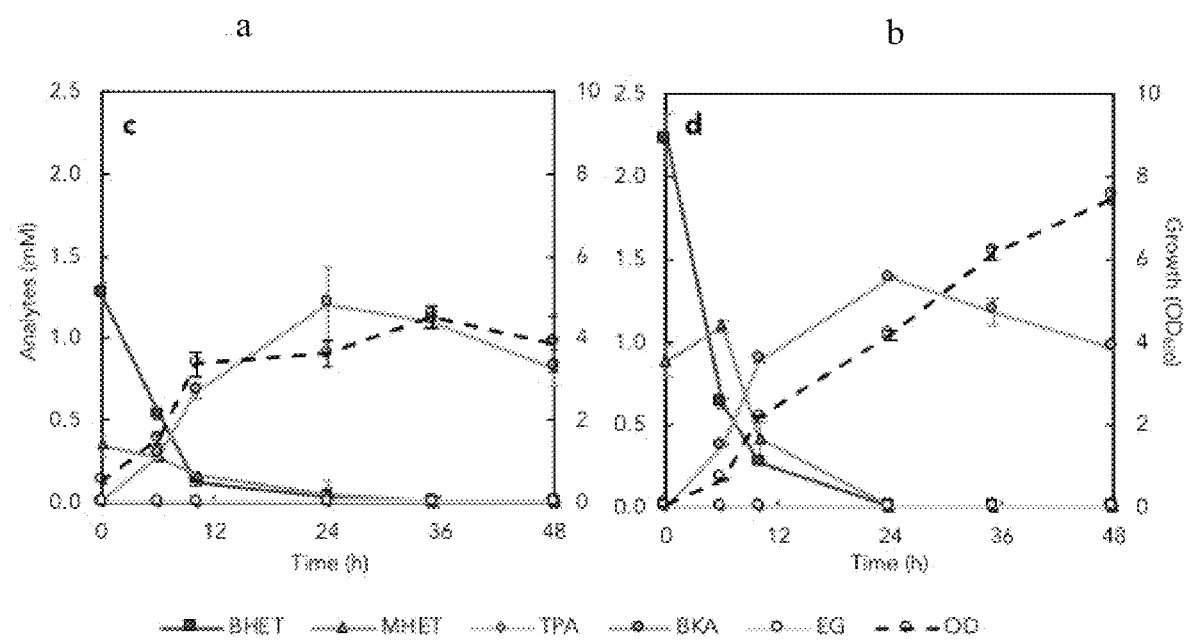
FIGS. 28a and 28b depict the conversion of PET to βKA via sequential chemical and biological processes, the preparation of PET for bioconversion, PET flakes were depolymerized via glycolysis; the reaction product was pasteurized, or suspended in water and filtered, prior to addition to microbial cultivations, and substrate characterization. Growth and metabolite concentrations of AW165 cultivations in M9 minimal medium supplemented with 40 mM glucose and (FIG. 28a) 2.54 g/L pasteurized crude product solids plus 50 μM ampicillin, (FIG. 28b) 47% (v/v) crude product solution. Glucose was fed to 20 mM every 24 h. Error bars represent the standard deviation among biological triplicates.
Figure 38:
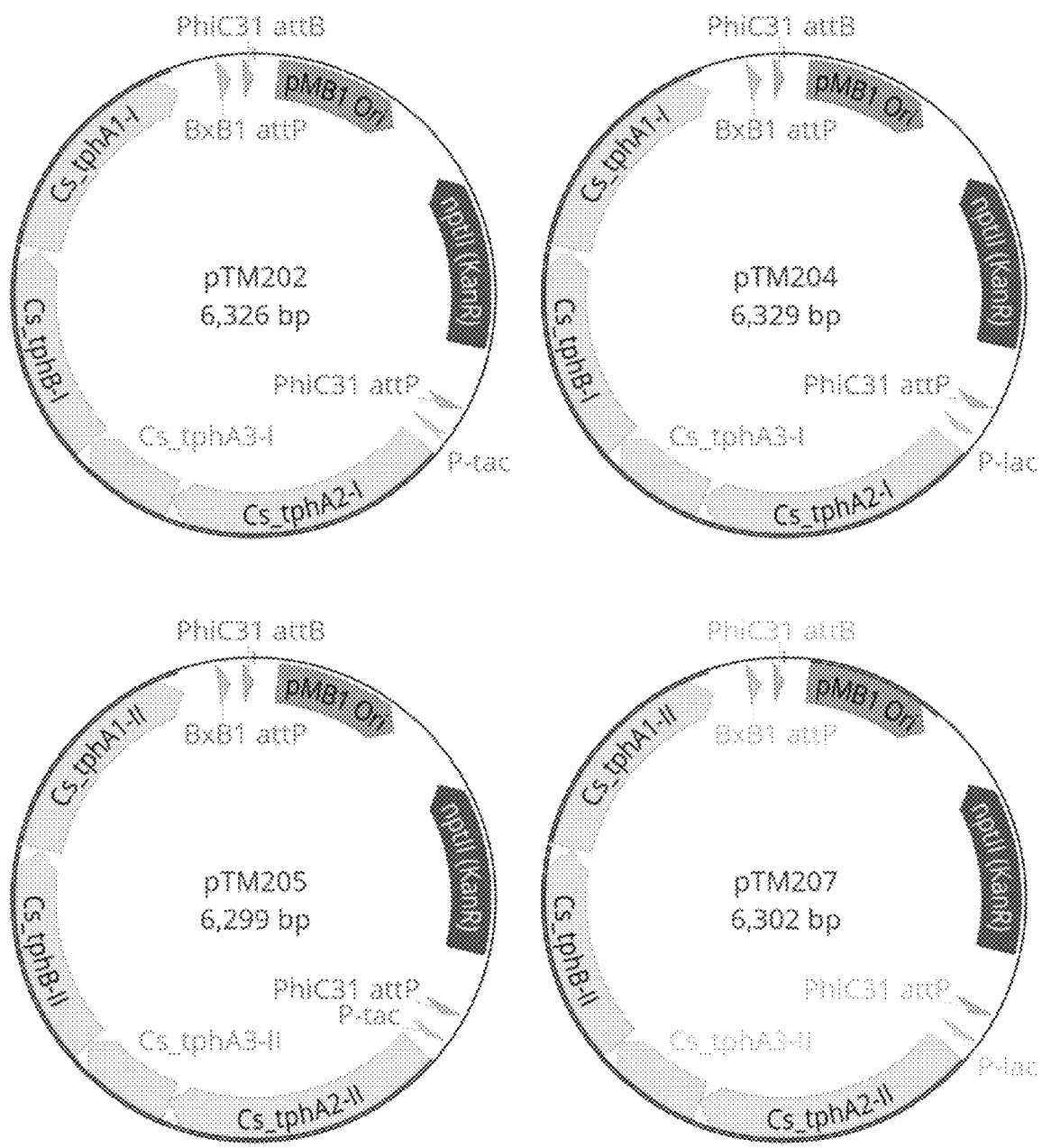
FIG. 38 depicts plasmid maps used in an embodiment disclosed herein.
Figure 39:
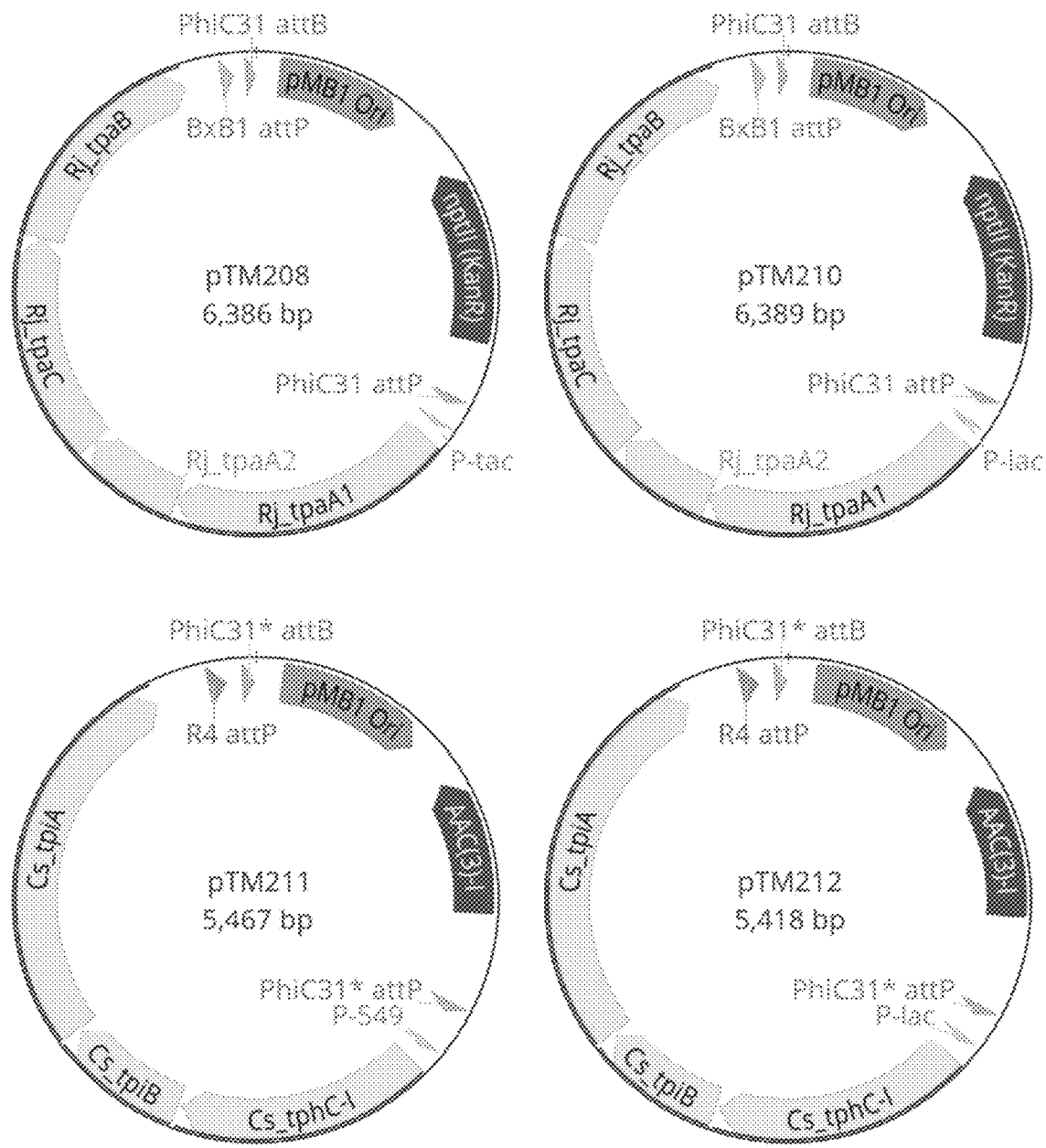
FIG. 39 depicts plasmid maps used in an embodiment disclosed herein.

We took a simple approach to prepare the crude reaction product for bioconversion (FIG. 28a). EG solvent was partially removed by filtration the wet solids were pasteurized, and added directly to microbial cultivations at a known weight. AW165 or non-inoculated controls were cultivated in M9 minimal medium supplemented with 40 mM glucose, 2.54 g/L pasteurized crude product, and 50 µM Ampicillin as a precaution against contamination via the crude product. BHET concentrations remained stable over time in non-inoculated controls; the presence of MHET at inoculation suggests pH- or temperature-induced BHET hydrolysis (FIG. 38, FIG. 28c). AW165 cellular growth, supported by glucose and EG, was not inhibited and 1.3 mM BHET plus 0.35 mM MHET present at inoculation was utilized within 36 (FIG. 28c,). At 24 h, 1.21±0.23 βKA was produced at 75±15% molar yield (FIG. 28b, FIG. 39). However, considering the substrate was provided as a solid which was partially insoluble, as with the bioreactor experiments, we could not be certain that the measured BHET at to captured the entirety of bioavailable substrate.

We also assessed bioconversion of a liquid suspension to enable accurate BHET quantification (no solids), avoid any heat-induced BHET degradation, and circumvent the need for antibiotic addition. The wet crude product was added to water, mixed at room temperature, and 0.2 µm filtered (FIG. 28a). AW165 reached a higher OD in cultivations with the crude product solution (48 h OD600=7.5±0.17) as opposed to the crude product directly (48 h OD600=3.9±0.67), suggesting toxic compounds from the glycolysis reaction were removed via filtration. Both BHET and MHET were present in the resulting solution which was free from solids such that quantification of analytes in the supernatant is representative (FIG. 28a), and concentrations were stable over time in non-inoculated controls (FIG. 38). After 24 h of cultivation, 3.11±0.06 mM of BHET and MHET were utilized, generating 1.39±0.01 mM βKA at a 45±1% molar yield (FIG. 28c, FIG. 39). Together, these results demonstrate conversion of PET-derived substrate to βKA is achievable with rudimentary preparation at the interface between chemical depolymerization and biological valorization.

Discussion

Here, we present a chromosomally engineered P. putida strain capable of catabolizing TPA and BHET—the latter of which is a product of chemocatalytic PET depolymerization—as sole carbon sources (FIG. 25-26). We further engineer this strain to convert BHET to βKA, a monomer which can be polymerized into a nylon-6,6 analog with performance-advantaged properties. We report a titer of 15.1 g/L at a 75% molar yield from commercial BHET (FIG. 27), and demonstrate proof-of-concept microbial βKA production directly from chemocatalytically depolymerized PET (FIG. 28). In sum, this work establishes a framework for an integrated chemical and biological approach to open-loop upcycling of waste PET plastics to performance-advantaged products.

Catabolism of TPA is central to bio-upcycling of PET, and has been reported to occur in diverse bacteria including *Nocardia*,43 *Bacillus*,44 *Rhodococcus, Comamonas,* and *Pseudomonas*. Narancic et al. recently engineered *P. putida* KT2440 for TPA catabolism by heterologous, plasmid-based expression of the *P. umsongensis* GO16 TPA gene cluster (including tpaK, tphA1BA3A2, and iclR). Comparing the genetic elements from *P. umsongensis* GO16 to those engineered here (from *Comomonas* sp. E6 and *R. jostii*) in *P. putida* KT2440, or comparing the engineered *P. putida* KT2440 reported here to *P. umsongensis* GO16 when it becomes publicly available, would be a useful endeavor towards optimizing TPA catabolism in *P. putida* KT2440. Enzyme engineering and/or directed evolution of TphA (for which no structure has been reported) and TphB (for which the *B. xenovorans* LB400 structure has been solved) may further serve to improve TPA utilization rates, ultimately working to improve chemical productivities from depolymerized PET streams. Looking ahead, post-consumer PET waste streams will contain additives (e.g., dyes and plasticizers) that may not be catabolized by *P. putida*. Characterization of these streams to identify the chemicals present and engineering metabolic pathways for utilization thereof (perhaps preceded by bioprospecting for discovery the associated pathways) will be necessary to avoid toxic accumulation during the bioconversion process.

Metabolic engineering holds the potential to considerably improve the microbial chassis presented here. At the BHET loadings we used (≤8 g/L instantaneous addition of solids), TPA accumulation was observed, suggesting that its catabolism is the rate-limiting step. As discussed above, efforts to improve TPA utilization should be pursued, for example, via adaptive laboratory evolution similar to our recent efforts with *P. putida* KT2440 and lignin-related aromatic compounds, to generate optimized TPA-catabolizing strains. Should the TPA bottleneck be overcome, improvement of BHET and MHET turnover may become necessary. Optimization of PETase/MHETase secretion and/or exploration of other PET hydrolases is of interest.

Bioprocess engineering will also be necessary to improve productivities and the feasibility of feeding solid plastic substrates. Adaptation of powder feeders to provide substrate in a timely (e.g., smaller feeds more routinely) and automated (e.g., supplied following a specified trigger) manner holds great potential. Examples of bioreactor configurations that accommodate solid feedings include fed-batch addition of pretreated corn stover via a mounted and automated powder feeder. Batch cultivations with solids—as is commonplace for wastewater treatment and the brewing of beer—is a promising alternative for substrates so long as chemical concentrations remain below the toxicity limit.

Biodegradation of plastics, defined as polymer depolymerization followed by subsequent monomer assimilation and mineralization, is considered as part of the solution to mitigate environmental (micro)plastic accumulation. Rigorous evaluation of the carbon fate from synthetic polymers is necessary to appropriately evaluate and classify the extent of microbial plastic degradation. A great example this comes from Yoshida et al., who reported *I. sakaiensis* performs PET depolymerization (via PETase and MHETase) followed by TPA assimilation and mineralization, constituting an example of microbial biodegradation of a fossil carbon-based plastic. Exogenous PETase and MHETase expression here enabled BHET catabolism (FIG. 26) but may also confer PET depolymerization capabilities, if effectual constituting a synthetic version of *I. sakaiensis*. Enzyme secretion, localization proximal to the substrate, and sustained extracellular activity is presumably paramount for microbial depolymerization of large polymeric substrates; similarities to cellulose degradation may exist and serve as inspiration for biotechnological development. Future work evaluating PET degradation of the herein reported *P. putida* against *I. sakaiensis* may reveal additional components important for improving microbial PET biodegradation.

Depolymerization of PET has been long studied via multiple approaches. Enzymatic hydrolysis, chemical hydrolysis, and thermolysis all produce the base monomers, TPA and EG. Conversely, chemical glycolysis (as conducted here) produces BHET when EG is used as the solvent, methanolysis produces dimethylterephthalate (DMT), and alcoholysis produces terephthalate diesters. Biological upcycling approaches, like that proposed here, are tunable to the deconstruction method and generated products. Indeed, the choice of deconstruction strategy will inform both the metabolic engineering approach and bioprocess needs, given the differences in catabolic enzyme needs. For example: both PETase and MHETase would be suitable for BHET (e.g., glycolysis product); MHETase, but not PETase, would be suitable for diester products of terephthalate (e.g., alcoholysis product); and only the TPA transport and catabolic genes would be necessary for TPA (e.g., hydrolysis and thermolysis products). Tandem deconstruction and upcycling approaches for PET will ultimately be determined by a combination of process feasibility and process modeling efforts to examine the economics and environmental impacts.58 We stress that the process option we demonstrated here is one of many that are conceptually feasible, and that judicious process analyses will be needed to compare among options, which we will examine in future efforts.

MATERIALS AND METHODS

Bacterial Strains and Cultivation

Chemically competent NEB® 5-alpha FIq *E. coli* (NEB Cat. C2992I) was cultivated at 37° C. shaking at 225 rpm in Miller's LB (Sigma Cat. L3522) supplemented with 50 µM kanamycin (Km). *Pseudomonas putida* KT2440 (ATCC® 47054, hereafter KT2440) and derived strains were cultivated in M9 minimal media (6.78 g/L Na2HPO4, 3 g/L KH2PO4, 0.5 g/L NaCl, 1 g/L NH4Cl, 2 mM MgSO4, 100 µM CaCl$_2$), and 18 µM FeSO4) at 30° C. shaking at 225 rpm. Glycerol stocks (20% (v/v)) were revived in LB, with the appropriate antibiotic for *E. coli* strains. M9 media was supplemented with carbon source(s), as indicated for each experiment. All chemicals were purchased from Sigma Aldrich unless specified otherwise. TPA stock solutions were made in water by gradually pH adjusting with NaOH; stocks were 0.2 µm filtered before use. Commercial BHET solution were made in water at a 2× concentration. Solubilization was achieved by sonicating the solution in a water bath for 1-1.5 h at 30° C. with periodic mixing; stocks were 0.2 µm filtered before use.

Plasmid Construction

Details on plasmid constructions can be found in Supplementary Tables 1-3. Briefly, Oligos were synthesized by Integrated DNA Technologies (IDT) unless otherwise specified. DNA amplification for plasmid constructions were performed via PCR with Q5® Hot Start High-Fidelity 2x Master Mix (NEB #M0494). Plasmid were assembled via Gibson Assembly or with NEB® NEBuilder HiFi DNA Assembly (NEB #E5520) and directly transformed into NEB® 5-alpha FIq E. coli for plasmid maintenance. Colony PCRs were performed with MyTaq™ Red Mix (Bioline #25043) and plasmid inserts were confirmed with Sanger Sequencing (GENEWIZ, Inc.). Plasmid maps for the TPA library pTM-series 202, 204, 205, 207, 208, 210, 211, and 212) are provided in FIG. S12.

Strain Construction

For construction of the TPA-catabolizing library, a modified strain of *P. putida* that contains several serine recombinase attB attachment sites at neutral loci served as the host (strain AG3454). AG3454 was simultaneously transformed with four plasmids, including a catabolic plasmid and a transport plasmid, which had different attP attachment sites corresponding to separate attB loci, and two plasmids that independently and transiently expressed the serine recombinases required for integration. Transformants were selected on LB plates (1.5% agar) containing both antibiotics for the catabolic plasmid (kanamycin, 50 μg/mL) and the transport plasmid (gentamicin, 30 μg/mL). Initial recombination into the chromosome was selected on LB plates containing 50 μg/mL kanamycin, and the second crossover event was counter-selected on YT+25% sucrose plates (10 g/L yeast extract, 20 g/L tryptone, 250 g/L sucrose, 18 g/L agar), and removal of plasmid backbone was confirmed by PCR and an inability to grow on LB plates with 50 μg/mL kanamycin, as previously described. All other chromosomal integrations and deletions in KT2440 were performed via the antibiotic/sacB method, as previously described. Correct integrations were confirmed by cPCR. Details on individual strain constructions can be found in Tables 8-10.

Adaptive Laboratory Evolution (ALE)

ALE was performed by serially passaging isolates in MME minimal medium (Table S5) with 10 mM TPA as the sole carbon source. Duplicate cultures of each TPA-utilizing isolate were started from individual colonies and continually passaged in fresh media upon reaching stationary phase. To evaluate the isolates, all isolates of the combinatorial library were tested for the ability to utilize TPA for growth. Overnight cultures were grown from individual colonies picked into LB with 50 μg/mL kanamycin and 30 μg/mL gentamicin. Cultures were washed once in MME minimal media (Table 9), and then inoculated (2% inoculum) into MME with either 10 mM PCA or 10 mM TPA.

Determination of TPA Consumption Rate

The rate of TPA consumption was measured by sampling of batch cultures grown in shake flasks at 30° C. A seed culture of *P. putida* TDM461 was grown overnight in MME with 50 mM TPA and was used to inoculate duplicate flasks of 25 mL Modified MME with 50 mM TPA at 10% inoculum. Trial experiments indicated growth was limited in standard MME with 50 mM TPA, and thus the following supplementations were made. Modified MME is based on the MME recipe from Supplemental Table 2, but with 2x NH4Cl (1.0 g/L), 2x Trace Minerals (2 mL/L of 1000x solution), and 20 mM Tris(hydroxymethyl)aminomethane (Tris base). Periodically 1 mL samples were withdrawn, cells were pelleted by centrifugation, and the supernatant was stored at −20° C. The concentration of TPA in culture supernatants was measured on an Agilent 1260 Infinity II HPLC equipped with a Bio-Rad Fast Acid Analysis HPLC column. Prior to analysis, samples were thawed, acidified to a final concentration of 5 mM $H_2SO_4$ to match the mobile phase, and passed through a 0.45 μm filter. A peak for TPA eluted at around 21.5 min and was detected by the Agilent 1260 Infinity II Variable Wavelength Detector at 230 nm. TPA was completely consumed in less than 38 hours, and the maximum consumption rate was reached as the culture reached stationary phase (around 21 hours) and approximately 86% of TPA had been consumed.

Microtiter Plate Cultivations

Precultures were inoculated from glycerol stocks and grown overnight (12-16 h) in LB at 30° C. and 225 rpm, washed in 1xM9 salts, and inoculated into M9 minimal media supplemented with the carbon source(s) specified for each experiment. Tecan experiments were performed in an Infinite® F500 at 30° C. and OD600 was measured at 15 min. intervals. BioscreenC® (Growth Curves, USA) experiments were performed in honeycomb 100-well plates at 30° C., maximum shaking, and wideband absorbance (420-580 nm) was measured every 15 min.

Shaken Flask Cultivations with Model Substrate

Precultures were prepared and washed, inoculated at an OD600 of 0.1 in 30 mL of M9 minimal medium supplemented with the carbon source(s) as specified in 125 baffled metal-capped Erlenmeyer flasks, and cultivated at 30° C. with shaking at 225 rpm (0.75"). Growth was measured as absorbance at 600 nm (OD600). Samples were taken for metabolite analysis by removing 1 mL of culture, centrifuging at >18,000 g for 2 min, 0.2 μm syringe filtering the supernatant into glass vials, capping, and storing at −20° C. until analysis. Raw data for growth and metabolite abundance measurements for all shaken flask experiments are provided in.

Bioreactor Cultivations

Applikon In-Control 2.5 L bioreactors were sterilized and 1.2 L of M9 minimal medium (13.6 g/L NaHPO4, 6 g/L KH2PO4, 1 g/L NaCl, 2 g/L (NH4)2SO4, 2 mM MgSO4-7H2O, 0.1 mM $CaCl_2$)-2H2O, 5 mg/L FeSO4-7H2O, and 0.2 mL/L Antifoam 204) with 2.7 g/L glucose was added to each reactor. Triplicate AW165 seed cultures were prepared by reviving glycerol stocks in 50 mL LB and cultivating overnight at 30° C. and 225 rpm. The cells were washed in M9 minimal medium salts and inoculated into three bioreactors at an OD600 of 0.2 (~5 mL washed seed culture per reactor).

A DO-stat glucose fed-batch with manual BHET feeding was employed. The feeding solution contained 100 g/L ammonium sulfate, 500 g/L glucose, 2% (v/v) antifoam 206. The feeding solution was aliquoted into three 300 mL bottles (one for each reactor) and pH adjusted with 350 μL of 4N NaOH per bottle. When the DO reached 70%, the feeding solution was pumped to provide 2 mM glucose. Agitation was manually adjusted to maintain frequent DO oscillations. Following 4 h of glucose batch phase, 1 mM 4HBA was added and the reactors were run for an additional 3.5 h prior to BHET addition. The poor solubility of BHET in water prevented preparation of concentrated stocks, so solid BHET feeding was employed. BHET flakes (Sigma Cat. 465151) were ground into small particles, heated at 70° C.

for 1 h to pasteurize, weighed under aseptic conditions, and added to reactor via a port in the headplate at the times and amounts specified. To mitigate contamination via the open port during solid feeding, 50 µM ampicillin was added. The fermentations were harvested when DO oscillations became infrequent.

PET Deconstruction Via Glycolization

PET deconstruction via glycolysis was performed as previously described.30 Briefly, Goodfellows Biaxially Oriented PET flakes (Cat. #) were . . . . Following the reaction, the crude product was filtered for 2 h to remove excess EG. Characterization details Shaken Flask Cultivations with Crude PET Reaction Product For microbial cultivations in PET-derived BHET, solid and liquid feeds were prepared. For solid addition, the reaction product was filtered for 2 h to remove some EG, weighed, heated at 70° C. for 1 h to pasteurize, and added to media along with ampicillin (50 µM) to prevent microbial contamination. For liquid addition, the reaction product was weighed, added to deionized water, stirred at room temperature for 1 h, and 0.2 µm vacuum filtered. Preculture preparation and sampling was performed as in described in Shaken flask cultivation.

TABLE 8

| Plasmids | | |
|---|---|---|
| Plasmid | Utility | Construction details |
| pK18mobsacB | Suicide vector for kanamycin/sucrose selection and counterslection-mediated gene replacements in *P. putida* KT2440; Confers kanamycin resistance | ATCC ® 87097 ™, as described in Schäfer et al. (1994).[1] |
| pLJ062 | pK18mobsacB-based vector for deletion of gclR from the KT2440 genome and derived strains | As described in Li et al. (2019).[2] Alternatively: The 5' homology region (1060 bp) was amplified from *P. putida* KT2440 genomic DNA with primers oLJ426 (Fwd), and oLJ427 (Rev), and 3' homology region (1060 bp) was amplified with oLJ428 (Fwd) and oLJ429 (Rev). These products were assembled into pK18sB digested with EcoRI and HindIII. |
| pRC001 | pK18mobsacB-based vector for insertion of the $P_{tac}$ promoter in front of the gcl operon in the chromosome of KT2440 and derived strains | The pMFL191 backbone (see Franden et al. 2018[3, 4]) was amplified with oCJ915 and oCJ916 (5,107 bp) where the primers contain the $P_{tac}$ promoter sequence. The product was DpnI digested, purified, and transformed into NEB F'Iq *E. coli*. cPCR confirmation with oCJ546 and oCJ547 (2,360 bp) was followed by Sanger sequencing (oCJ906, oCJ907, oCJ913, oCJ914, oCJ546, oCJ547). |
| pLJ039 | Template for construction of pRC001 | A gBlock containing codon optimized PETase and MHETase (gBlock_PETase_MHETase, Table S2) was synthesized). The DNA fragments were amplified from gBlock_PETase_MHETase with oLJ189 and oLJ190 and assembled into pBLT-2 digested with XbaI and EcoRV. (Construction detail are available at notebook PET upcycling #1, Book 6752, page 023 |
| pRC001 | Template for construction of pRC004 | The PETase:MHETase gene cassette was amplified from pLJ039 with oCJ929 and oCJ930 (5,326 bp), DpnI digested, and transformed into NEB F'Iq *E. coli*. cPCR confirmation with oCJ054 and oLJ484 (378 bp) was followed by Sanger sequencing with oCJ531, oCJ920, oCJ921, oCJ922, and oCJ934. |
| pRC004 | pK18mobsacB-based vector for insertion of the PETase and MHETase genes from *I. sakiensis* into the chromosome of KT2440 with simultaneous gclR deletion and derived strains | The PETase:MHETase gene cassette was amplified from pRC001 with oCJ935 and oCJ936 (3,003 bp). The plasmid backbone with gclR homology regions was amplified from pLJ062 with oCJ937 and oCJ098 (5,048 bp). The reaction products were purified and assembled via HiFi Assembly and transformed into NEB F'Iq *E. coli*. cPCR confirmation with oCJ546 and oCJ547 (5,232 bp) was followed by Sanger sequencing (oCJ546, oCJ547, oCJ920, oCJ921, oCJ922, oCJ928, oCJ947, oCJ948). |
| pCJ059 | pK18mobsacB-based vector for deletion of pcaIJ from the chromosome of KT2440 and derived strains | As described in Johnson et al. (2019).[5] |
| pGW31 | BxB1 serine recombinase expression; apramycin resistance (AAC(3)-IV). | |
| pGW39 | R4 serine recombinase expression; apramycin resistance (AAC(3)-IV). | |

TABLE 8-continued

| Plasmids | | |
|---|---|---|
| Plasmid | Utility | Construction details |
| pTM202 | Site-specific integrating plasmid; BxB1 attP; kanamycin resistance (nptII). Ptac-tphA2$_I$A3$_I$B$_I$A1$_I$ (*Comamonas* sp. E6) | |
| pTM204 | Site-specific integrating plasmid; BxB1 attP; kanamycin resistance (nptII). Plac-tphA2$_I$A3$_I$B$_I$A1$_I$ (*Comamonas* sp. E6) | |
| pTM205 | Site-specific integrating plasmid; BxB1 attP; kanamycin resistance (nptII). Ptac-tphA2$_{II}$A3$_{II}$B$_{II}$A1$_{II}$ (*Comamonas* sp. E6) | |
| pTM207 | Site-specific integrating plasmid; BxB1 attP; kanamycin resistance (nptII). Plac-tphA2$_{II}$A3$_{II}$B$_{II}$A1$_{II}$ (*Comamonas* sp. E6) | |
| pTM208 | Site-specific integrating plasmid; BxB1 attP; kanamycin resistance (nptII). Ptac-tpaA1A2CB (*Rhodococcus jostii* RHA1) | |
| pTM210 | Site-specific integrating plasmid; BxB1 attP; kanamycin resistance (nptII). Plac-tpaA1A2CB (*Rhodococcus jostii* RHA1) | |
| pTM211 | Site-specific integrating plasmid; R4 attP; gentamicin resistance (AAC(3)-I). P549-tphC$_I$-tpiBA (*Comamonas* sp. E6) | |
| pTM212 | Site-specific integrating plasmid; R4 attP; gentamicin resistance (AAC(3)-I). Plac-tphC$_I$-tpiBA (*Comamonas* sp. E6) | |
| pTM214 | Site-specific integrating plasmid; R4 attP; gentamicin resistance (AAC(3)-I). P549-tpaK (*Rhodococcus jostii* RHA1) | |
| pTM215 | Site-specific integrating plasmid; R4 attP; gentamicin resistance (AAC(3)-I). Plac-tpaK (*Rhodococcus jostii* RHA1) | |
| pTM219 | pK18mobsacB based plasmid; nptII; sacB. Ptac-tpaK flanked by homology arms for insertion between PP_4717-PP_4718 | |
| pTM232 | pK18mobsacB based plasmid; nptII; sacB. Ptac-tphA2$_{II}$A3$_{II}$BuA1$_{II}$ flanked by homology arms for replacement of PP_4740-PP_4741 | |

TABLE 9

| Oligonucleotides | | | |
|---|---|---|---|
| SEQ ID NO: | Oligo | Sequence (5' → 3') | Desc. |
| SEQ ID NO: 34 | oCJ366 | CGATTGCGCCATGAACAG | cPCR confirmation of genomic pcalJ deletion |
| SEQ ID NO: 35 | oCJ367 | AGGCTGCCGAGTATCATG | |
| SEQ ID NO: 36 | oCJ911 | TTGAATTCGAGCTGTTGACAATTAATCATC | |
| SEQ ID NO: 37 | oCJ912 | GACCTCGAGGATACGGTTG | cPCR confirmation of genomic P$_{tac}$ integration prior to glcDEFG:PP_3749 |
| SEQ ID NO: 38 | oLJ426 | AAACAGCTATGACATGATTACGAATTCGAGCTC GGTACCCCGTGGTGCTGGACTACAAGG | PCR amplification of the upstream homology arm for deletion of gcIR from *P. putida* gDNA |
| SEQ ID NO: 39 | oLJ427 | TCTTCGTGCCTCGAGAGCCCTCGTTTGCCTGC GTGATCG | |
| SEQ ID NO: 40 | oLJ428 | TCGATCACGCAGGCAAACGAGGGCTCTCGAG GCACG | PCR amplification of the downstream homology arm for deletion of gcIR from *P. putida* gDNA |
| SEQ ID NO: 41 | oLJ429 | TGTAAAACGACGGCCAGTGCCAAGCTTGCATG CCTGCAGGCGGCATCGACATCACCCC | |
| SEQ ID NO: 42 | oLJ430 | CCTTCTGCCCCACCTCCA | cPCR confirmation of genomic gcIR deletion |
| SEQ ID NO: 43 | oLJ431 | CCCCCGCAGCACTCT | |
| SEQ ID NO: 44 | oCJ546 | ATAGTCCTGTCGGGTTTC | Sequencing and cPCR reactions of inserts into pK18mobsacB as specified in Table S1. |
| SEQ ID NO: 45 | oCJ547 | CCATCTTGTTCAATCATGCG | |

TABLE 9-continued

Oligonucleotides

| SEQ ID NO: | Oligo | Sequence (5' → 3') | Desc. |
|---|---|---|---|
| SEQ ID NO: 46 | oCJ915 | <u>AATTAATCATCGGCTCGTATAATGTGTGGAATT GTGAGCGGATAACAATTTCACACCGGAGGGAG</u>TTTTGCGATGAATATCCTGTACGACGAACGCGT CG | PCR amplification of the pMFL191 (see Franden et al. 2018[3, 4]) backbone. The underlined regions contains the P$_{lac}$ promoter sequence. |
| SEQ ID NO: 47 | oCJ916 | CCACACATTATACGAGCCGATGATTAATTGTCA<u>ACAGCTCGAATTCAAAAAACCGCACCTGGGTG CG</u> | |
| SEQ ID NO: 48 | oLJ189 | GGAATTGTGAGCGGATAACAATTTCACACTTCA TCAAGTCAAAACACTATATAGGAACGAAACCAT GAACTTCCC | PCR amplification of gBlock_PETase_MHETase |
| SEQ ID NO: 49 | oLJ190 | CGCTGGAGTCTGAGGCTCGTCCTGAATGATCG GAGGCGCGGCGCAGGC | |
| SEQ ID NO: 50 | oCJ906 | CTTCGCCAACAACAACAAAAACCG | Sanger sequencing of pRC001 |
| SEQ ID NO: 51 | oCJ907 | CCTGCGGGTTGACCTCGA | |
| SEQ ID NO: 52 | oCJ913 | GTAGCACCCGCCTGCC | |
| SEQ ID NO: 53 | oCJ912 | GACCTCGAGGATACGGTTG | |
| SEQ ID NO: 54 | oCJ929 | GCTTGACAATTAATCATCGGCTCGTATAATGTG TGGAATTGTGAGCGGATAAC | PCR amplification of pLJ039 |
| SEQ ID NO: 55 | oCJ930 | TTATACGAGCCGATGATTAATTGTCAAGCCTGG GGTGCCTAATGCAAATC | |
| SEQ ID NO: 56 | oCJ054 | ATCGGCTCGTATAATGTGTGG | cPCR confirmation of pRC001 and pRC002 construction |
| SEQ ID NO: 57 | oLJ484 | GGCCCCACCACTTGATCGA | |
| SEQ ID NO: 58 | oCJ935 | CCCCTCGATCACGCAGGCAAACGAAGTCAAAA GCCTCCGGTC | PCR amplification of the PETase:MHETase gene insert from pRC002 |
| SEQ ID NO: 59 | oCJ936 | CTTCGTGCCTCGAGAGCCCAAAACTAAAGCGC CACAAGGG | |
| SEQ ID NO: 60 | oCJ920 | GCAAAGTGGACACCGCTC | Sanger sequencing of the insert DNA sequence for pRC004 |
| SEQ ID NO: 61 | oCJ921 | GTAGTTGAAGTGGCCGCATG | |
| SEQ ID NO: 62 | oCJ922 | CATCCTCGGTACTTGCGATG | |
| SEQ ID NO: 63 | oCJ947 | GTTCCTCGTCCCAGGCATG | |
| SEQ ID NO: 64 | oCJ948 | GCCCCTACGCTGGATCTTGC | |
| SEQ ID NO: 65 | oCJ928 | GAAGGCGAAGGCGACAC | |
| SEQ ID NO: 66 | gBlock_ PETase_ MHETase | GAGCTGttgacaattaatcatcggctcgtataatg TGTGGA<u>ATTGTGAGCGGATAACAATTTCACACTCA TCAAGTCAAAACACTATATAGGAACGAAACC</u>atga acttccctcgcgcgtcgcgcctgatgcaggcggcg gtcctcggtggtctgatggcagtcagcgccgcggc caccgctcagaccaacccatacgcccgcggcccaa accctaccgcggcagcctggaagcctctgccggc ccattcaccgtgcgcagcttcaccgtcagtcgccc gtcgggctatggtgccggcaccgtctactacccaa ccaacgctggcgaccgtcggcgccatcgcaatc gtgccgggctataccgcccgccagtcctcgatcaa gtggtggggccacgtctggcctcccacggcttcg ttgttatcaccatcgacaccaactcgaccctggac cagccgtcctcccgctcgagccagcagatggctgc tctgcgccaggtagcttcgctgaacggcaccagct ctagcccaatctacggcaaagtggacaccgctcgc atgggcgtgatgggttggtccatgggcggtggtgg ttccctgatctccgctgctaataatccttccctga aggccgccgccccgcaggcccatgggactcctcg accaacttctcgagcgtgaccgtgccgacctgat cttcgcttgcgaaaacgacagcatcgctccggtga actctccgcgctgcctatctacgactccatgagc cgcaacgccaagcaattcctggaaatcaacggcgg ttcccactcctgcgctaactcgggcaactcgaacc aagccctgatcggcaagaagggcgtagcatggatg aagcgtttcatggataacgacaccgttactcgac cttcgcctgcgaaaacccgaactctactcgcgtca gcgacttccgcactgcgaactgcagc<u>TAACAAGGA TTACATATAAGGGTATATCAAATGCA</u>GACCACCGT CACCACTATGCTGCTGGCATCGGTCGCCCTGGCCG CCTGCGCAGGCGGCGGCAGCACCCCGCTGCCG CTGCCGCAGCAACAGCCGCCACAGCAGGAGC CGCCGCCTCCTCCAGTCCCGCTGGCTTCCCGT GCTGCGTGTGAGGGCCCTGAAGGACGGCAACG GGGACATGGTTTGGCCGAACGCCGCCACCGT | The PETase and MHETase from *Ideonella sakaiensis* strain 201-F6 were codon optimized for expression in *P. putida* KT2440 using the OPTIMIZER software (http://genomes.urv.es/OPTIMI ZER/) random guided method. PETase is shown in lowercase blue; MHETase is shown in UPPERCASE PURPLE Synthetic RBSs (GREEN UNDERLINE) were designed using the Salis Lab RBS Calculator v2.1 (https://salis.psu.edu/software/) such that the RBSs had predicted translation initiation rates of 27306.09 and 32480.74 T.I.R for PETase and MHETase, respectively. The tac promoter (red underline) was also incorporated at the 5' end to drive expression of these genes. |

TABLE 9-continued

Oligonucleotides

| SEQ ID NO: | Oligo | Sequence (5' → 3') | Desc. |
|---|---|---|---|
| | | AGTTGAAGTGGCCGCATGGCGCGACGCTGCC CCGGCTACCGCGTCCGCCGCCGCTCTGCCGG AACACTGCGAAGTTAGCGGCGCCATCGCCAAG CGCACTGGTATTGACGGTTATCCGTACGAAAT CAAGTTCCGCCTGCGCATGCCGGCGGAGTGG AATGGCCGTTTCTTCATGGAGGGTGGTTCCGG CACCAACGGCTCCCTGAGCGCGGCCACCGGC AGCATCGGTGGCGGCCAGATCGCCTCGGCCC TGTCCCGCAACTTCGCCACCATCGCGACCGAC GGTGGCCACGACAACGCTGTCAACGACAATCC AGACGCCCTGGGTACGGTAGCGTTCGGCCTG GACCCACAGGCTCGCCTGGACATGGGTTACAA TTCGTACGACCAGGTGACCCAAGCTGGCAAAG CCGCCGTTGCCCGTTTCTACGGCCGTGCCGCC GACAAGTCGTACTTCATCGGCTGCTCGGAAGG TGGTCGGGAGGGCATGATGCTCAGCCAACGCT TCCCATCCCACTACGACGGTATCGTCGCCGGT GCCCCTGGCTACCAGCTGCCTAAAGCCGGTAT CTCGGGCGCTTGGACCACTCAGTCGCTGGCC CCGGCGGCGGTGGGCCTGGACGCTCAGGGC GTCCCGCTGATCAACAAGAGCTTCTCCGATGC CGACCTGCACCTGCTGTCGCAGGCCATCCTCG GTACTTGCGATGCGCTGGACGGCCTGGCTGAC GGCATCGTTGACAACTACCGCGCGTGCCAGGC CGCTTTCGACCCGGCTACCGCGGCTAACCCTG CCAACGGTCAAGCTCTGCAATGTGTGGGTGCC AAAACCGCCGATTGCCTGAGCCCGGTACAGGT TACCGCCATCAAACGTGCAATGGCCGGCCCGG TCAACAGCGCCGGCACCCCGCTGTACAACCGT TGGGCCTGGGACGCTGGTATGAGCGGCCTGT CCGGTACCACCTACAATCAGGGCTGGCGTTCC TGGTGGCTGGGTAGCTTCAACTCCTCGGCGAA CAACGCGCAGCGTGTTTCGGGTTTCTCCGCCC GCTCCTGGCTGGTCGACTTCGCCACCCCACCA GAGCCTATGCCGATGACCCAGGTGGCTGCAC GCATGATGAAATTCGACTTCGACATCGACCCG CTGAAGATCTGGGCCACCAGCGGCCAGTTCAC CCAGTCGAGCATGGACTGGCACGGGGCCACC TCCACCGACCTGGCCGCCTTCCGCGATCGTGG CGGCAAGATGATCCTGTACCACGGTATGAGCG ACGCAGCCTTCTCGGCCCTGGACACCGCTGAC TACTACGAACGCCTGGGCGCCGCTATGCCGG GCGCCGCGGGCTTCGCTCGTCTGTTCCTCGTC CCAGGCATGAACCACTGTTCGGGCGGTCCAG GTACCGACCGTTTCGACATGCTGACCCCTCTG GTGGCGTGGGTTGAGCGCGGCGAAGCCCGG ACCAGATCTCGGCGTGGAGCGGCACCCCAGG CTACTTCGGCGTCGCTGCCCGTACCCGCCCGC TGTGCCCGTACCCGCAAATCGCACGCTACAAG GGTTCCGGCGATATCAACACCGAAGCAAACTT CGCCTGCGCCGCGCCTCCG | |

TABLE 10

Strains. Subscript indicates the host organism for heterologously expressed genes.†

| Strain Name | Genotype | Construction details | Ref |
|---|---|---|---|
| NEB ® 5-alpha F'I<sup>q</sup> E. coli | F' proA+B+ lacI<sup>q</sup> Δ(lacZ)M15 zzf::Tn10 (Tet<sup>R</sup>)/fhuA2Δ(argF-lacZ)U169 phoA glnV44 Φ80Δ(lacZ)M15 gyrA96 recA1 relA1 endA1 thi-1 hsdR17 | N/A | NEB Cat. C2992 |
| P. putida | Wild-type Pseudomonas putida KT2440 (KT2440) | | ATCC ® 47054 |
| AG3454 | P. putida KT2440 with serine recombinase attB attachment sites. ΔPP_2876::A118 attB-MR11 attB-SPBc attB-φ370 attB; PP_4717-PP_4718::RV attB-TG1 attB-R4 attB-BL3 attB; ΔPP_4740-PP_4741::BxB1 attB-φBT1 attB-φK38 attB-φC1 attB | See Elmore et al. (2017)[6] for details. | Elmore et al. (2017)[6] |

TABLE 10-continued

Strains. Subscript indicates the host organism for heterologously expressed genes.†

| Strain Name | Genotype | Construction details | Ref |
|---|---|---|---|
| TDM461 | P. putida KT2440 ΔhsdM-hsdR::$P_{tac}$:tphA2$_{II}$A3$_{II}$B$_{II}$A1$_{II-E6}$ fpvA:$P_{tac}$:tpaK$_{RHA1}$ | | This study |
| RC002 | P. putida KT2440 ΔgclR | pLJ062 was transformed into KT2440. Deletion of gclR was confirmed by cPCR with oLJ430 and oLJ431 (2.5 kB). | This study |
| RC024 | P. putida KT2440 ΔgclR $P_{tac}$:glcDEFG:PP_3749 | pRC001 was transformed into RC002. Integration of the $P_{tac}$ promoter was confirmed by cPCR with oCJ911 and oCJ912 (436 bp). | This study |
| RC025 | P. putida KT2440 ΔhsdM-hsdR::$P_{tac}$:tphA2$_{II}$A3$_{II}$B$_{II}$A1$_{II-E6}$ fpvA:$P_{tac}$:tpaK$_{RHA1}$ ΔgclR | pLJ062 was transformed into TDM461. Deletion of gclR was confirmed by cPCR with oLJ430 and oLJ431 (2.5 KB). | This study |
| RC026 | P. putida KT2440 ΔhsdM-hsdR::$P_{tac}$:tphA2$_{II}$A3$_{II}$B$_{II}$A1$_{II-E6}$ fpvA:$P_{tac}$:tpaK$_{RHA1}$ $P_{tac}$:glcDEFG:PP_3749 ΔgclR | pRC001 was transformed into RC025. Integration of the $P_{tac}$ promoter was confirmed by cPCR with oCJ911 and oCJ912 (436 bp). | This study |
| RC038 | P. putida KT2440 ΔhsdM-hsdR::$P_{tac}$:tphA2$_{II}$A3$_{II}$B$_{II}$A1$_{II-E6}$ fpvA:$P_{tac}$:tpaK$_{RHA1}$ $P_{tac}$:glcDEFG:PP_3749 ΔgclR::PETase$_{Is}$:MHETase$_{Is}$ | pRC004 was transformed into RC026. Integration of the PETase and MHETase genes was confirmed by cPCR with oLJ430 and oLJ431 (5.5 KB). | This study |
| AW165 | P. putida KT2440 ΔhsdM-hsdR::$P_{tac}$:tphA2$_{II}$A3$_{II}$B$_{II}$A1$_{II-E6}$ fpvA:$P_{tac}$:tpaK$_{RHA1}$ $P_{tac}$:glcDEFG:PP_3749 ΔgclR::PETase$_{Is}$:MHETase$_{Is}$ ΔpcaIJ | pCJ059 was transformed into RC038. Deletion of pcaIJ was confirmed by cPCR with oCJ366 and oCJ367 (2.0 KB). | This study |

†Subscript key: E6, Comamonas sp. E6; RHA1, Rhodococcus jostii RHA1; Is, Ideonella sakiensis.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A genetically modified *Pseudomonas* sp. organism, comprising:
    a nucleic acid sequence encoding a functional *Ideonella sakaiensis* PETase comprising a nucleic acid sequence encoding for a first secretion signal peptide; and
    a nucleic acid sequence encoding a functional *Ideonella sakaiensis* MHETase comprising a nucleic acid sequence encoding for a second secretion signal peptide;
    wherein the genetically modified organism metabolizes bis(2-hydroxyethyl) terephthalate (BHET) to produce BHET deconstruction products.

2. The genetically modified organism of claim 1, wherein both nucleic acid sequences are codon optimized.

3. The genetically modified organism of claim 1, wherein both nucleic acid sequences are incorporated into the genome of the genetically modified organism.

4. The genetically modified organism of claim 1, wherein the nucleic acid sequence encoding a first secretion signal peptide encodes for a signal peptide with greater than 90% sequence identity to SEQ ID NO: 17; and wherein the nucleic acid sequence encoding for a second secretion signal peptide encodes for a signal peptide with greater than 90% sequence identity to SEQ ID NO: 19.

5. The genetically modified organism of claim 1, wherein the organism is *Pseudomonas putida*.

6. The genetically modified organism of claim 1, wherein the BHET deconstruction products comprise at least one of mono-(2-hydroxyethyl) terephthalate, terephthalate, ethylene glycol, ß-ketoadipate, or muconate.

7. A method comprising contacting poly (ethylene terephthalate) (PET) with the genetically modified organism of claim 1 to produce PET deconstruction products.

8. The method of claim 7, wherein the contacting is performed in minimal salt medium.

* * * * *